US006421556B2

(12) United States Patent
Swanson

(10) Patent No.: US 6,421,556 B2
(45) Date of Patent: Jul. 16, 2002

(54) SYSTEMS AND METHODS FOR CONDUCTING ELECTROPHYSIOLOGICAL TESTING USING HIGH-VOLTAGE ENERGY PULSES TO STUN TISSUE

(75) Inventor: David K. Swanson, Mountain View, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/795,713

(22) Filed: Feb. 28, 2001

Related U.S. Application Data

(63) Continuation of application No. 09/430,835, filed on Nov. 1, 1999, now Pat. No. 6,212,426, which is a continuation of application No. 09/084,065, filed on May 22, 1998, now Pat. No. 6,023,638, which is a continuation-in-part of application No. 08/914,860, filed on Aug. 19, 1997, now Pat. No. 5,759,158, which is a continuation of application No. 08/791,625, filed on Jan. 31, 1997, now abandoned, which is a continuation of application No. 08/508,750, filed on Jul. 28, 1995, now abandoned.

(51) Int. Cl.[7] .................................................. A61B 5/04
(52) U.S. Cl. ....................................................... 600/510
(58) Field of Search ............................... 606/32–34, 41, 606/42; 607/1, 2, 5, 7, 8, 72; 600/500, 510, 554, 515, 518

(56) References Cited

U.S. PATENT DOCUMENTS

| 3,577,017 A | 5/1971 | Duke |
| 3,645,267 A | 2/1972 | Hagfors |
| 3,889,263 A | 6/1975 | Johannessen |
| 4,011,463 A | 3/1977 | Fasching |
| 4,056,105 A | 11/1977 | Ravas |
| 4,191,992 A | 3/1980 | Johannessen |
| 4,211,230 A | 7/1980 | Woltosz |
| 4,272,692 A | 6/1981 | Morse |
| 4,394,583 A | 7/1983 | Standing |
| 4,513,748 A | 4/1985 | Nowogrodzki et al. |
| 4,600,411 A | 7/1986 | Santamaria |

(List continued on next page.)

FOREIGN PATENT DOCUMENTS

WO    WO97/04702    2/1997

OTHER PUBLICATIONS

U.S. application No. 09/073,874, filed May 22. 1998.
Presently Pending Claims in U.S. application No. 09/073,874, filed May 22, 1998.

Primary Examiner—George R. Evanisko
(74) Attorney, Agent, or Firm—Henricks, Slavin & Holmes LLP

(57) ABSTRACT

Systems and methods for diagnosing and treating tissue transmit an electrical energy pulse that temporarily stuns a zone of tissue, temporarily rendering it electrically unresponsive. The systems and methods sense an electrophysiological effect due to the transmitted pulse. The systems and methods alter an electrophysiological property of tissue in or near the zone based, at least in part, upon the sensed electrophysiological effect. The alteration of the electrophysiological property can be accomplished, for example, by tissue ablation or by the administration of medication. In a preferred implementation, radio frequency energy is used to both temporarily stun tissue and to ablate tissue through a common electrode.

30 Claims, 22 Drawing Sheets

U.S. PATENT DOCUMENTS

| | | |
|---|---|---|
| 4,660,571 A | 4/1987 | Hess et al. |
| 4,682,596 A | 7/1987 | Bales et al. |
| 4,768,512 A | 9/1988 | Imran |
| 4,782,242 A | 11/1988 | Kovacs |
| 4,785,815 A | 11/1988 | Cohen |
| 4,803,378 A | 2/1989 | Richardson |
| 4,869,248 A | 9/1989 | Narula |
| 4,896,671 A | 1/1990 | Cunningham et al. |
| 4,953,564 A | 9/1990 | Berthelsen |
| 5,088,489 A | 2/1992 | Lerman |
| 5,156,151 A | 10/1992 | Imran |
| 5,222,501 A | 6/1993 | Ideker et al. |
| 5,246,438 A | 9/1993 | Langberg |
| 5,282,840 A | 2/1994 | Hudrlik |
| 5,323,781 A | 6/1994 | Ideker et al. |
| 5,324,284 A | 6/1994 | Imran |
| 5,350,416 A | 9/1994 | Guderian |
| 5,364,393 A | 11/1994 | Auth et al. |
| 5,431,649 A | 7/1995 | Mulier et al. |
| 5,433,198 A | 7/1995 | Desai |
| 5,450,846 A | 9/1995 | Goldreyer |
| 5,454,370 A | 10/1995 | Avitall |
| 5,471,982 A | 12/1995 | Edwards et al. |
| 5,510,800 A | 4/1996 | McEwan |
| 5,514,919 A | 5/1996 | Walley |
| 5,540,681 A | 7/1996 | Struhl et al. |
| 5,661,490 A | 8/1997 | McEwan |
| 5,681,308 A | 10/1997 | Edwards et al. |
| 5,759,158 A * | 6/1998 | Swanson .................. 600/508 |
| 5,767,592 A | 6/1998 | Boys et al. |
| 5,769,846 A | 6/1998 | Edwards et al. |
| 5,868,743 A | 2/1999 | Saul et al. |
| 5,906,615 A | 5/1999 | Thompson |
| 5,921,982 A | 7/1999 | Lesh et al. |
| 5,983,141 A | 11/1999 | Sluijter et al. |
| 6,008,038 A | 12/1999 | Kröger et al. |
| 6,023,638 A | 2/2000 | Swanson |
| 6,047,211 A | 4/2000 | Swanson |
| 6,070,590 A | 6/2000 | Hoffmann |
| 6,107,699 A | 8/2000 | Swanson |
| 6,246,912 B1 | 6/2001 | Sluijter et al. |

* cited by examiner

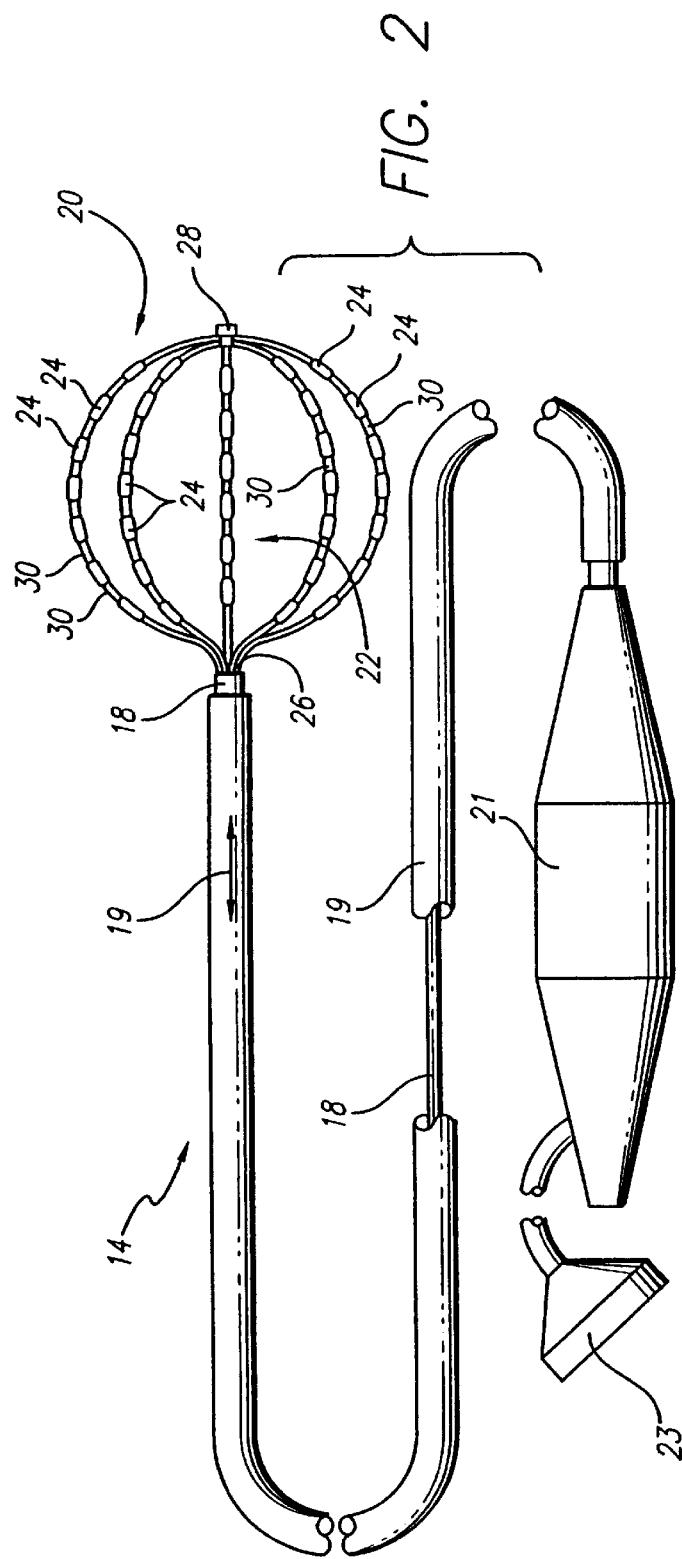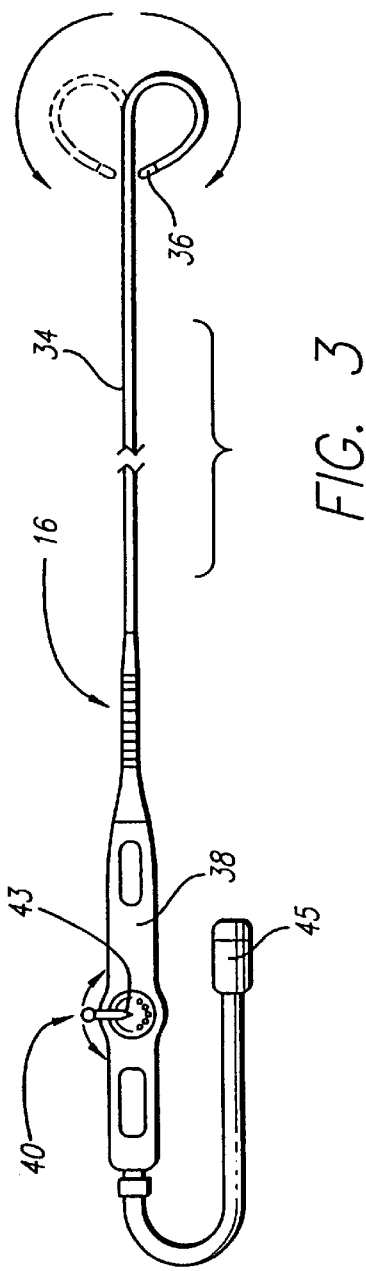

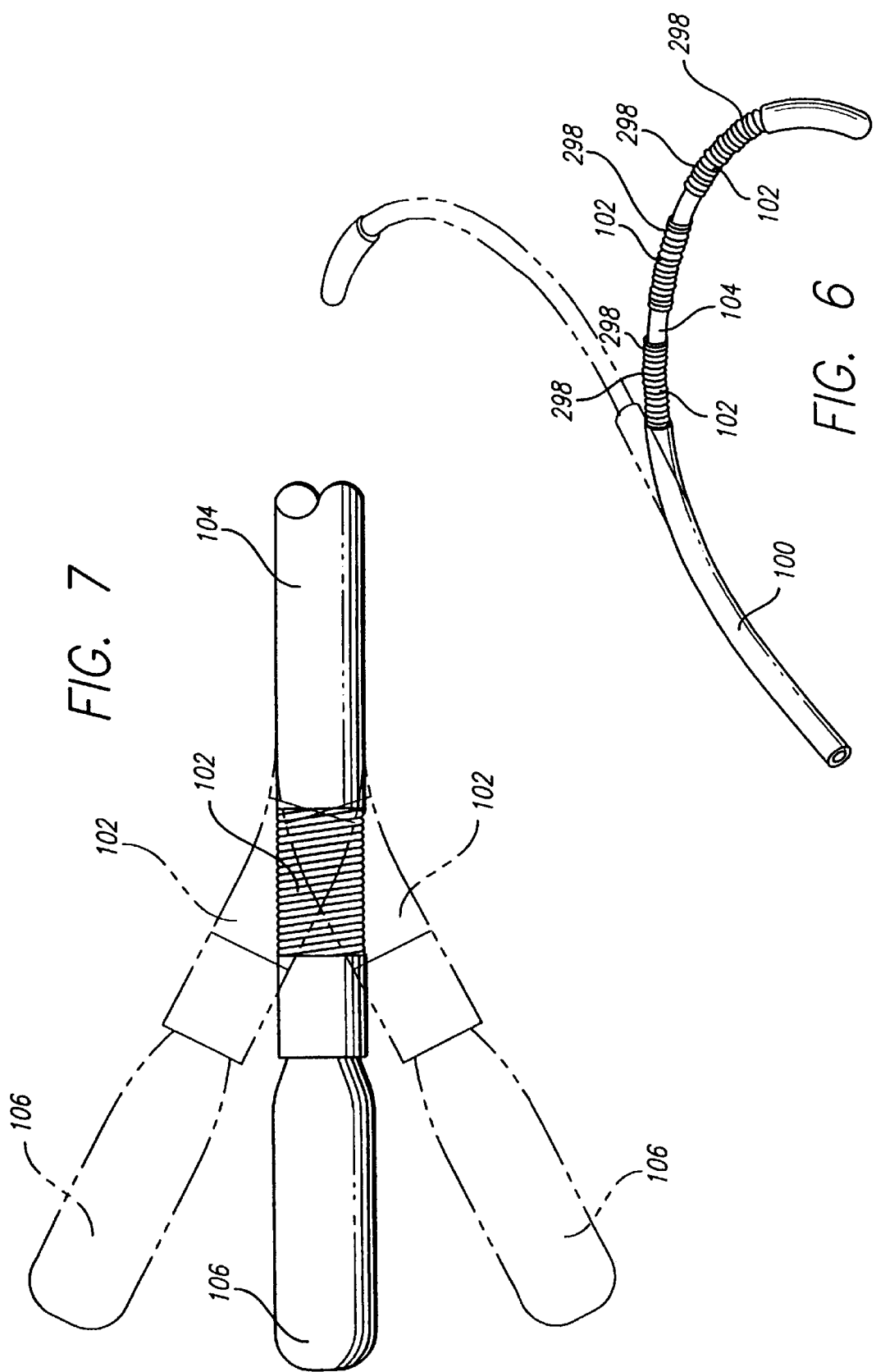

FIG. 11
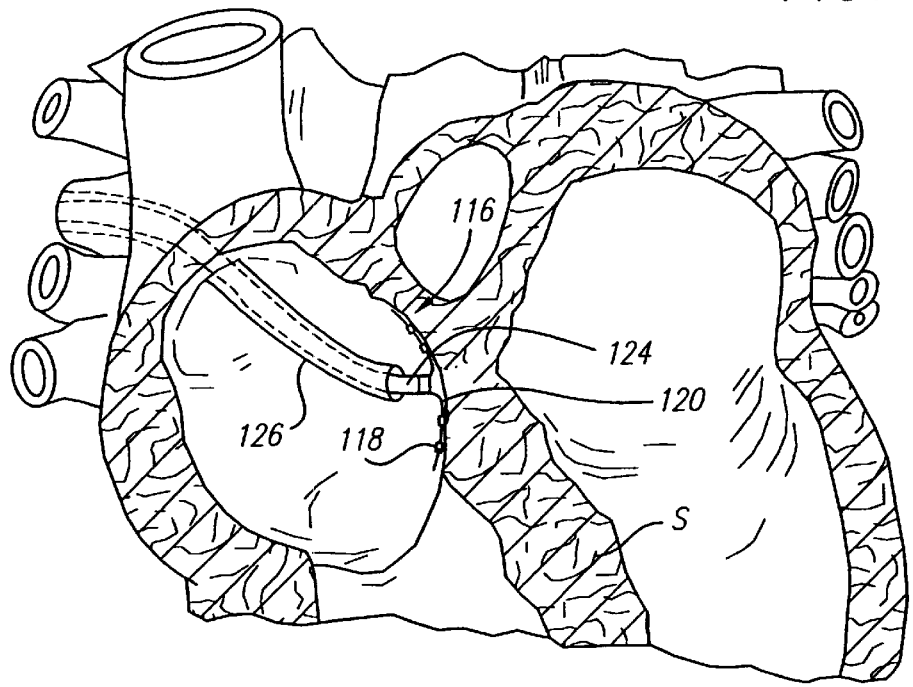
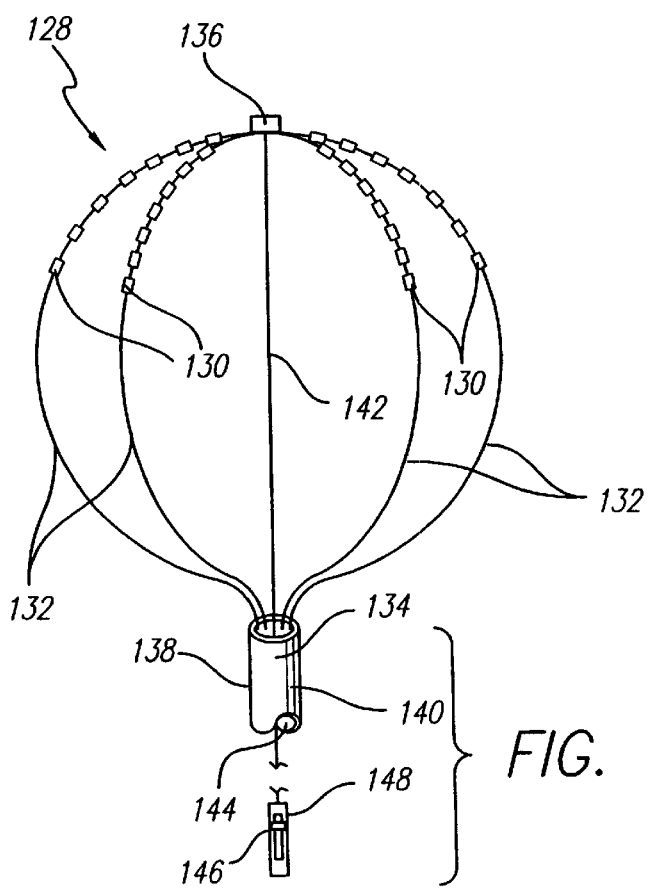
FIG. 12A
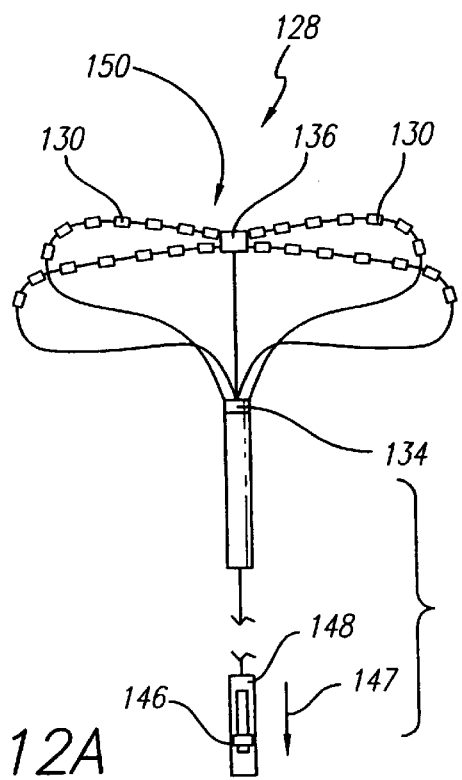
FIG. 12B

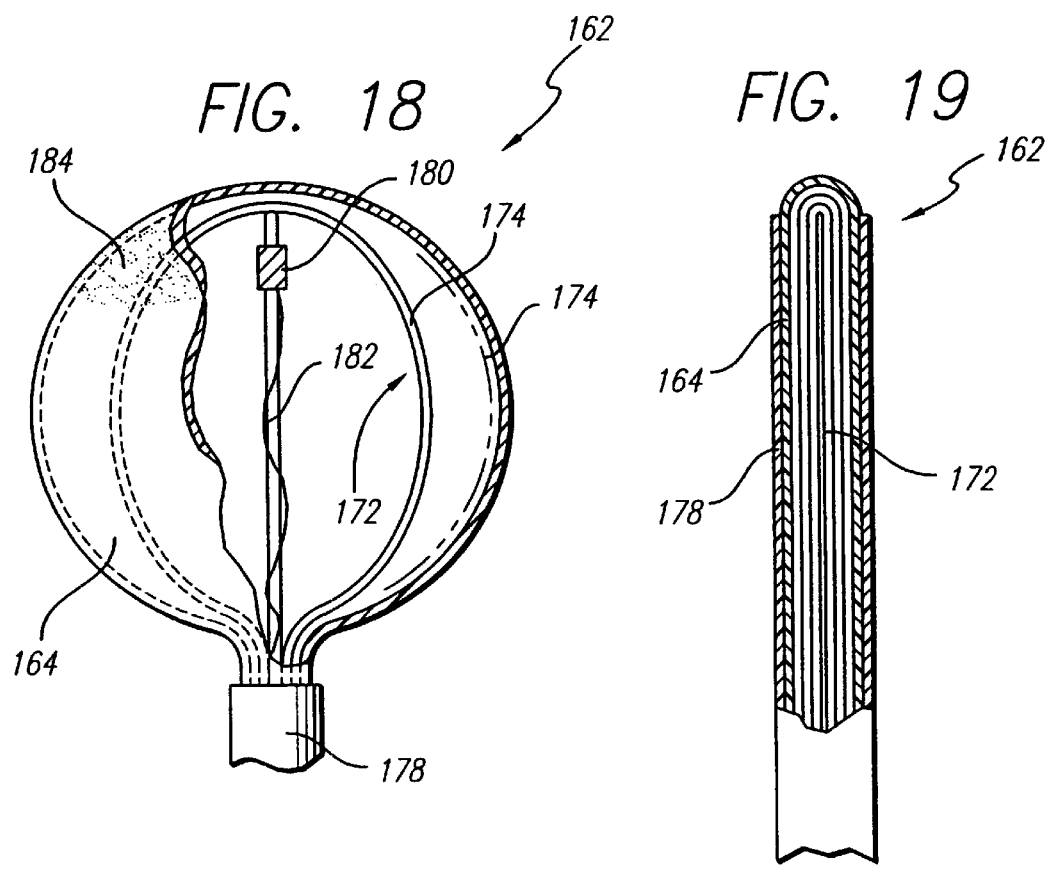
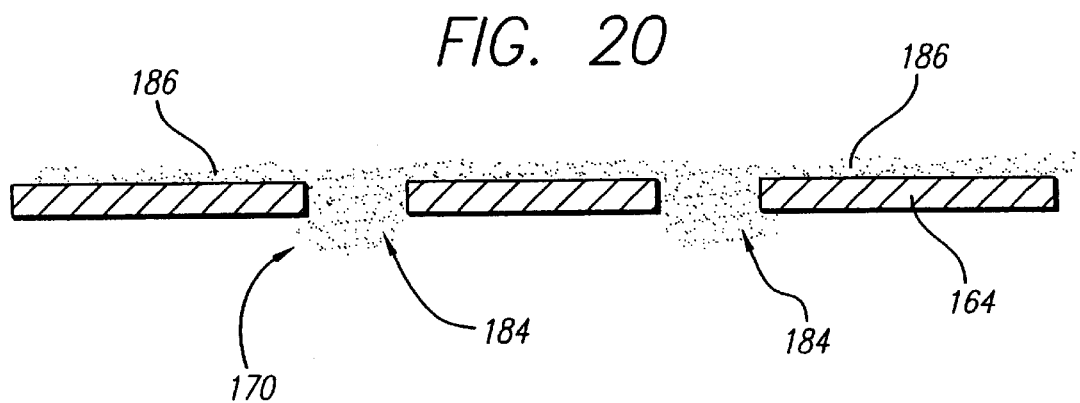

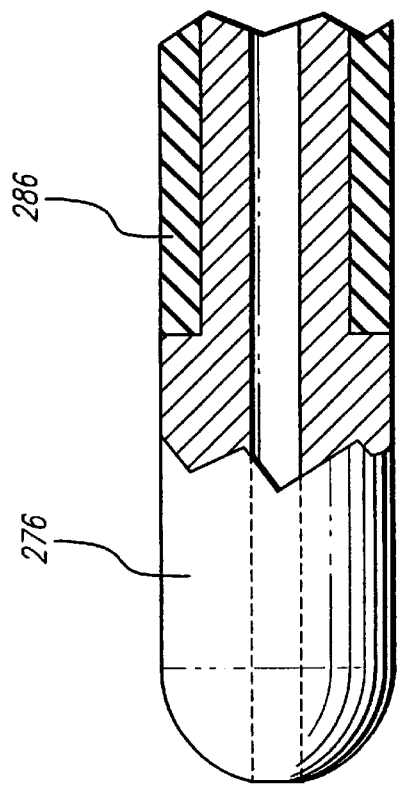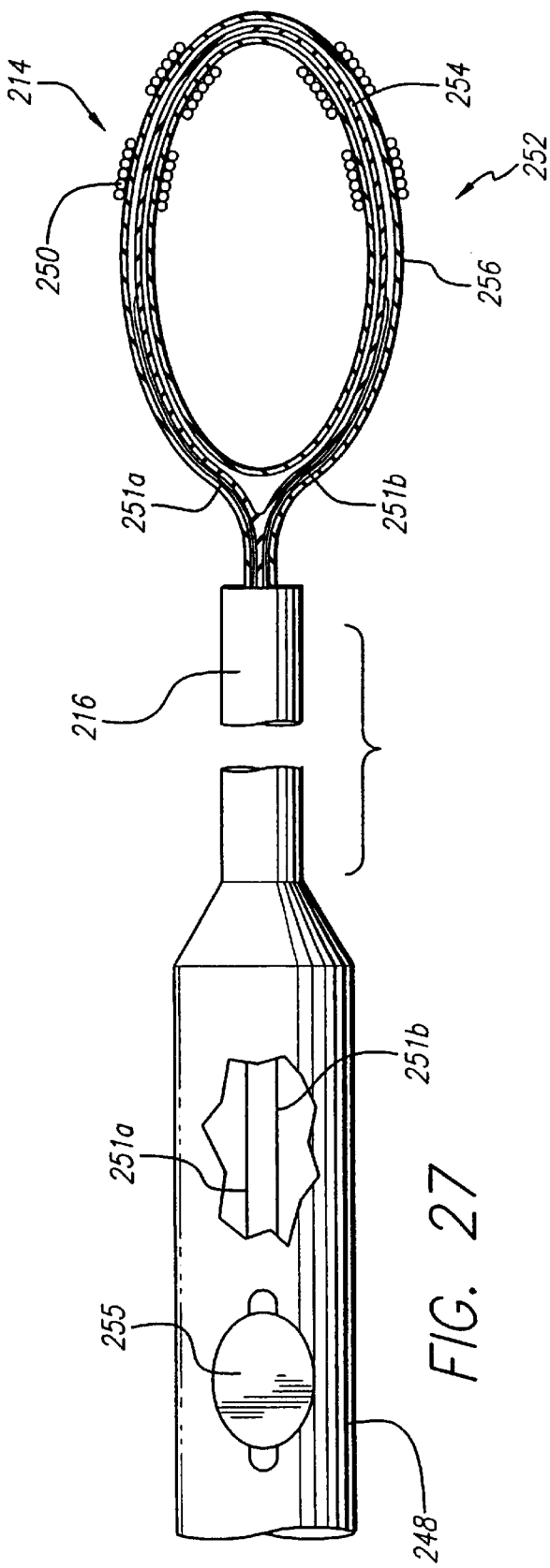

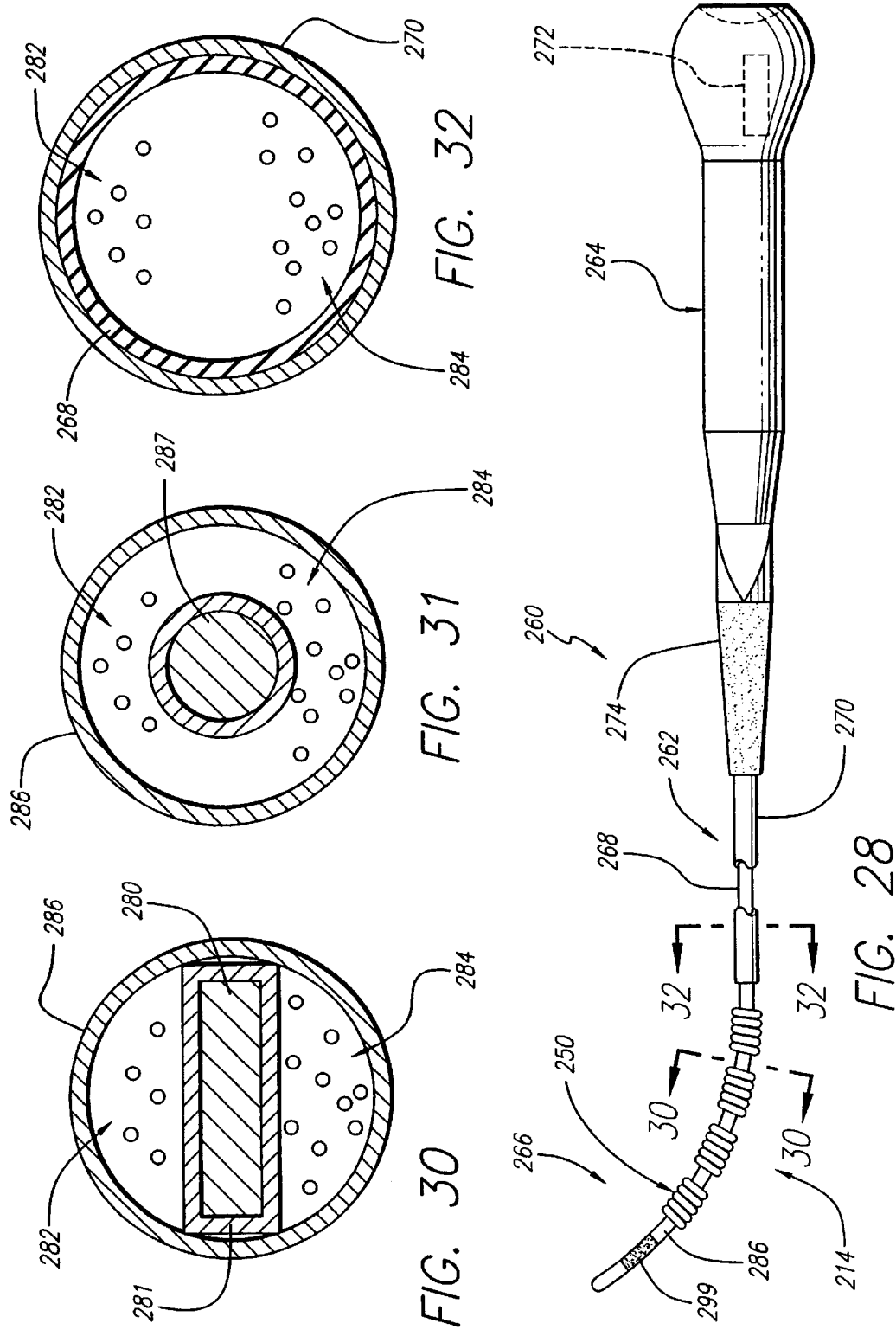

SYSTEMS AND METHODS FOR CONDUCTING ELECTROPHYSIOLOGICAL TESTING USING HIGH-VOLTAGE ENERGY PULSES TO STUN TISSUE

CROSS-REFERENCE TO RELATED APPLICATIONS

This application is a continuation of U.S. application Ser. No. 09/430,835, filed Nov. 1, 1999, now U.S. Pat. No. 6,212,426, which is a continuation of U.S. application Ser. No. 09/084,065, filed May 22, 1998, now U.S. Pat. No. 6,023,638, which is a continuation-in-part of U.S. application Ser. No. 08/914,860, filed Aug. 19, 1997, now U.S. Pat. No. 5,759,158, which is a continuation of U.S. application Ser. No. 08/791,625, filed Jan. 31, 1997, now abandoned, which is a continuation of U.S. application Ser. No. 08/508,750, filed Jul. 28, 1995, now abandoned, each of which is incorporated herein by reference.

BACKGROUND OF THE INVENTIONS

1. Field of the Inventions

The inventions generally relate to systems and methods for diagnosing or treating medical conditions.

2. Description of the Related Art

There are many medical treatments which involve instances of cutting, ablating, coagulating, destroying, or otherwise changing the physiological properties of tissue (collectively referred to herein as "tissue modification"). For example, tissue modification can be used to change the electrophysiological properties of tissue. Although treatments that include tissue modification are beneficial, the physiological changes to the tissue are often irreversible and the modification of tissue other than the intended tissue can disable or even kill a patient. Accordingly, physicians must carefully select the tissue that is to be treated in this manner.

One area of medical treatment which involves tissue modification is the ablation of cardiac tissue to cure various cardiac conditions. Normal sinus rhythm of the heart begins with the sinoatrial node (or "SA node") generating a depolarization wave front. The impulse causes adjacent myocardial tissue cells in the atria to depolarize, which in turn causes adjacent myocardial tissue cells to depolarize. The depolarization propagates across the atria, causing the atria to contract and empty blood from the atria into the ventricles. The impulse is next delivered via the atrioventricular node (or "AV node") and the bundle of HIS (or "HIS bundle") to myocardial tissue cells of the ventricles. The depolarization of these cells propagates across the ventricles, causing the ventricles to contract. This conduction system results in the described, organized sequence of myocardial contraction leading to a normal heartbeat.

Sometimes aberrant conductive pathways develop in heart tissue, which disrupt the normal path of depolarization events. For example, anatomical obstacles in the atria or ventricles can disrupt the normal propagation of electrical impulses. These anatomical obstacles (called "conduction blocks") can cause the electrical impulse to degenerate into several circular wavelets that circulate about the obstacles. These wavelets, called "reentry circuits," disrupt the normal activation of the atria or ventricles. As a further example, localized regions of ischemic myocardial tissue may propagate depolarization events slower than normal myocardial tissue. The ischemic region, also called a "slow conduction zone," creates errant, circular propagation patterns, called "circus motion." The circus motion also disrupts the normal depolarization patterns, thereby disrupting the normal contraction of heart tissue.

The aberrant conductive pathways create abnormal, irregular, and sometimes life-threatening heart rhythms, called arrhythmias. An arrhythmia can take place in the atria, for example, as in atrial tachycardia (AT), atrial fibrillation (AFIB) or atrial flutter (AF). The arrhythmia can also take place in the ventricle, for example, as in ventricular tachycardia (VT).

In treating VT and certain other arrhythmias, it is essential that the location of the sources of the aberrant pathways (called substrates) be located. Once located, the tissue in the substrates can be destroyed, or ablated, by heat, chemicals, or other means of creating a lesion in the tissue. Ablation can remove the aberrant conductive pathway, restoring normal myocardial contraction. The lesions used to treat VT are typically relatively deep and have a large surface area. However, there are some instances where shallower lesions will successfully eliminate VT.

The lesions used to treat AFIB, on the other hand, are typically long and thin and are carefully placed to interrupt the conduction routes of the most common reentry circuits. More specifically, the long thin lesions are used to create a maze pattern which creates a convoluted path for electrical propagation within the left and right atria. The lesions direct the electrical impulse from the SA node along a specified route through all regions of both atria, causing uniform contraction required for normal atrial transport function. The lesions finally direct the impulse to the AV node to activate the ventricles, restoring normal atrioventricular synchrony.

Prior to modifying the electrophysiological properties of cardiac tissue by ablation, or by other means of destroying tissue to create lesions, physicians must carefully determine exactly where the lesions should be placed. Otherwise, tissue will be unnecessarily destroyed. In addition, the heart is in close proximity to nerves and other nervous tissue and the destruction of this tissue will result in severe harm to the patient.

With respect to the treatment of VT, physicians examine the propagation of electrical impulses in heart tissue to locate aberrant conductive pathways. The techniques used to analyze these pathways, commonly called "mapping," identify regions (or substrates) in the heart tissue which can be ablated to treat the arrhythmia. One form of conventional cardiac tissue mapping techniques uses multiple electrodes positioned in contact with epicardial heart tissue to obtain multiple electrograms. The physician stimulates myocardial tissue by introducing pacing signals and visually observes the morphologies of the electrograms recorded during pacing, which this Specification will refer to as "paced electrograms." The physician visually compares the patterns of paced electrograms to those previously recorded during an arrhythmia episode to locate tissue regions appropriate for ablation. These conventional techniques require invasive open heart surgical techniques to position the electrodes on the epicardial surface of the heart.

Conventional epicardial electrogram processing techniques used for detecting local electrical events in heart tissue are often unable to interpret electrograms with multiple morphologies. Such electrograms are encountered, for example, when mapping a heart undergoing ventricular tachycardia (VT). For this and other reasons, consistently high correct identification rates (CIR) cannot be achieved with current multi-electrode mapping technologies. In treating VT using conventional open-heart procedures, the physician may temporarily render a localized region of myocardial tissue electrically unresponsive during an induced or spontaneous VT episode. This technique, called "stunning," is accomplished by cooling the tissue. If stunning the localize region interrupts an ongoing VT, or suppresses a subsequent attempt to induce VT, the physician ablates the localized tissue region. However, in conventional practice, cooling a significant volume of tissue to achieve a consistent stunning effect is clinically difficult to achieve.

Another form of conventional cardiac tissue mapping technique, called pace mapping, uses a roving electrode in a heart chamber for pacing the heart at various endocardial locations. In searching for the VT substrates, the physician must visually compare all paced electrocardiograms (recorded by twelve lead body surface electrocardiograms (ECG's)) to those previously recorded during an induced VT. The physician must constantly relocate the roving electrode to a new location to systematically map the endocardium.

These techniques are complicated and time consuming. They require repeated manipulation and movement of the pacing electrodes. At the same time, they require the physician to visually assimilate and interpret the electrocardiograms. Because the lesions created to treat VT typically have a large volume, the creation of lesions that are improperly located results in a large amount of tissue being destroyed, or otherwise modified, unnecessarily. Additionally, because these techniques do not distinguish between VTs that require a deep lesion, and VTs that can be treated with a more shallow lesion, tissue will be unnecessarily modified when a deep lesion is made to treat VTs that only require a more shallow lesion.

Turning to the treatment of AFIB, anatomical methods are used to locate the areas to be ablated or otherwise modified. In other words, the physician locates key structures such as the mitral valve annulus and the pulmonary veins. Lesions are typically formed that block propagations near these structures. Additional lesions are then formed which connect these lesions and complete the so-called "maze pattern." However, the exact lesion pattern, and number of lesions created, can vary from patient to patient. This can lead to tissue being unnecessarily destroyed in patients who need fewer lesions than the typical maze pattern.

Another issue that often arises in the treatment of AFIB is atrial flutters which remain after the physician finishes the maze procedure. Such flutters are the result of gaps in the lesions that form the maze pattern. The gaps in the lesions must be located so that additional tissue modification procedures may be performed to fill in the gaps. Present method of locating these gaps are, however, difficult and time consuming.

There thus remains a real need for systems and procedures that simplify the process of locating tissue that is intended for cutting, ablating, coagulating, destroying, or otherwise changing its physiological properties.

SUMMARY OF THE INVENTIONS

One aspect of a present invention provides systems and methods for conducting diagnostic testing of tissue. The systems and methods transmit an electrical energy pulse that temporarily renders a zone of tissue electrically unresponsive. The systems and methods may also sense an electrophysiological effect due to the transmitted pulse. Based at least in part upon the sensing of the electrophysiological effect, the physician can determine whether the temporarily unresponsive tissue is in fact the tissue that is intended for modification. Thus, the present invention allows the physician to easily identify the tissue that is intended for modification, as well as tissue that is not.

In the area of cardiac treatment, for example, temporarily rendering localized zones of myocardial tissue electrically unresponsive allows the physician to locate potential pacemaker sites, slow conduction zones and other sources of aberrant pathways associated with arrhythmia. Using the same process, the physician can selectively alter conduction properties in the localized zone, without changing electrophysiological properties of tissue outside the zone. With respect to the treatment of VT, the present invention allows a physician to temporarily create a large, deep area of electrically unresponsive tissue and then determine whether such tissue should be made permanently electrically unresponsive by performing tests which show whether or not the VT has been eliminated. When treating AFIB, the physician can create continuous long, thin areas of electrically unresponsive tissue and then perform testing if required to insure that the permanent modification of the temporarily unresponsive tissue would create the desired therapeutic effect. Similar techniques may also be used to precisely locate the sources of AF.

Once it is determined that the temporarily unresponsive tissue is the tissue that should be permanently modified to cure the VT, AFIB or other arrhythmia, the physician can alter an electrophysiological property of the myocardial tissue in or near the diagnosed zone. The electrophysiological property of myocardial tissue can be altered, for example, by ablating myocardial tissue in or near the zone. The physician will not ablate the tissue if the zone does not meet preestablished criteria for ablation.

During procedures that are performed in and around neural tissue, physicians can render the tissue temporarily unresponsive prior to permanent modification. Tests can then be performed to determine whether unwanted paralysis is present. If it is not, the physician can proceed with modification.

In a preferred embodiment, the systems and methods use radio frequency energy to both temporarily render tissue electrically unresponsive as well as modify the tissue, should the established criteria be met. The same electrode (or series of electrodes) may be used to transmit the radio frequency energy, which, in one mode, temporarily renders the tissue electrically unresponsive and which, in a second mode, ablates or otherwise modifies the tissue.

Another one of the present inventions is an electrical energy generating device. A preferred embodiment of the device includes a first element that, when activated, generates for transmission by an electrode (or series of electrodes) coupled to the device an electrical energy pulse that temporarily renders tissue electrically unresponsive. The device also comprises a second element that, when activated, generates for transmission by an electrode (or series of electrodes) coupled to the device electrical energy to modify tissue by, for example, ablating the tissue. A switch may be provided which selects for activation either the first element or the second element.

The above described and many other features and attendant advantages of the present inventions will become apparent as the invention becomes better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 2 is an enlarged perspective view of a multiple-electrode structure that may be used in association with the system shown in FIG. 1.

FIG. 3 is an enlarged view of a tissue modification device that may be used in association with the system shown in FIG. 1.

FIG. 6 is a perspective view of a flexible probe that includes a plurality of flexible electrodes in accordance with one embodiment of a present invention.

FIG. 7 is a side view of a flexible probe that includes a flexible electrode and a tip electrode in accordance with one embodiment of a present invention.

FIG. 11 is a side section view of the interior of the heart with the probe shown in FIG. 9 positioned against the septal wall of the right atrium.

FIG. 12A is a side view of a probe including a high density array of electrodes.

FIG. 12B is a side view of the probe shown in FIG. 12A with the array of electrodes in a generally flat orientation.

FIG. 18 is a side view, with portions broken away, of a porous electrode structure in accordance with another embodiment of a present invention.

FIG. 19 is side, section view of the porous electrode structure shown in FIG. 18 in a collapsed state.

FIG. 20 is a section view taken generally along line 20—20 in FIG. 17.

FIG. 27 is a partial front, partial section view of a surgical device for positioning an operative element within a patient in accordance with a preferred embodiment of a present invention.

FIG. 28 is a side view of a surgical device for positioning an operative element within a patient in accordance with another preferred embodiment of a present invention.

FIG. 29 is a side, partial section view of an alternate tip that may be used in conjunction with the device shown in FIG. 28.

FIG. 30 is a section view of the distal portion of the device shown in FIG. 28 taken along line 30—30 in FIG. 28.

FIG. 31 a section view of an alternate distal portion for the device shown in FIG. 30.

FIG. 32 is a section view taken along line 32—32 in FIG. 28.

DESCRIPTION OF THE PREFERRED EMBODIMENTS

The following is a detailed description of the best presently known modes of carrying out the inventions. This description is not to be taken in a limiting sense, but is made merely for the purpose of illustrating the general principles of the invention.

The detailed description of the preferred embodiments is organized as follows:

I. Mapping and Stunning-Modification Systems
   A. Mapping Devices
   B. Process Controller
   C. Stunning-Modification Device
   D. Power Supply
   E. Electrode Selecting Device
   F. Graphical User Interface-Based System II. Additional Devices That May be Used in a Stunning-Modification System
  A. Multiple Electrode Stunning-Modification Devices
  B. Structures For Positioning Electrodes in a Three-Dimensional Array
  C. Expandable-CollapsiblePorous Electrode Structures
  D. Surgical Probes
  E. Regenerated Cellulose Coating
  F. Temperature Sensors
III. Modes of Operation
  A. Stunning Mode
  B. Power Considerations Associated With Stunning
  C. Modification Mode
  D. Roving Pacing Mode
  E. Electrophysiological Diagnosis Mode
IV. Bypass and Non-Bypass Environment Considerations The section titles and overall organization of the present detailed description are for the purpose of convenience only and are not intended to limit the present invention.

I. Mapping and Stunning-Modification System

Figure 1:
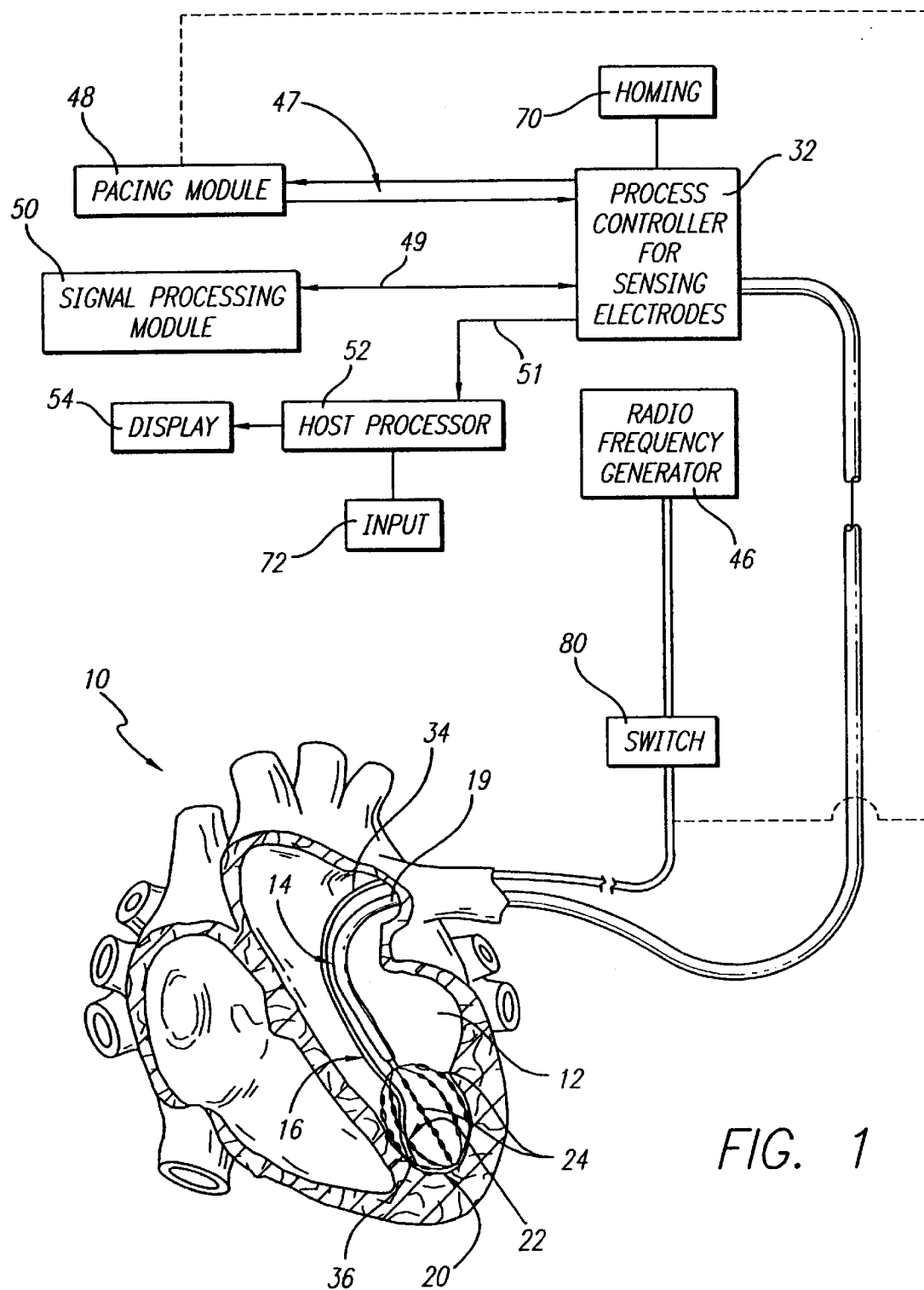
FIG. 1 is a diagrammatic view of a system for accessing a targeted tissue region in the body for diagnostic or therapeutic purposes in accordance with one embodiment of a present invention.

FIG. 1 shows an exemplary system 10 for analyzing endocardial electrical events, using catheter-based, vascular access techniques in accordance with one embodiment of a present invention. The system 10 examines the depolarization of heart tissue that is subject to an arrhythmia and locates a potential tissue site for ablation or other modification.

The exemplary system 10 shown in FIG. 1 includes a mapping probe 14 and a multi-purpose stunning-modification probe 16. Each probe is separately introduced into the selected heart region 12 through a vein or artery (typically the femoral vein or artery) through suitable percutaneous access. The mapping probe 14 and multi-purpose stunning-modification probe 16 can be assembled in an integrated structure for simultaneous introduction and deployment in the heart region 12. Further details of the deployment and structures of the probes 14 and 16 are set forth in U.S. Pat. No. 5,636,634, entitled "Systems and Methods Using Guide Sheaths for Introducing, Deploying, and Stabilizing Cardiac Mapping and Ablation Probes," which is incorporated herein by reference.

Other types of catheter-based mapping and stunning-modification probes may also be used. Additionally, the mapping and/or stunning-modification probes do not have to be catheter-based and can be in the form of probes that are inserted into the heart through a thoracotomy, thoracostomy or median sternotomy. Examples of such structures are discussed in Section II-D below.

A. Mapping Devices

Exemplary mapping device 14 has a flexible catheter body 18. The distal end of the catheter body 18 carries a three-dimensional multiple-electrode structure 20. In the illustrated embodiment, the structure 20 takes the form of a basket defining an open interior space 22 (see FIG. 2). It should be appreciated that other three-dimensional structures could be used.

As FIG. 2 shows, the illustrated basket structure 20 comprises a base member 26 and an end cap 28. Generally flexible splines 30 extend in a circumferentially spaced relationship between the base member 26 and the end cap 28.

The splines 30 are preferably made of a resilient, biologically inert material, like Nitinol metal or silicone rubber. The splines 30 are connected between the base member 26 and the end cap 28 in a resilient, pretensed, radially expanded condition, to bend and conform to the endocardial tissue surface they contact. In the illustrated embodiment (see FIG. 2), eight splines 30 form the basket structure 20. Additional or fewer splines 30 could be used.

The splines 30 carry an array of electrodes 24. In the illustrated embodiment, each spline 30 carries eight electrodes 24. Of course, additional or fewer electrodes 24 can be used.

A slidable sheath 19 is movable along the axis of the catheter body 18 (shown by arrows in FIG. 2). Moving the sheath 19 forward causes it to move over the basket structure 20, collapsing it into a compact, low profile condition for introducing into the heart region 12. Moving the sheath 19 rearward frees the basket structure 20, allowing it to spring open and assume the pretensed, radially expanded position shown in FIG. 2. The electrodes are urged into contact against the surrounding heart tissue.

Further details of a suitable basket structure are disclosed in U.S. patent application Ser. No. 08/206,414, filed Mar. 4, 1994, and PCT Publication No. WO 9421166, both entitled "Multiple Electrode Support Structures."

In use, the electrodes 24 sense electrical events in myocardial tissue for the creation of electrograms. The electrodes 24 are electrically coupled to a process controller 32 (see FIG. 1). A signal wire (not shown) is electrically coupled to each electrode 24. The wires extend through the body 18 of the device 14 into a handle 21 (see FIG. 2), in which they are coupled to an external multiple pin connector 23. The connector 23 electrically couples the electrodes to the process controller 32.

Alternatively, multiple electrode structures can be located epicardially using a set of catheters individually introduced through the coronary vasculature (e.g., retrograde through the aorta or coronary sinus), as disclosed in PCT Publication No. WO 9416619, entitled "Multiple Intravascular Sensing Devices for Electrical Activity."

B. Process Controller

In the illustrated embodiment, the process controller 32 induces electrical events in heart tissue by transmitting pacing signals into heart tissue. The process controller 32 senses these electrical events in heart tissue to process and analyze them to locate a potential ablation site.

More particularly (see FIG. 1), the process controller 32 is electrically coupled by a bus 47 to a pacing module 48, which paces the heart sequentially through individual or pairs of electrodes to induce depolarization. Details of the process controller 32 and pacing module 48 are described in U.S. Pat. No. 5,494,042, entitled "Systems and Methods for Deriving Electrical Characteristics of Cardiac Tissue for Output in Iso-Characteristic Displays."

The process controller 32 is also electrically coupled by a bus 49 to a signal processing module 50. The processing module 50 processes cardiac signals into electrograms. A Model TMS 320C31 processor available from Spectrum Signal Processing, Inc. can be used for this purpose.

The process controller 32 is further electrically coupled by a bus 51 to a host processor 52, which processes the input from the electrogram processing module 50. The output of the host processor 32 can be selectively displayed for viewing by the physician on an associated display device 54. The host processor 32 can be a Pentium™-type or other suitable microprocessor. The exemplary process controller 32 operates in two functional modes, called the sampling mode and the matching mode.

Representative matching techniques to find potential ablation sites are described in U.S. patent application Ser. No. 08/390,559, filed Feb. 17, 1995, and PCT Publication No. WO 9625094, both entitled "Systems and Methods for Analyzing Biopotential Morphologies in Body Tissue."

C. Stunning-Modification Device

The exemplary multi-purpose stunning-modification device 16 shown in FIG. 3 includes a flexible catheter body 34 that carries an electrode 36 at the distal tip. The electrode is suitable for ablation and other tissue modification procedures. A handle 38 is attached to the proximal end of the catheter body 34. The handle 38 and catheter body 34 carry a steering mechanism 40 for selectively bending or flexing the catheter body 34 along its length, as the arrows in FIG. 3 show. The steering mechanism 40 can vary. For example, the steering mechanism can be as shown in U.S. Pat. No. 5,254,088, which is incorporated herein by reference.

A wire (not shown) electrically connected to the electrode 36 extends through the catheter body 34 into the handle 38, where it is electrically coupled to an external connector 45. The connector 45 connects the electrode 36 to a generator 46, which supplies electromagnetic radio frequency energy to the electrode 36. As used in this Specification, the term "radio frequency energy" refers to electrical energy with frequencies in the range of between about 10 kHz to about 3 GHz ($3 \times 10^9$ Hz). When operated in a uni-polar mode, an external patch electrode (not shown) constitutes the radio frequency energy return line. When operated in a bi-polar mode, an electrode carried on the catheter body 34, or an electrode carried on a nearby catheter, constitutes the radio frequency energy return line. The generator 46 is operable through an associated switching element 80 in two modes, called the stunning mode and the modification mode.

D. Power Supply

Figure 36:
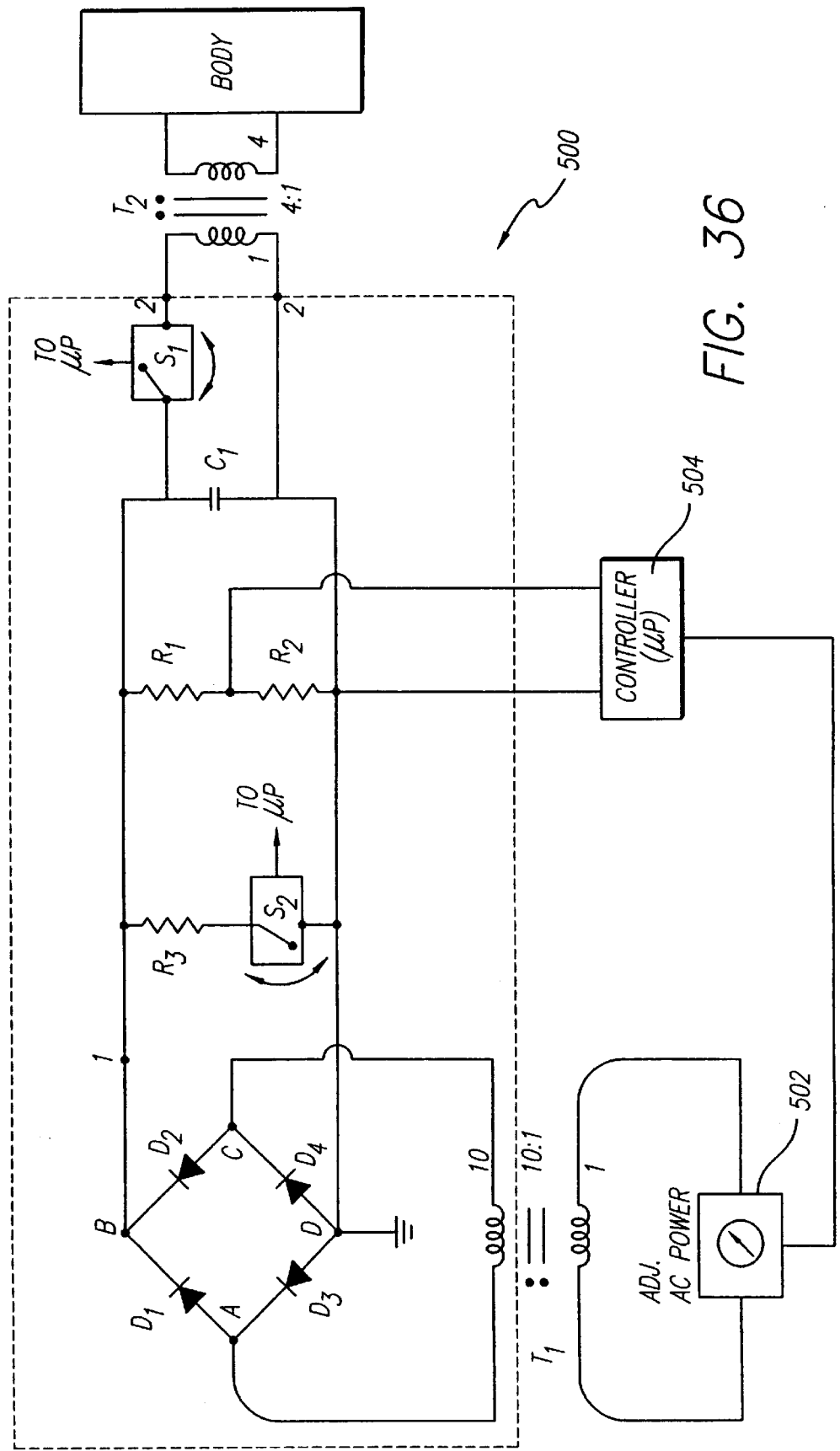
FIG. 36 is a diagram showing one embodiment of a power supply circuit in accordance with the present invention.

FIG. 36 illustrates one preferred embodiment of a power supply circuit 500 for delivering controlled high voltage RF pulses to tissue. In the exemplary circuit, which is a full-wave bridge rectifier and transformer circuit, a stepped up AC voltage from a variably controllable power source 502 is rectified into substantially unidirectional (rectified) pulse waveforms for application to body tissue in a safe and controllable manner.

The circuit includes a first isolation and step-up transformer T1 (preferably having a turns ratio of 10:1) through which power is input from the AC power source 502, and four diodes D1, D2, D3 and D4, with output to the input terminal end of a RC circuit. The RC circuit has at least one shunting capacitor C1, in parallel with resistors R1, R2 and R3 (resistors R1 and R2 are in series with one another and in parallel with resistor R3). The output terminal end of the RC circuit is the voltage drop across the capacitor C1. The RC circuit, which also includes switching devices S1 and S2, can be thought of as resonant-type circuit that stores energy supplied by the AC power supply through the full-wave bridge rectifier, until such time that the RC circuit is selectively discharged through the primary coils of a second isolation and step-up transformer T2 by operation of switching device S1. The switching device S1 connects the transformer T2 with the output voltage drop at capacitor C1. Output from transformer T2 is applied to a load, which is the body of the patient in the stunning and modification systems disclosed herein.

Inputting the AC power from AC power source 502 through the first isolation and step-up transformer T1 provides at least two advantages. First, it allows the AC source voltage to be stepped up (or stepped down) as needed. Second, it isolates the AC power source 502 from the remaining circuit, as shown with dashed lines in FIG. 36, thereby reducing the shock hazard to a patient. A similar function is provided by the second step-up and isolation transformer T2. Accordingly, the isolation and step-up transformers T1 and T2 electrically isolate the portion of the circuit circled with dotted lines from the patient and other circuits.

Step-up transformer T2 provides additional safety protection for the patent, should switching device S1 fail in either the open or closed positions. If switching device S1 fails in the open position, no power is delivered, since no current flows through the primary coils of transformer T2. If the switching device S1 fails in the closed position, substantially rectified voltage waveforms of long duration (predominately DC voltage waveforms) will flow through the primary coils of transformer T2, and only minor variations in current will be reflected at the secondary coils. Thus, the patient is only exposed to RF pulsed voltage waveforms when S1 is properly working and rapidly being switched ON and OFF.

Operation of the exemplary full-wave bridge rectifier shown in FIG. 36 allows for substantial rectification of AC waveforms into substantially rectified or unidirectional pulsed waveforms (allowing for the usual non-ideal behavior of actual circuits, ripple voltage, and the like). The secondary voltage of transformer T1, seen at the output of transformer T1, equals the turns ratio times the primary voltage, e.g., $V_{sec} = (N_{sec}/N_{pri})V_{pri}$. When the input cycle voltage waveform is positive, diodes D1 and D4 are forward-biased and conduct current in the direction from node A to node B, and from node D to node C (node D can be connected to ground), with the portions of the circuit between nodes A to D and nodes B to C being an open circuit by nature of diodes D2 and D3 being reverse biased. When the input cycle is negative, diodes D2 and D3 are forward-biased and conduct current in the direction from node C to node B and from node D to node A, with the portions of the circuit between nodes D to C and nodes A to B being an open circuit, by nature of diodes D1 and D4 being reverse biased. A substantially full-wave rectified output voltage appears across node 1 of the circuit and as seen by the RC circuit to the right of node 1.

Diodes D1–D4, which may be Zener diodes, must have reverse breakdown voltages that exceed the maximum voltage to which the capacitor C1 can be charged. In one preferred embodiment, the diodes D1–D4 have a breakdown voltage of 300 V, and carry a maximum current flow of less than or equal to 0.2 amperes RMS, while capacitor C1 has a value of 10,000 $\mu$F, and is a high-voltage electrolytic capacitor, such as the kind commonly used for flash cameras. Capacitor C1 can be repeatedly charged to 350–400 V, and may be connected in parallel with similar capacitors to achieve the necessary storage capacitance. When charged to 300 volts, capacitor C1 stores about 600 J of energy.

The input AC power is preferably about 5 W and 500 W. However, it should be noted that relatively low levels of input power will reduce the overall flexibility of the system. For example, a 5 W input power source would require at least 2 minutes to fully charge capacitor C1 to the preferred level of about 600 J. Although a smaller capacitor or lower stored voltages would enable more rapid charging, the techniques disclosed herein require the storage of a significant amount of energy as well as rapid delivery to be effective. With respect to the upper preferred limit, power levels higher than about 500 W increase the potential for patient injury in the event of component failure.

The delivered power requirements for stunning targeted tissue using the circuit shown in FIG. 36 is high. In some instances 800 V must be delivered into a 50 $\Omega$ load, requiring 12 kW of power. As noted in Section III-B with respect to the electrodes used in a three-dimensional structure, a RF pulse having an amplitude of 150 volts and a duration of about 10 ms will stun tissue to a depth of 5 mm, while a 800 volt RF pulse at 500 kHz frequency and a duration of 10 ms will stun a tissue to a depth of 10 mm.

Delivery of this high level of power must be carefully controlled, since that level of power can severely injure a patient.

In some special circumstances, voltages as low as 100 V can electrically stun tissue. On the other hand, a short burst of very high voltages (about 4000V) are often required to kill tissue by dielectric breakdown of cell membranes. In order to account for these situations, the voltage outputs from transformer T1 should range from about 100 V to about 4000 V.

In the preferred embodiment, the AC power supply 502 will deliver up to 50 W of power and have a maximum peak-to-peak voltage of 30 V, operating at a frequency of 10–100 kHz. The resistors R1 and R2 may have values of 10 kΩ and 100 Ω, respectively, resulting in a decay time constant of about 2 minutes and an expected monitoring voltage of 0–3 V across R2. R3 is a power resistor with a resistance value of about 100 Ω, which enables a more rapid adjustment of the voltage across capacitor C1, such as when the operator selects a lower stunning voltage. Thus, when switching device S2 is closed, the capacitor C1 is discharged, with a time constant of 1.4 sec.

Switching devices S1 and S2 may be switched ON and OFF to produce a plurality of various amplitude and pulse width duration RF pulses. Switching devices S1 and S2 may be any suitable switching device, whether mechanical, electrical or electromechanical, and are preferably solid state or power semiconductor switches such as an SCR, gate turn-off thyristor (GTO), power MOSFET, transistor, thyristor, or hybrid devices with FET input and a bipolar output stage. The switching devices S1 are S2 are preferably controlled by a processor 504 (which may be part of process controller 32 shown in FIG. 1 or a separate component), and/or with suitable computation circuits, where applicable, to produce in conjunction with the circuit shown in FIG. 36 a plurality or train of waveform pulses of RF frequency at the output 2—2 of the circuit. These voltage pulses are stepped up by transformer T2, having a turns ratio of 4:1, for application to the patient.

Shunting resistors R1 and R2 can serve two purposes. First, when the AC power from power supply 502 is shut off, the resistors drain charge and reduce power from capacitor C1. Second, the voltage across resistor R2 is measured by the controller 504 and is used to control the AC power supply 502. The AC power supply can be controlled by the controller 504 to vary its output power and frequency.

To further provide for isolation, the voltage measurement of resistor R2 by controller 504 may be made by optical isolation, or other isolation measuring techniques such as magnetic isolation or telemetry.

The circuit of FIG. 36 controls the cycle length of the rectified RF pulse, the amplitude of the pulse, and the total duration of the pulse thorough selective discharge of the capacitor through the selective switching of the switching device S2, which discharges the capacitor through shunting resistor R3, and selective switching of switching device S1, which creates a plurality of rectified RF pulse waveforms that feed through step-up transformer T2. This produces a RF voltage pulse train for application to the tissue in the patient's body. The duty cycle of the RF voltage pulse train may also be controlled by the selective switching ON and OFF of switching device S1. The center frequency for the pulse waveform is preferably between about 100 kHz and 1 MHz, with the waveform generated using ON/OFF duty cycles of from 10% to 50%. Frequencies above about 100 Mhz are not effective in a voltage stunning mode because dielectric absorption results in high heating rates in the tissue, while frequencies below about 100 kHz can directly stimulate tissue, which is not desirable.

In one preferred embodiment, the switching device S1 is turned ON and OFF with a cycle length of 2 μsec and a duty cycle of 50%, for a total pulse duration of 10 ms. To produce this pulse train, a train of 5,000 1.0 μsec long pulses turn switching device S1 to the ON state, to create a 10 msec long 500 kHz pulse waveform at the output 2-2 of FIG. 36, which are then suitably stepped up in voltage in a 4:1 ratio by transformer T2 for output to the tissue.

The rectified AC waveform produced by turning switching device S1 ON and OFF at a 500 kHz repetition rate would, in the absence of filtering, produce a nearly square wave. However, finite switching times for the switching device S1 and the transformer T2, which acts as a bandpass filter, strongly filter out the higher harmonics of the base frequency of the pulse waveform, resulting in a stunning waveform as applied to tissue that can be made to be somewhat sinusoidal. Should a more perfect sinusoidal waveform be desired, using the teachings of the present invention one could produce a more perfect sinusoidal waveform by the tuning of the output transformer T2 to the center frequency of the pulse waveform used to stun tissue.

Energy outputted to the patient can be reduced by limiting the power provided by the AC power supply 502 and the energy stored in capacitor C1. For one preferred embodiment of the invention, stored energy at the capacitor C1 is 600 J and the AC power supply used to charge C1 is limited to 50 W. Under maximum transfer rates, C1 is discharged with a time constant of 77 msec. After several hundred msec, C1 is largely discharged, and the power delivery rate will drop to less than 30 W. Plateau power delivery rates to the patient are decreased from 50 W at the AC power supply input to 30 W at the output due to power losses, such as losses in transformers T1 and T2.

It should be noted that the exemplary power supply circuit is susceptible to many variations. The only requirement is that power be supplied to a storage device and discharged from the storage device by way of a switching device that produces the desired pulses. For example, should it be found that their functionality is not required in a particular application, the resistors in the RC circuit could be eliminated. Storage devices other than capacitors may be employed. The AC power supply and rectifier arrangement illustrated in FIG. 36 may be replaced by a battery (or plurality of batteries in series) and a suitable ON/OFF switch. Also, the transformer T2 can be replaced by another type of inductive device.

E. Electrode Selecting Device

Figure 37B:
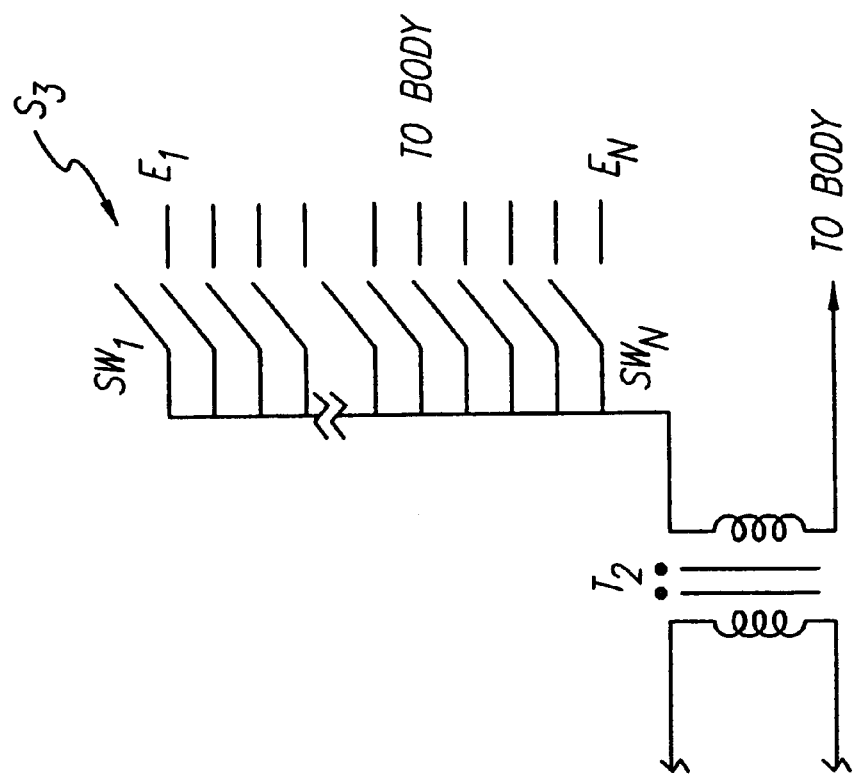
FIG. 37B is a detailed diagram of the switching device shown in FIG. 37A.
Figure 37A:
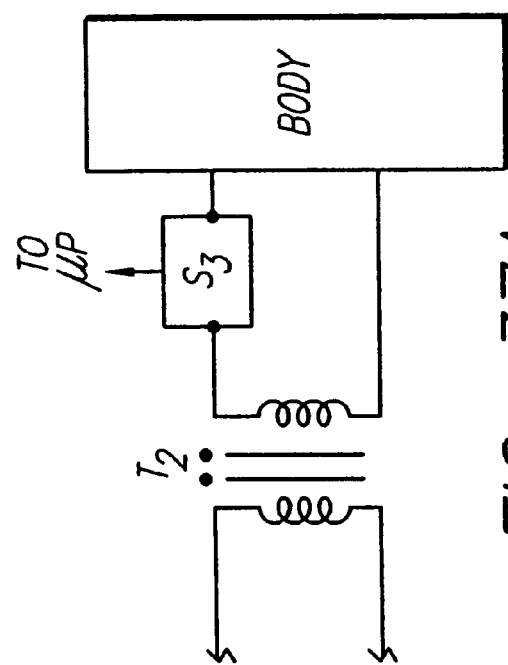
FIG. 37A is a diagram showing where an additional switching device may be added to the circuit shown in FIG. 36.

As discussed in Section III-A, a sequence of stunning pulses can be applied with different electrodes in a multiple electrode structure (such as those discussed in Section II and shown in FIGS. 10–13B) to create a complex pattern of temporarily unresponsive tissue. One example of an electrode selecting device that may be used to switch from one (or more) electrodes to another (or more) electrodes in, for example the circuit shown in FIG. 36, is shown in FIGS. 37A and 37B. Exemplary switching device S3 includes a plurality of mechanical or electromechanical switches $SW_1$–$SW_N$. Preferably, each switch $SW_1$–$SW_N$ is associated with an individual electrode $E_1$–$E_N$. Thus, the state of the switch SW determines whether the associated electrode will deliver the stunning voltage.

Relay or mechanical switches are preferred because these switches can have very low coupling capacitances across the switch, as compared to single solid state power switches. The switches should normally be open in order to promote patient safety and minimize the switching power requirements.

Should relatively fast switching times be desired, four or more switches with relatively low ON resistances could be used in series, thereby decreasing the effective capacitance across the switch. Here, the switch SW may be formed from multiple solid state switches in series. It should be noted, however, that such an arrangement will greatly complicate the switch drive circuitry.

F. Graphical User Interface-Based System

Figure 38:
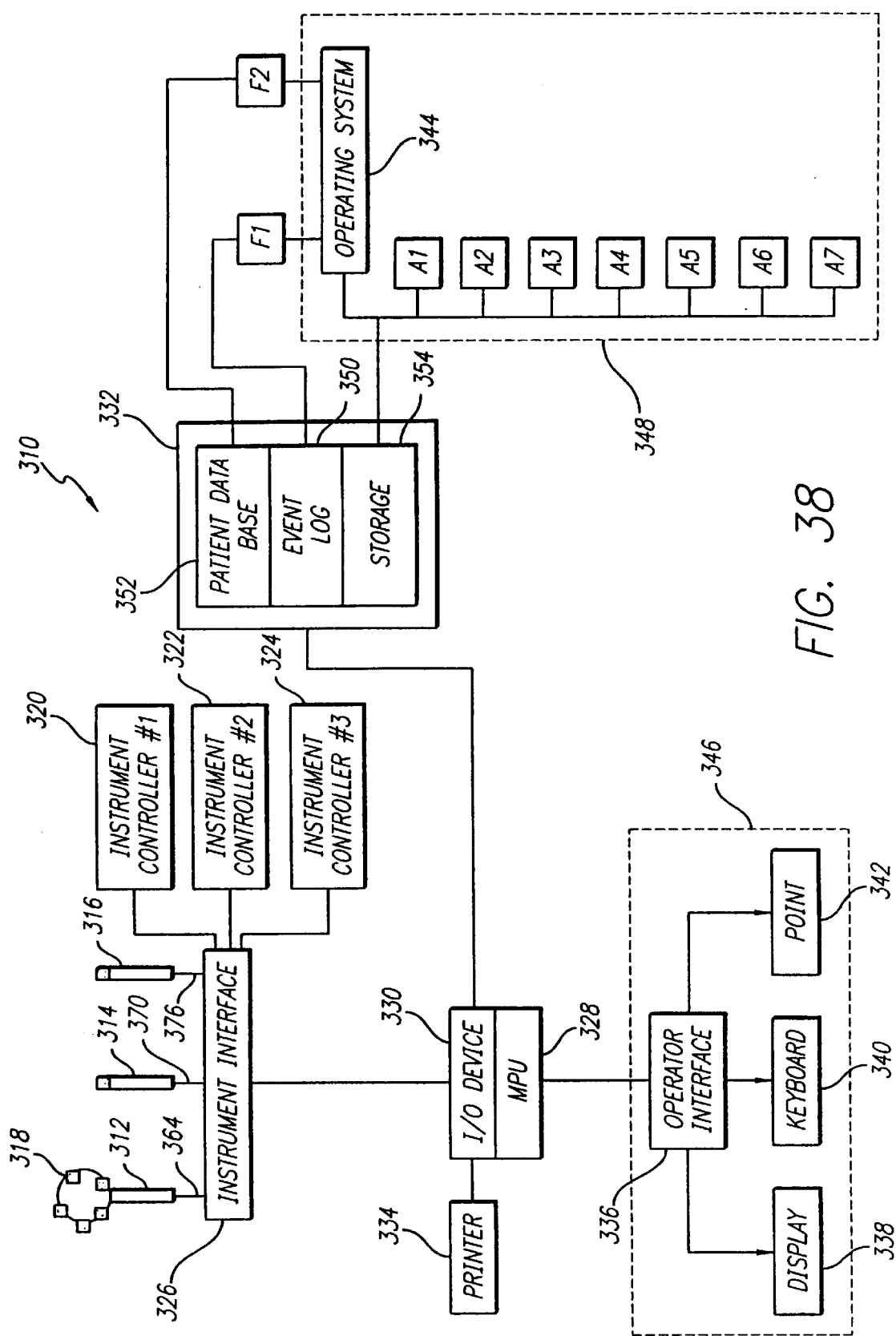
FIG. 38 is a schematic view of an exemplary graphical user interface-based system including various diagnostic and therapeutic instruments.
Figure 39:
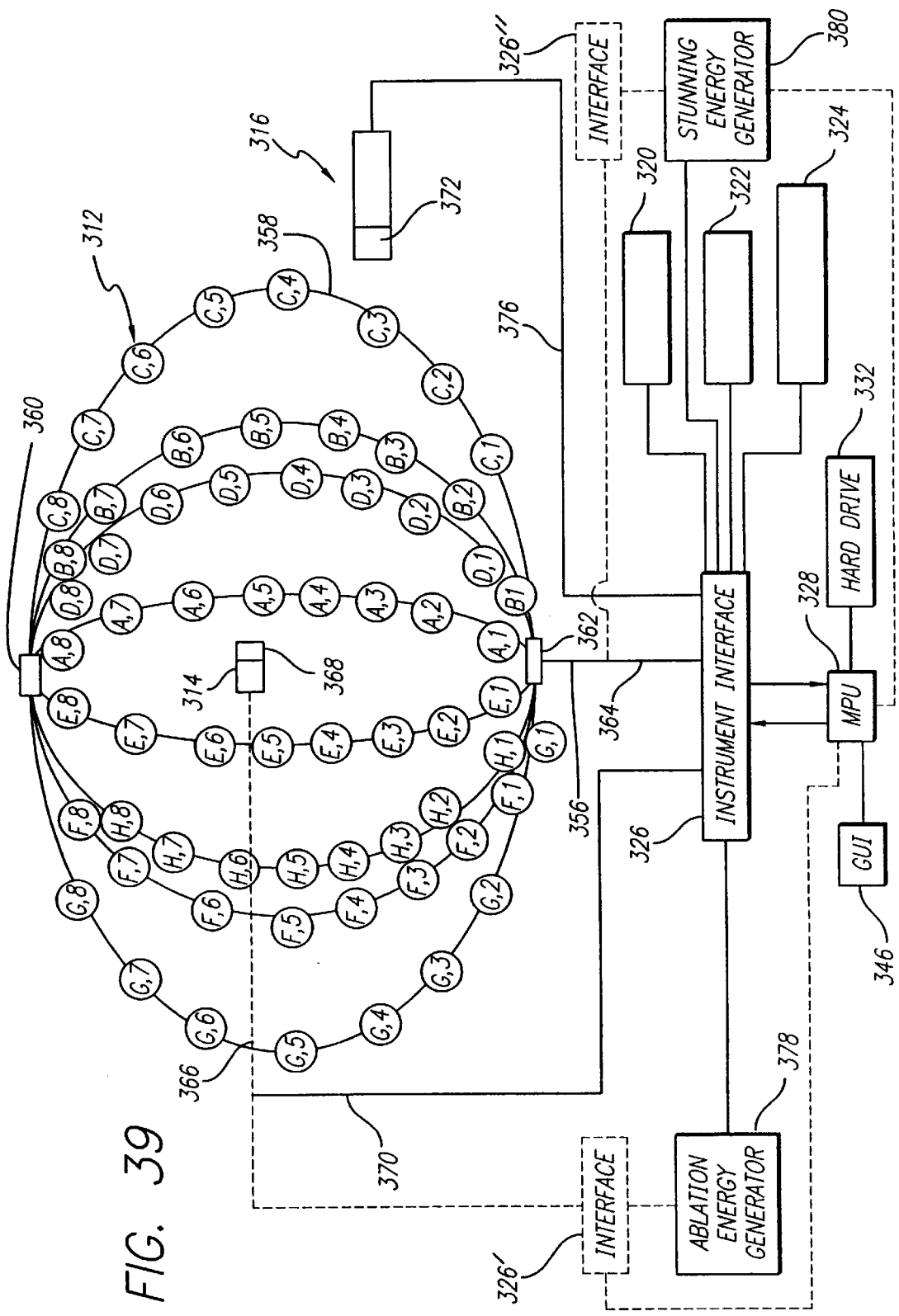
FIG. 39 is a schematic view of an exemplary graphical user interface-based system including various diagnostic and therapeutic instruments.

One example of a graphical user interface-based system that may be used to sequentially apply either a single high voltage pulse or a series of high voltage pulses to tissue is illustrated in FIGS. 38 and 39. In the illustrated embodiment, the system 310 includes an instrument 312 (such as a catheter or surgical probe) having an array of electrodes 318, as well as instruments 314 and 316, which include operative elements usable for diagnostic or therapeutic purposes. One exemplary operative element is a device for imaging body tissue, such as an ultrasound transducer or an array of ultrasound transducers, an optic fiber element, or a CT or MRI scanner. Other exemplary operative elements include device to deliver drugs or therapeutic material to body tissue, or electrodes for sensing a physiological characteristic in tissue or transmitting energy to stimulate or ablate tissue.

The exemplary system 310 includes one or more instrument controllers (designated 320, 322, and 324) which, in use, condition the associated instrument 312, 314, and 316 to perform its respective diagnostic or therapeutic function. To aid in coordinating signal and data flow among the controllers 320, 322, and 324 and their linked instruments, the system 310 includes an interface 326 (or "master switching unit") that establishes electrical flow paths and processes the various diagnostic or therapeutic data and signals in an organized and efficient fashion. A suitable interface is disclosed in U.S. application Ser. No. 08/770,971, entitled "Unified Switching System for Electrophysiological Stimulation and Signal Recording and Analysis," filed Dec. 12, 1996, and incorporated herein by reference.

The exemplary system 310 also includes a main processing unit (MPU) 328, which is preferably a Pentium™ microprocessor. The MPU 328 includes an input/output (I/O) device 330, which controls and monitors signal and data flow to and from the MPU 328. The I/O device 330 can, for example, consist of one or more parallel port links and one or more conventional serial RS-232C port links or Ethernetm communication links. The I/O device 330 is coupled to a data storage module or hard drive 332, as well as to the instrument interface 326 and a printer 334. An operator interface module 336, which is coupled to the I/O device 330, includes a graphics display monitor 338, a keyboard input 340, and a pointing input device 342, such as a mouse or trackball. The graphics display monitor 338 can also provide for touch screen (finger or stylus) input. An operating system 344 for the MPU 328 may, for example, reside as process software on the hard drive 332, which is down loaded to the MPU 328 during system initialization and startup. In the illustrated embodiment, the operating system 344 executes through the operator interface 336 a graphical user interface (GUI) 346.

The operating system 344 administers the activation of a library 348 of control applications, which are designated, for purpose of illustration, as A1 to A7 in FIG. 38. In the illustrated embodiment, the control applications A1 to A7 all reside in storage 354 as process software on the hard drive 332 and are down loaded and run based upon operator input through the GUI 346. Each control application A1 to A7 prescribes procedures for carrying out given functional tasks. Of course, the number and functions of the applications A1 to A7 can vary. Exemplary functions include clinical procedures, specialized navigation applications, and utility applications.

Clinical procedure applications contain the steps to carry out a prescribed clinical procedure, such as the sequential application of stunning pulses to predetermined electrodes in a two or three-dimensional array. A number of such applications may be stored, each corresponding to an area, or areas, of stunned tissue having various shapes and sizes. That way, the physician need only select the desired shape with the GUI 346 to form the desired area of temporarily unresponsive tissue. Similar application programs may be used to form areas of permanently unresponsive tissue using the high voltage pulse-based modification techniques described in Section III-C below.

The navigation applications allow the operator to visualize on the GUI 346 the orientation of the multiple electrode array 312 and instruments 314 and 316, thereby assisting the operator in manipulating and positioning the array and instruments. For example, one navigation application may construct an ideal or virtual image of the deployed array and the instruments, while the other displays an actual, real-time image of each.

Utility applications carry out system testing, system servicing, printing, and other system support functions affecting the applications.

When run by the operating system 344, each application generates prescribed command signals, which the I/O device 330 distributes via the instrument interface 326 to condition the instrument controllers 320, 322, and 324 to perform a desired task using the instruments 312, 314, and 316. The I/O device 326 also receives data from the instrument controllers 320, 322, and 324 via the instrument interface 326 for processing by the procedure application being run. The GUI 346 presents to the operator, in a graphical format, various outputs generated by the procedure application run by the operating system 344 and allows the user to alter or modify specified processing parameters in real time.

The operating system 344 also includes one or more specialty functions (designated F1 and F2 in FIG. 38), which run in the background during execution of the various applications A1 to A7. For example, one function F1 can serve to establish and maintain an event log 350 which keeps time track of specified important system events as they occur during the course of a procedure. Another function F2 can serve to enable the operator, using the GUI 346, to down load patient specific information generated by the various applications A1 to A7 to the hard drive 332 as data base items, for storage, processing, and retrieval, thereby making possible the establishment and maintenance of a patient data base 352 for the system 310.

Figure 13A:
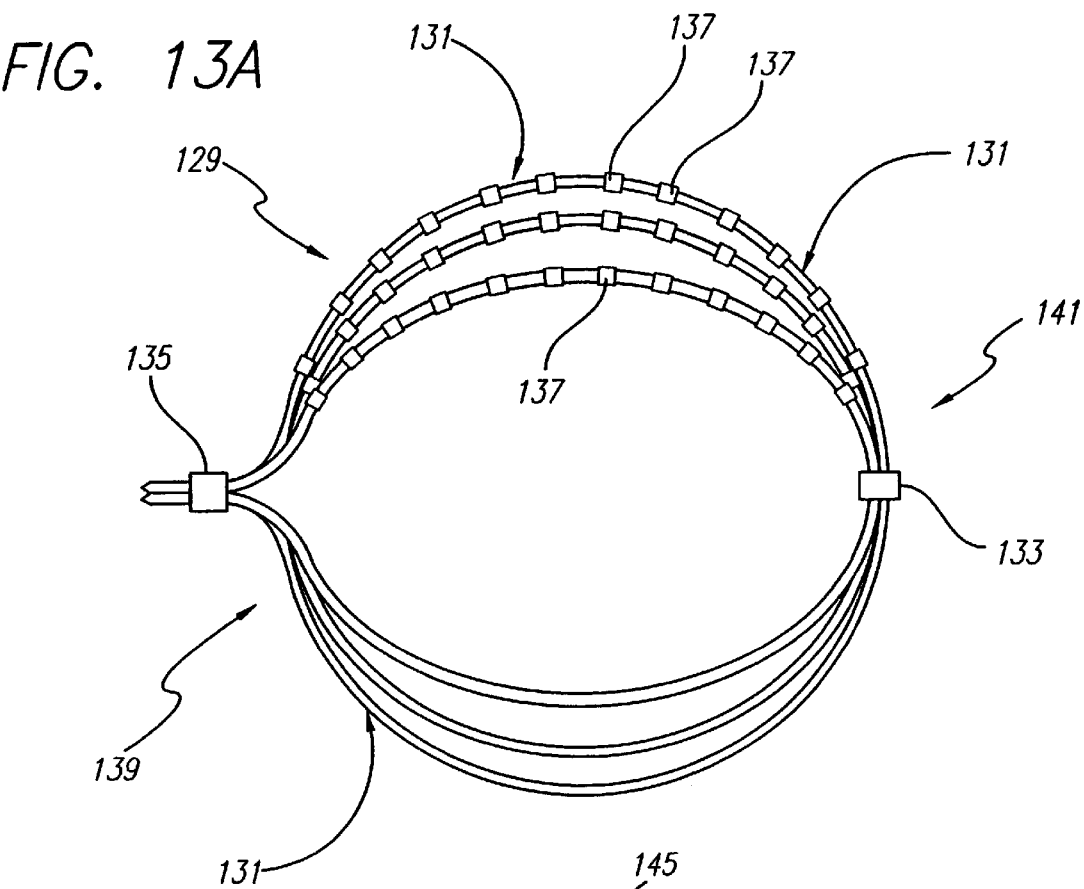
FIG. 13A is a side view of an exemplary asymmetric electrode support device.
Figure 13B:
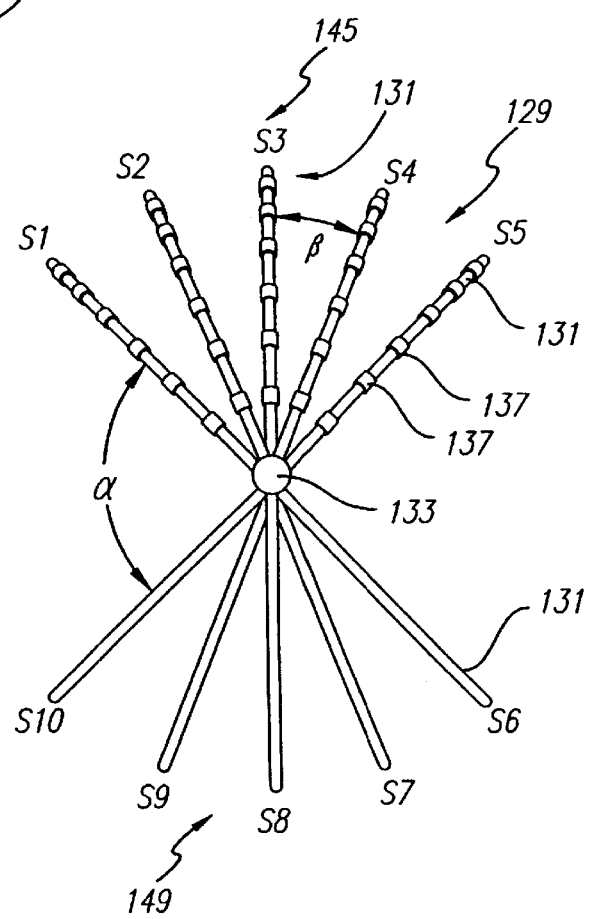
FIG. 13B is an end view of the exemplary asymmetric electrode support device shown in FIG. 13A.

As illustrated in FIG. 39, the exemplary multiple electrode array is a three-dimensional basket structure 358 carried at the distal end 356 of a catheter or surgical probe. The exemplary basket structure includes eight spaced apart spline elements (alphabetically designated A to H in FIG. 39) assembled together by a distal hub 360 and a proximal base 362. Each spline carries eight electrodes which are numerically designated on each spline from the most proximal to the most distal electrode as 1 to 8. The basket structure 358 thus supports a total of sixty-four electrodes. Of course, a greater or lesser number of spline elements and/or electrodes can be present. Each of the electrodes is electrically connected to an individual conductor in a multiple conductor cable 364. The splines can either be arranged symmetrically, as shown in FIG. 39, or asymmetrically as shown in FIGS. 13A and 13B to provide a high density electrode array. A stunning energy source 380 can also be coupled to the electrodes, either through the instrument interface 326 (as shown in solid lines in FIG. 39), or through its own instrument interface 326" (shown in phantom lines in FIG. 39) coupled to the MPU 328.

Instrument 314 may be carried at the distal end 366 of a catheter or surgical probe. In the illustrated embodiment, instrument 314 includes an electrode 368 for sensing electrical activity in tissue, as well as to transmitting energy to stimulate or ablate tissue. The electrode 368 is electrically connected by a cable 370 to the instrument interface 326. A generator 378 for transmitting radio frequency ablation energy can also be coupled to the electrode 368, either through the instrument interface 326 (as shown in solid lines in FIG. 39), or through its own instrument interface 326' (shown in phantom lines in FIG. 39) coupled to the MPU 328. Instrument 316, which may be carried at the distal end of a catheter or surgical probe, includes an imaging device 372 which operates using a visualizing technique such as fluoroscopy, ultrasound, CT, or MRI, to create a real-time image of a body region. A cable 376 conveys signals from the imaging device 372 to the instrument interface 326.

Clinical procedure applications can also be designed and implemented during a procedure using the GUI 346. Based on the images provided by the navigation applications of the electrode support structure, the physician can select the electrodes that will produce the desired area, or areas, of permanently or temporarily unresponsive tissue. The image of the electrode support structure will preferably appear as it does in FIG. 39, i.e. with the spline letters and electrodes numbers visible. The desired electrodes can be selected using the keypad by typing the spline element letters and electrode number. For example, A5, B5 and C5 can be selected to produce an area which spans spline elements, or A3, A4 and A5 can be selected to produce an area which extends along a single spline element. Alternatively, the electrodes may be selected by way of the touch screen or pointing device.

Unless otherwise desired, the pulses will occur in the order that the electrodes are selected. Other information, such as pulse length, time between pulses, pulse magnitude, etc. can also be input via the GUI 346. Instead of delivering energy sequentially, the system can be configured such that a plurality of electrodes transmit energy simultaneously. Such simultaneous transmission may be part of a sequence that includes other electrodes transmitting energy simultaneously or individually. This feature may also be selected on the GUI 346.

Additional information concerning the GUI-based system illustrated in FIGS. 38 and 39 may be found in U.S. application Ser. No. 09/048,629, entitled "Interactive Systems and Methods For Controlling the Use of Diagnostic or Therapeutic Instruments in Interior Body Regions," filed Mar. 26, 1998, and incorporated herein by reference.

II. Additional Devices That May be Used in a Stunning-Modification System

A. Multiple Electrode Stunning-Modification Probes

Probe configurations employing multiple electrodes may also be used to form continuous, elongate areas of modified or temporarily electrically unresponsive (i.e. "stunned") tissue. Such areas may be either straight or curvilinear. Examples of such multiple electrode probes are shown in U.S. Pat. Nos. 5,545,193 and 5,582,609, both of which are incorporated herein by reference.

As shown by way of example in FIG. 6, an exemplary multiple element probe 100 includes a plurality of segmented, generally flexible electrodes 102 carried on a flexible body 104. The flexible body 104 is made of a polymeric, electrically nonconductive material, like polyethylene or polyurethane, and preferably carries within it a resilient bendable wire or spring with attached steering wires so it can be flexed to assume various curvilinear shapes. The electrodes 102 are preferably spaced apart lengths of closely wound, spiral coils made of electrically conducting material, like copper alloy, platinum, or stainless steel. The electrically conducting material can be coated with platinum-iridium or gold to improve its conduction properties, radiopacity and biocompatibility. Instead of a single length of wound wire, one or more of the electrodes 102 may be formed from multiple, counter wound layers of wire. The electrodes may also be formed from a hypotube that is machined into a coil. Additionally, the other electrode structures disclosed in the present specification may also be used in combination with this embodiment.

Alternatively, a ribbon of electrically conductive material can be wrapped about the flexible body 104 to form a flexible electrode. Flexible electrodes may also be applied on the flexible body by coating the body with a conductive material, like platinum-iridium or gold, using conventional coating techniques or an ion beam assisted deposition (IBAD) process. For better adherence, an undercoating of nickel or titanium can be applied.

In another preferred embodiment, and as shown by way of example in FIG. 7, a generally rigid tip electrode 106 may be combined with the generally flexible electrodes. Of course, the tip electrode 106 could be a generally flexible electrode structure made of a closely wound coil or other flexible material. Temperature sensing elements 298, such as thermocouples or thermistors, may also be provided. Temperature sensing is discussed in detail in Section II-F below.

The flexible body 104 can be remotely steered to flex it into a desired shape, or it can possess a preformed shape. In the latter situation, removing a constraint (such as a sheath, not shown), enables the operator to change the segment from straight to curvilinear. The probe body may also be formed from a malleable material, which is especially useful when the probe is part of a surgical probe that is not catheter-based. Such probes are discussed in Section II-D below.

The number of electrodes and the spacing between them, can vary, according to the particular objectives of the therapeutic procedure. For example, the probe shown in FIG. 6 is well suited for creating continuous, elongated lesion patterns (or patterns of tissue modified in other ways) as well as continuous, elongated areas of stunned tissue, provided that the electrodes are adjacently spaced close enough together to create additive heating/stunning effects when energy is transmitted simultaneously to the adjacent electrodes. The additive heating effects between close, adjacent electrodes intensifies the desired effect on the tissue contacted by the electrodes. The additive heating effects occur when the electrodes are operated simultaneously in a bipolar mode between electrodes or when the electrodes are operated simultaneously in a unipolar mode, transmitting energy to an indifferent electrode.

More particularly, when the spacing between the electrodes is equal to or less than about 3 times the smaller of the diameters of the electrodes, the simultaneous emission of energy by the electrodes creates an elongated continuous lesion pattern, or area of stunned tissue, in the contacted tissue area due to the additive effects. Similar effects are obtained when the spacing between the electrodes is equal to or less than about 2 times the longest of the lengths of the electrodes.

To consistently form long, thin, continuous curvilinear lesion patterns or areas of electrically unresponsive tissue, additional spatial relationships among the electrodes must be observed. When the length of each electrode is equal to or less than about 5 times the diameter of the respective electrode, the curvilinear path that the probe takes should create a distance across the contacted tissue area that is greater than about 8 times the smaller of the diameters of the electrodes. The simultaneous application of energy will form a continuous elongate lesion pattern, or area of stunned tissue, that follows the curved periphery contacted by the probe, but does not span across the contacted tissue area. The same effect will be obtained when the length of each electrode is greater than about 5 times the diameter of the respective electrode, and the curvilinear path that support element takes should create a radius of curvature that is greater than about 4 times the smallest the electrode diameters. Of course, the spacing between the electrodes must be such that additive heating effects are created.

Taking the above considerations into account, it has been found that adjacent electrode segments having lengths of less than about 2 mm do not consistently form the desired continuous lesions. Such constraints do not apply to areas of stunned tissue. Techniques to stun tissue to 5 mm to 10 mm in depth using small electrodes are discussed in Section III-B. For ablation purposes, flexible electrode elements can range from 2 mm to 50 mm in length and are preferably 12.5 mm in length with 2 to 3 mm spacing. The diameter of the electrodes and underlying flexible body can vary from about 4 French to about 10 French in catheter-type probes. The tip electrode is preferably from 4 mm to 10 mm in length.

Figure 8:
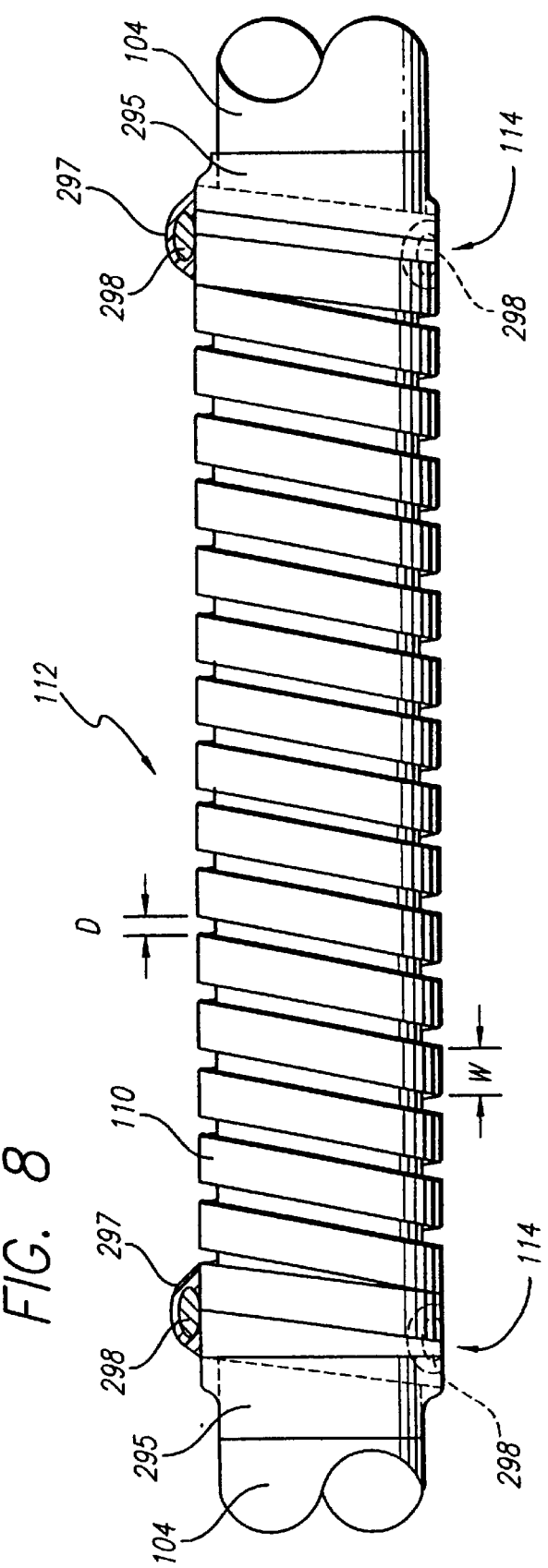
FIG. 8 is a side, partial section view of an exemplary flexible electrode in accordance with one embodiment of a present invention.

The flexibility of the coil electrodes can be increased by spacing the individual coil windings, which increases the ability of the windings to closely conform to irregular anatomical surfaces. The windings of electrodes should be spread apart by a distance that is at least ⅕ of the width of the material that makes up the individual coils. Preferably, the distance is ½ of the width. Referring to FIG. 8, the distance D can also vary along the length of the electrode. Here, the electrode 110 includes a first zone 112 of windings that are spaced apart and two second zones 114 of windings that are closely adjacent to one another. The closely spaced zones provide a support structure for temperature sensing elements, which as discussed below in Section II-F, may be advantageously placed at the longitudinal ends of the electrode. Although the exemplary electrode shown in FIG. 8 has a rectangular cross-section, other configurations, such as a round cross-section, can also be employed.

Power can be supplied to the electrodes individually or, as described above, the power can be simultaneously supplied to more than one or even all of the electrodes. The supply of power to the electrodes can be controlled in the manner disclosed in U.S. Pat. No. 5,545,193.

B. Structures For Positioning Electrodes in a Three-Dimensional Array

Figure 9:
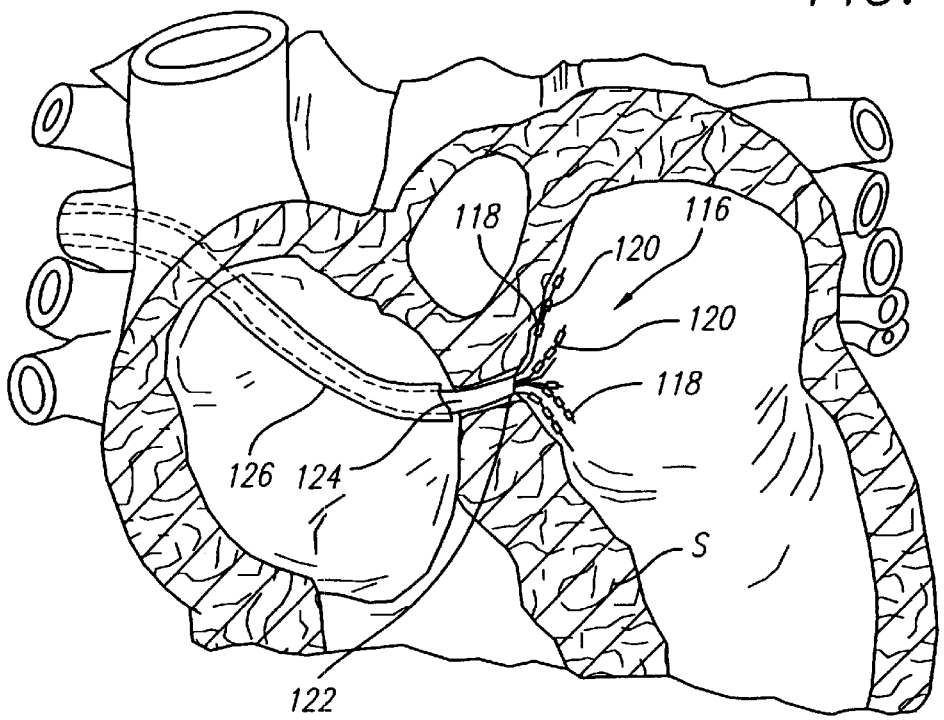
FIG. 9 is a side section view of the interior of the heart with a probe in accordance with one embodiment of a present invention positioned transeptally against the septal wall of the left atrium.
Figure 10:
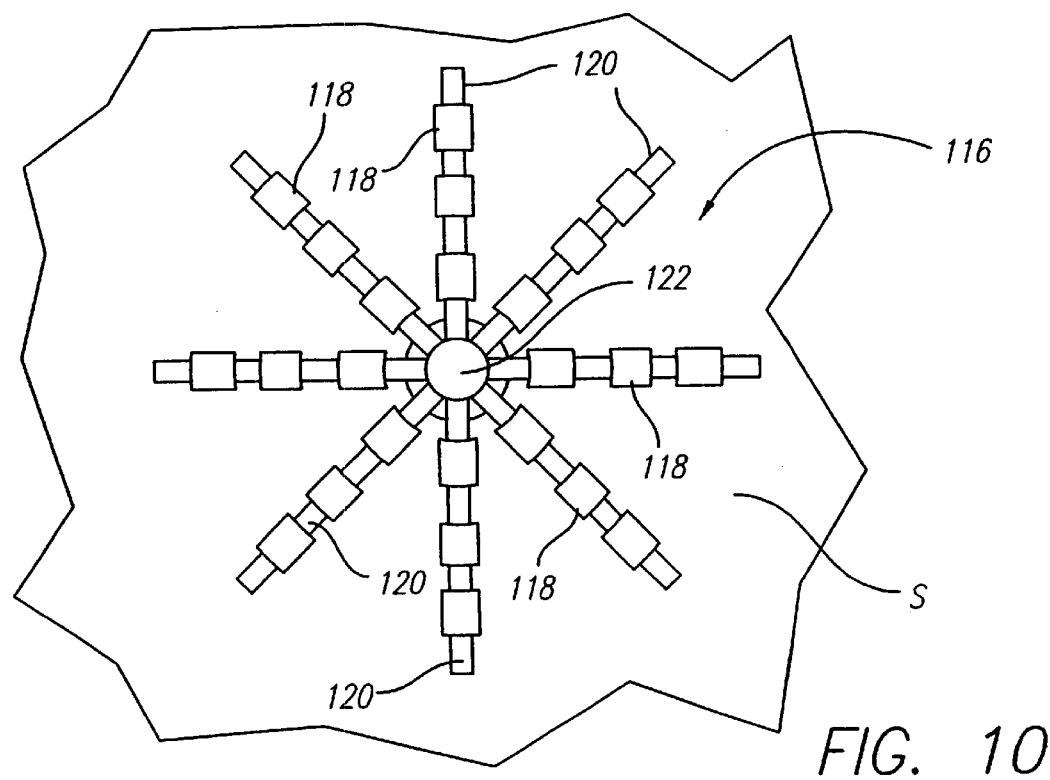
FIG. 10 is an end view of the probe shown in FIG. 9.

There are many instances where it is advantageous to position electrodes in a three-dimensional array. For example, the interatrial septum (identified by the letter S in FIG. 9) has been shown to be a junction for the propagation of atrial fibrillation wavelets. FIGS. 9 and 10 show a device 116 adapted to locate multiple electrodes 118 against a large area of the interatrial septum (S). The device 116 may be used in the same manner as the mapping device 14 shown in FIG. 2. The device may also be used to deliver RF energy to ablate tissue. For example, a subset of the electrodes on the array can be used to simultaneously deliver RF energy to the tissue contacting the electrodes. The subset is chosen based on the geometry and dimensions of the region to be ablated. The region may be a long, continuous line used to treat AFIB, a large circular area used to treat the subendocardial substrates that cause VT, or any other geometry necessary to ablate the substrate(s) causing a particular physiologic event.

Although device 116 is shown as part of a catheter-based device, it may also be employed in a surgical probe that is not catheter-based. Such probes are discussed in Section II-D below.

The device 116 includes an array of spline elements 120 that radiate in a star-like pattern from the distal end 122 of a catheter tube 124 (as the end view in FIG. 10 best shows). Each spline element 120 carries multiple electrodes 118. As shown by way of example in FIG. 9, the catheter tube 124 is deployed through a conventional transeptal sheath 126 into the left atrium. During introduction, the sheath 126 encloses the device 116, maintaining the device in a collapsed condition. Once located in the left atrium, the sheath 126 is pulled back past the septum S, and the spline elements 120, freed of the sheath 126, spring open. The physician pulls the catheter tube 124 back to bring the electrodes 118 into contact against the septal wall within the left atrium.

Turning to FIG. 11, the device 116 can be deployed in the right atrium by introduction through the sheath 126. Retraction of the sheath 126 allows the spline elements 120 to spring open. The physician pushes the catheter tube 124 toward the septum S to place the electrodes 118 into contact against the septal wall within the right atrium.

Another device, generally represented by reference numeral 128 in FIGS. 12A and 12B, includes a high density array of electrodes 130 that can be placed against the septal wall in the right atrium, or against another region anywhere within the heart. The device 128 includes an array of spline elements 132 constrained between a proximal anchor 134 and a distal hub 136. The device 128 is attached to the distal end 138 of a catheter tube 140. However, it may also be employed in a surgical probe that is not catheter-based.

The spline elements 132 carry the electrodes 130 such that they are concentrated in a high density pattern about the distal hub 136. Away from the distal hub 136, the spline elements 132 are free of electrodes 130.

A stylet 142 extends through the catheter tube bore 144 and is attached at its distal end to the distal hub 136. The proximal end of the stylet 142 is attached to a push-pull control mechanism 146 in the catheter tube handle 148. As FIG. 12B shows, pulling back on the mechanism 146 (arrow 147) draws the distal hub 136 toward the proximal anchor 134. The distal region of the spline elements 132 bend and deform outward, to form a generally planar surface 150 radiating about the distal hub 136, on which the electrodes 130 are located. The surface 150 presents the high density pattern of electrodes 130 for intimate surface contact with a large region of heart tissue. The distal hub 136 can be made of an energy transmitting material and serve as an electrode to increase the electrode density.

FIGS. 13A and 13B show another example of a device (or "support assembly") that may be used to position a high density array of electrodes against a bodily structure. The support assembly 129 can be attached to the distal end of a catheter or surgical probe and includes an array of flexible spline elements 131 extending longitudinally between a distal hub 133 and a base 135. The geometry of the assembly 129 is asymmetric in a radial sense. That is, when viewed from distal hub 133, as FIG. 13B shows, the spline elements 131 do not radiate from the main axis at generally equal circumferential intervals. Instead, there are at least some adjacent spline elements 131 that are circumferentially spaced apart more than other adjacent spline elements 131. The largest angle measured between two adjacent spline elements in the assembly (designated angle α in FIG. 13B) preferably exceeds the smallest angle measured between two other adjacent spline elements (designated angle β in FIG. 13B).

Due to the radial asymmetry of the assembly 129, not all the spline elements 131 need to carry electrodes 137. The geometry of the assembly 129 is symmetric in an axial sense. The proximal region 139 and the distal region 141 of each spline are, or capable of being, occupied by electrodes 137.

The exemplary embodiment shown in FIGS. 13A and 13B includes ten spline elements 131, designated S1 to S10. The exemplary asymmetric arrangement includes a first discrete group 145 of five adjacent spline elements 131 (S1 to S5) and a second discrete group 149 (S6 to S10). The groups 145 and 149 are shown to be diametrically arranged, and each group 145 and 149 occupies an arc of about 90°. Within each group, the adjacent spline elements S1 to S5 and S6 to S10 are circumferentially spaced apart in equal intervals of about 22° (which comprises angle β). However, the spline elements S1/S10 and S5/S6, marking the boundaries between the groups 145 and 149, are circumferentially spaced farther apart, at about 90° (which comprises angle α). This non-uniform circumferential spacing of the spline elements 131 exemplifies one type of radially asymmetric structure.

Preferably, the distance between electrode s on different spline elements within a group of spline elements (such as S1 to S5) is equal to the distance between electrodes on a spline element within the group. In other words, the distance between two adjacent electrodes on a spline element is the same as the distance between two adjacent electrodes respectively located on adjacent spline elements. Such an arrangement simplifies the process of forming complex two-dimensional patterns (or large areas) of stunned or permanently modified tissue.

Other types of asymmetric structures for positioning electrodes in a three-dimensional array, such as axially asymmetric structures, are disclosed in U.S. patent application Ser. No. 08/742,569, entitled "Asymmetric Multiple Electrode Support Structures," filed Oct. 28, 1996, which is incorporated herein by reference.

C. Expandable-Collapsible Porous Electrode Structures

Device configurations employing expandable-collapsible porous electrode structures can be used to form areas of modified or temporarily unresponsive tissue that are either large and deep, small and shallow, or large and shallow. Examples of such devices are shown in FIGS. 15–22. These devices may be used in the same manner as the device shown in FIGS. 1 and 3. Additionally, although the devices shown in FIGS. 15–22 are part of catheter-based devices (such as that shown in FIG. 14), the features of the devices may be employed in surgical probes that are not catheter-based. Such probes are discussed in Section II-D below.

Additional information concerning expandable-collapsible porous electrode structures, which are preferably formed from regenerated cellulose, can be found in U.S. patent application Ser. No. 08/631,575, entitled "Tissue Heating and Ablation Systems and Methods Using Porous Electrode Structures," which is incorporated herein by reference.

1. Expandable-Collapsible Porous Electrode Structure Configurations

Figure 14:
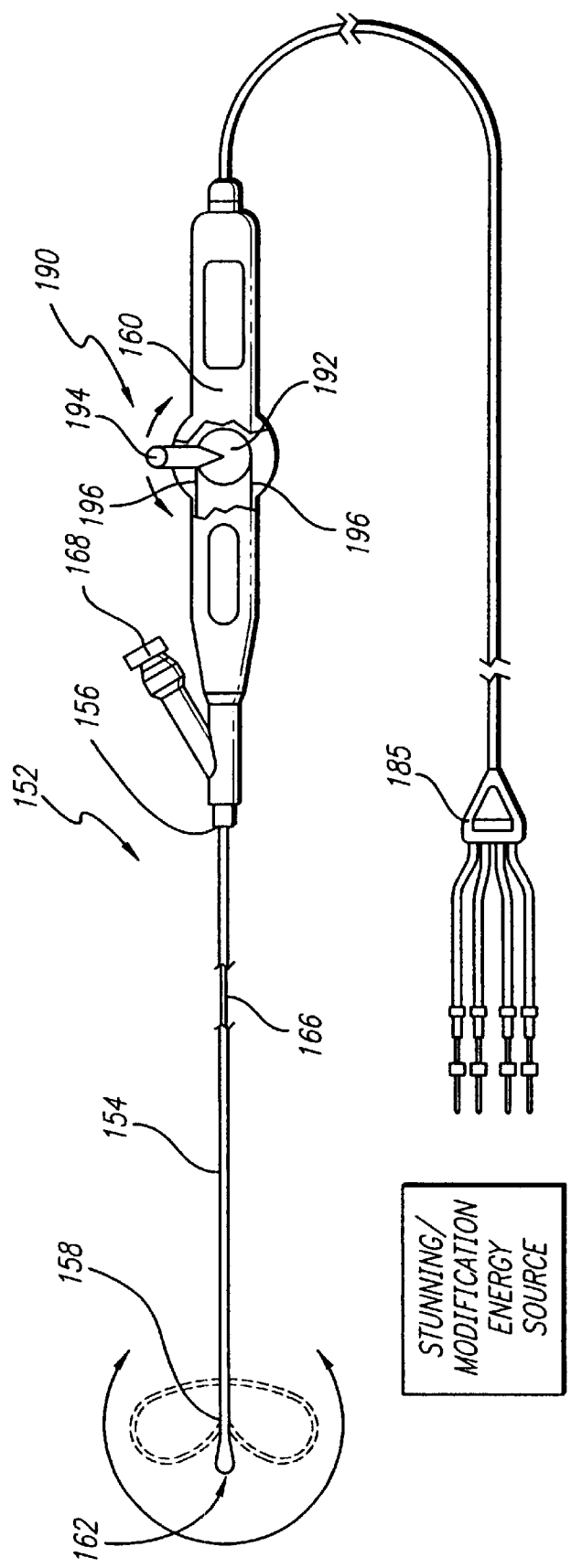
FIG. 14 is a plan view of a system for stunning and/or modifying tissue which includes an expandable porous electrode structure in accordance with one embodiment of a present invention.
Figure 15:
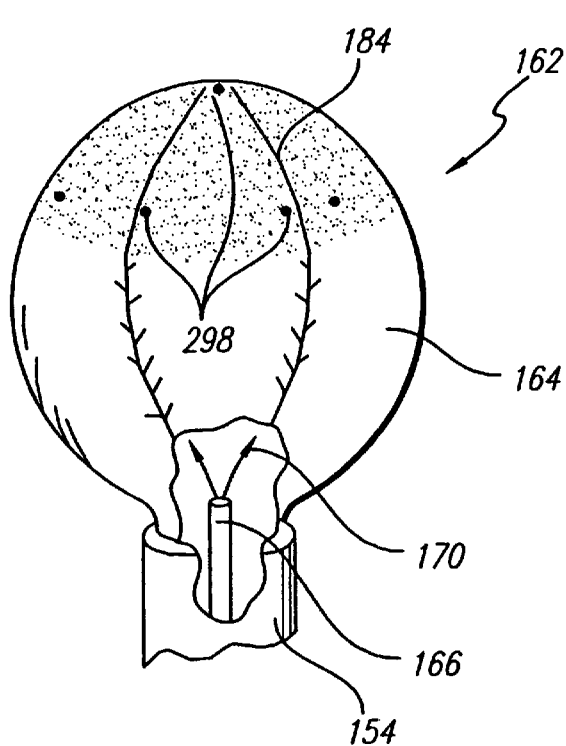
FIG. 15 is side view, with portions broken away, of a porous electrode structure in accordance with one embodiment of a present invention in an expanded state.

FIG. 14 shows a tissue modification-stunning system 152 that includes a flexible catheter tube 154 with a proximal end 156 and a distal end 158. The proximal end 156 carries a handle 160. The distal end 158 carries an electrode structure 162. As shown by way of example in FIGS. 15 and 20, the electrode structure 162 includes an expandable-collapsible body 164. The geometry of the body 164 can be altered between a collapsed geometry (FIG. 16) and an enlarged, or expanded, geometry (FIG. 15). In the illustrated embodiments, liquid pressure is used to inflate and maintain the expandable-collapsible body 164 in the expanded geometry.

Figure 16:
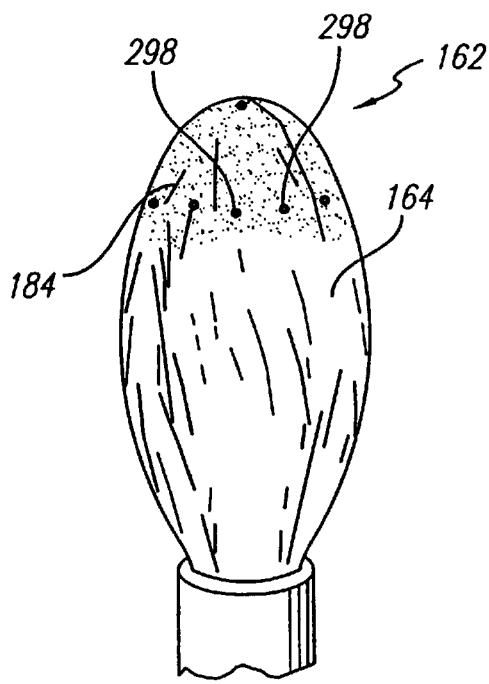
FIG. 16 is side view of the porous electrode structure shown in FIG. 15 in a collapsed state.
Figure 17:
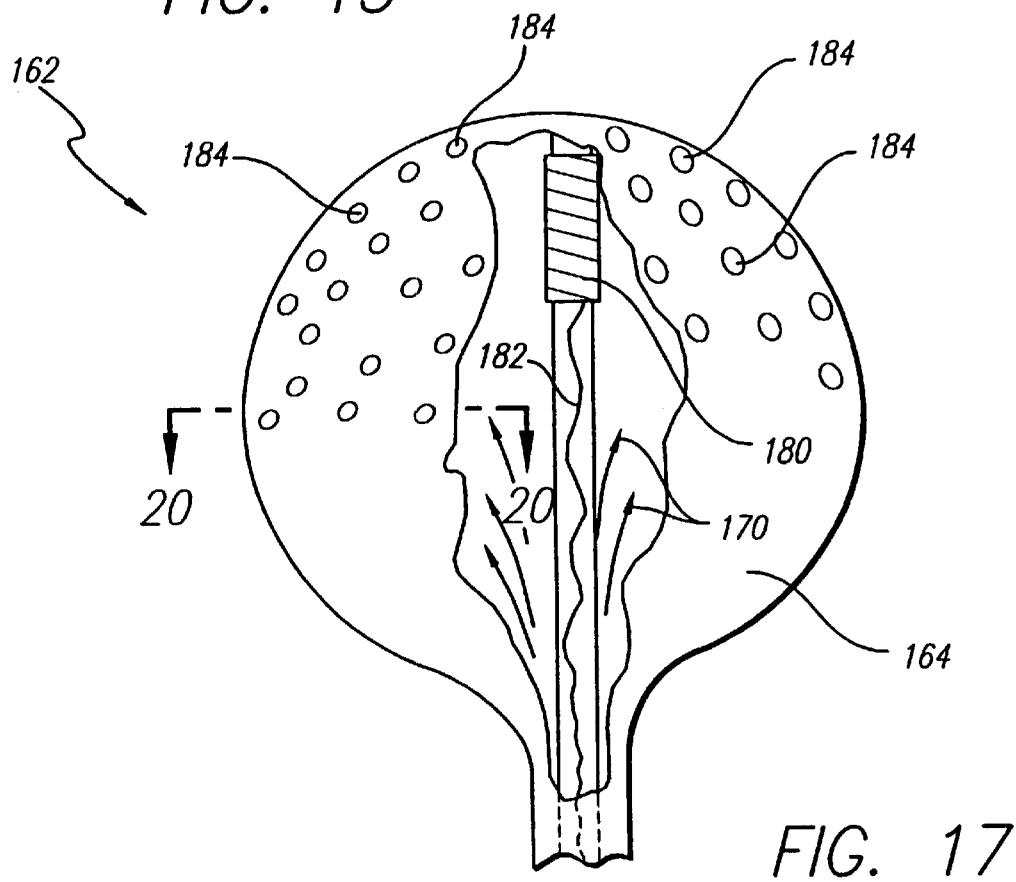
FIG. 17 is an enlarged side view, with portions broken away, of the porous electrode structure shown in FIG. 15.

As illustrated for example in FIGS. 14–16, the catheter tube 154 carries an interior lumen 166 along its length. The distal end of the lumen 166 opens into the hollow interior of the expandable-collapsible body 164. The proximal end of the lumen 166 communicates with a port 168 on the handle 160. The liquid inflation medium 170 is conveyed under positive pressure through the port 168 and into the lumen 166. The liquid medium 170 fills the interior of the expandable-collapsible body 164. The liquid medium 170 exerts interior pressure to urge the expandable-collapsible body 164 from its collapsed geometry to the enlarged geometry.

This characteristic allows the expandable-collapsible body 164 to assume a collapsed, low profile (ideally, less than 8 French diameter, i.e., less than about 0.267 cm) when introduced into the vasculature. Once located in the desired position, the expandable-collapsible body 164 can be urged into a significantly expanded geometry of, for example, approximately 5 mm to 20 mm. Expandable-collapsible bodies with larger profiles may be used in conjunction with probes that are not catheter-based.

As shown by way of example in FIGS. 18 and 19, the structure 162 can include, if desired, a normally open, yet collapsible, interior support structure 172 to apply internal force to augment or replace the force of liquid medium pressure to maintain the body 164 in the expanded geometry. The form of the interior support structure 172 can vary. It can, for example, comprise an assemblage of flexible spline elements 174, as shown in FIG. 18, or an interior porous, interwoven mesh or an open porous foam structure.

The exemplary internally supported expandable-collapsible body 164 is brought to a collapsed geometry, after the removal of the inflation medium, by outside compression applied by an outer sheath 178 (see FIG. 19), which slides along the catheter tube 154. Forward movement of the sheath 178 advances it over the expanded expandable-collapsible body 164. The expandable-collapsible body 164 collapses into its low profile geometry within the sheath 178. Rearward movement of the sheath 178 retracts it away from the expandable-collapsible body 164. Free from the confines of the sheath 178, the interior support structure 172 springs open to return the expandable-collapsible body 164 to its expanded geometry to receive the liquid medium.

As illustrated for example in FIG. 18, the structure 162 further includes an interior electrode 180 formed of an electrically conductive material carried within the interior of the body 164. The material of the interior electrode 180 has both a relatively high electrical conductivity and a relatively high thermal conductivity. Materials possessing these characteristics include gold, platinum, platinum/iridium, among others. Noble metals are preferred. An insulated signal wire 182 is coupled to the electrode 180. The signal wire 182 extends from the electrode 180, through the catheter tube 154, to an external connector 185 on the handle 160. The connector 185 electrically couples the electrode 180 to a radio frequency generator.

In accordance with the exemplary embodiments, the liquid medium 170 used to fill the body 164 includes an electrically conductive liquid. The liquid 170 establishes an electrically conductive path, which conveys radio frequency energy from the electrode 180. In conjunction, the body 164 comprises an electrically non-conductive thermoplastic or elastomeric material that contains pores 184 on at least a portion of its surface. The pores 184 of the body 164 (shown diagrammatically in enlarged form for the purpose of illustration) establishes ionic transport of the tissue stunning or modification energy from the electrode 180, through the electrically conductive medium 170, to tissue outside the body. Preferably, the liquid 170 possesses a low resistivity to decrease ohmic loses, and thus ohmic heating effects, within the body 164. In the illustrated and preferred embodiment, the liquid 170 also serves the additional function as the inflation medium for the body, at least in part.

The composition of the electrically conductive liquid 170 can vary. In the illustrated and preferred embodiment, the liquid 170 comprises a hypertonic saline solution, having a sodium chloride concentration at or near saturation, which is about 20% weight by volume. Hypertonic saline solution has a low resistivity of only about 5 ohm.cm, compared to blood resistivity of about 150 ohm.cm and myocardial tissue resistivity of about 500 ohm.cm. Alternatively, the composition of the electrically conductive liquid medium 170 can comprise a hypertonic potassium chloride solution. This medium, while promoting the desired ionic transfer, requires closer monitoring of rate at which ionic transport occurs through the pores 184, to prevent potassium overload. When hypertonic potassium chloride solution is used, it is preferred keep the ionic transport rate below about 1 mEq/min.

Due largely to mass concentration differentials across the pores 184, ions in the medium 170 will pass into the pores 184, because of concentration differential-driven diffusion. Ion diffusion through the pores 184 will continue as long as a concentration gradient is maintained across the body 164. The ions contained in the pores 184 provide the means to conduct current across the body 164.

When radio frequency energy is conveyed from a generator to the electrode 180, electric current is carried by the ions within the pores 184. The RF currents provided by the ions result in no net diffusion of ions, as would occur if a DC voltage were applied, although the ions do move slightly back and forth during the RF frequency application. This ionic movement (and current flow) in response to the applied RF field does not require perfusion of liquid in the medium 170 through the pores 184. The ions convey radio frequency energy through the pores 184 into tissue to a return electrode, which is typically an external patch electrode (forming a unipolar arrangement). Alternatively, the transmitted energy can pass through tissue to an adjacent electrode (forming a bipolar arrangement). The radio frequency energy may be used to heat tissue (mostly ohmically) to form a lesion, or to render tissue temporarily unresponsive.

The preferred geometry of the expandable-collapsible body is essentially spherical and symmetric, with a distal spherical contour. However, nonsymmetric or nonspherical geometries can be used. For example, the expandable-collapsible body may be formed with a flattened distal contour, which gradually curves or necks inwardly for attachment with the catheter tube. Elongated, cylindrical geometries can also be used.

Figure 21:
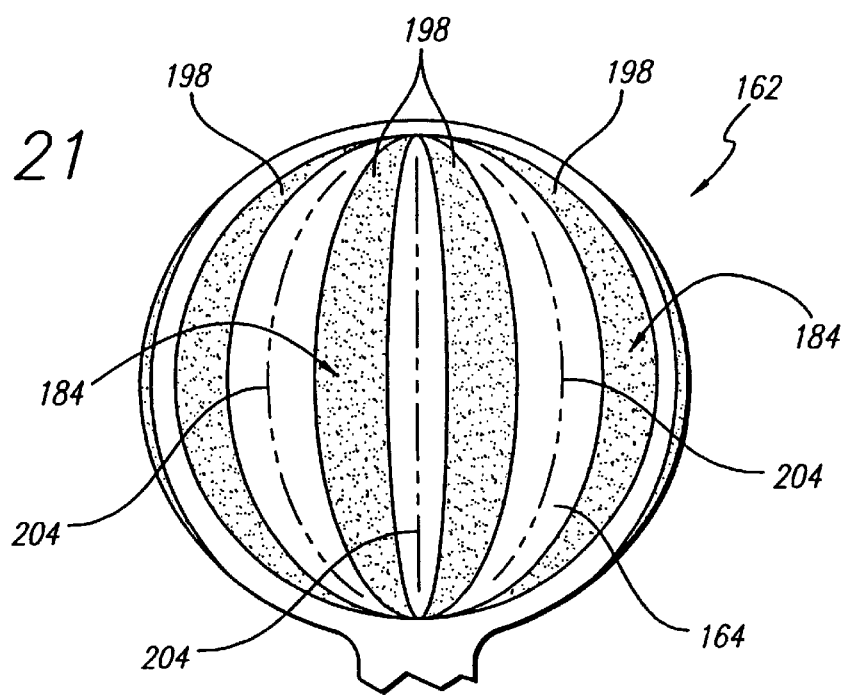
FIG. 21 is a side view of a porous electrode structure in accordance with another embodiment of a present invention.

The exemplary segmented porous zones 198 shown in FIG. 21 are well suited for use in association with folding expandable-collapsible bodies 164. In this arrangement, the regions that are free of pores comprise creased or folding regions 204. It should be appreciated that the foldable body 164 shown in FIG. 21 can also be used for other patterns of porous regions. The creased regions 204 can also be provided with pores, if desired.

2. Pore Patterns

The pattern of pores 184 that define the porous region of the body may vary. As shown by way of example in FIGS. 15 and 16, the region of at least the proximal ⅓ surface of the expandable-collapsible body 164 is free of pores 184 and the porous region is in the form of a continuous cap on the distal ⅓ to ½ of the body. This configuration is useful when it is expected that ablation will occur with the distal region of body 164 oriented in end-on contact with tissue. Alternatively, the electrically conductive porous region may be segmented into separate energy transmission zones arranged in a concentric "bulls eye" pattern about the distal tip of the body 164. When it is expected that tissue stunning or modification will occur with the side region of the body 164 oriented in contact with tissue, the porous region is preferably segmented into axially elongated energy transmission zones, which are circumferentially spaced about the body.

3. Non-porous Conductive and Marking Regions

Figure 22:
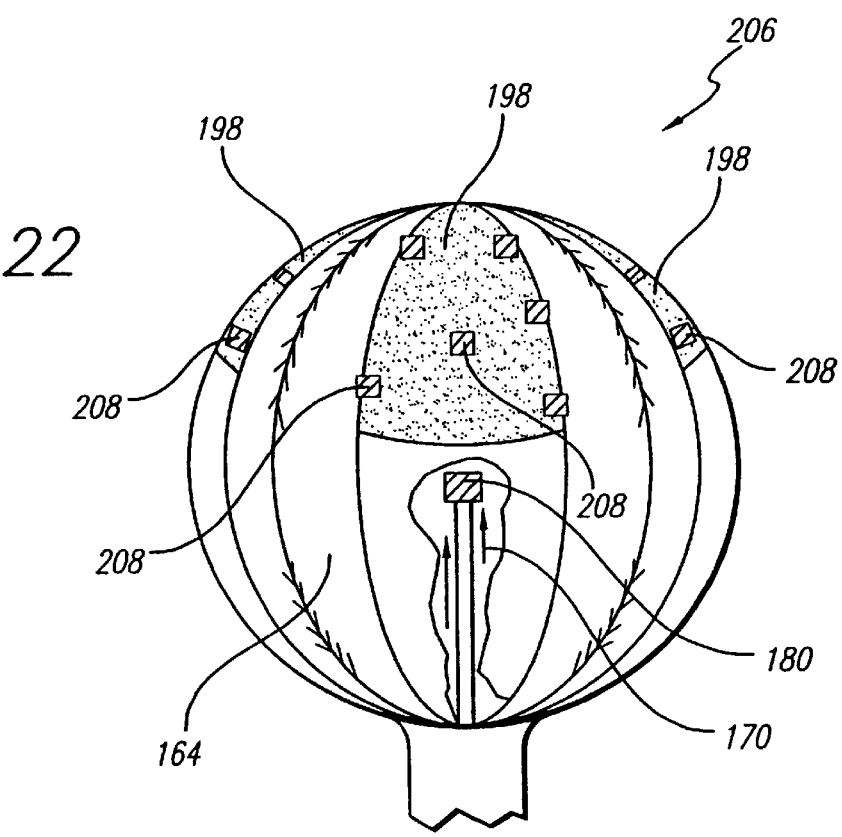
FIG. 22 is side view, with portions broken away, of a porous electrode structure in accordance with still another embodiment of a present invention.

FIG. 22 shows an embodiment of an expandable-collapsible electrode structure 206 that includes one or more nonporous, electrically conductive regions 208 on the surface of the body 164. In the illustrated embodiment, the nonporous conductive regions 208 comprise metal, such as gold, platinum, platinum/iridium, among others, deposited upon the expandable-collapsible body 164 by sputtering, vapor deposition, ion beam deposition, electroplating over a deposited seed layer, or a combination of these processes. Alternatively, the nonporous conductive regions 208 can comprise thin foil affixed to the surface of the body. Still alternatively, the nonporous conductive regions can comprise solid fixtures carried by the porous body 164 at or more locations. Signal wires (not shown) within the body are electrically coupled to the nonporous regions. The signal wires traverse the catheter tube 154 for coupling to the connectors 185 carried by the handle 160.

Various ways for attaching nonporous electrodes 208 and associated signal wires to an expandable-collapsible electrode body 164 are described in U.S. patent application Ser. No. 08/629,363, entitled "Enhanced Electrical Connections for Electrode Structures," which is incorporated herein by reference.

The nonporous regions 208 can be used to sense electrical activity in myocardial tissue. The sensed electrical activity is conveyed to an external controller, which processes the potentials for analysis by the physician. The processing can create a map of electrical potentials or depolarization events for the purpose of locating potential arrhythmia substrates. Once located with the nonporous regions 208, the porous regions 198 can be used to convey radio frequency energy as previously described to ablate the substrates. Alternatively, or in combination with sensing electrical activities, the nonporous regions 208 can be used to convey pacing signals. In this way, the nonporous regions can carry out pace mapping or entrainment mapping.

Opaque markers may be deposited on the interior surface of the body 164 so that the physician can guide the device under fluoroscopy to the targeted site. Any high-atomic weight material is suitable for this purpose. For example, platinum, platinum-iridium. can be used to build the markers. Preferred placements of these markers are at the distal tip and center of the structure 164.

The expandable-collapsible structure 206 shown in FIG. 22 thereby combines the use of "solid" nonporous electrodes 208 with "liquid" or porous electrodes 198. The expandable-collapsible structure makes possible the mapping of myocardial tissue for therapeutic purposes using one electrode function, and the stunning or modification of tissue for therapeutic purposes using a different electrode function.

4. Electrical Resistivity of the Expandable-Collapsible Body

The electrical resistivity of the body 164 has a significant influence on the lesion geometry and controllability. It has been discovered that ablation with devices that have a low-resistivity body 164 (below about 500 ohm.cm) requires more RF power and results in deeper lesions. On the other hand, devices that have a high-resistivity body 164 (at or above about 500 ohm.cm) generate more uniform heating, therefore, improve the controllability of the lesion. Because of the additional heat generated by the increased body resistivity, less RF power is required to reach similar tissue temperatures after the same interval of time. Consequently, lesions generated with high-resistivity bodies 164 usually have smaller depth. The electrical resistivity of the body 164 can be controlled by specifying the pore size of the material, the porosity of the material, and the water adsorption characteristics (hydrophilic versus hydrophobic) of the material. A detailed discussion of these characteristics, as well as the formation of the expandable-collapsible body, can be found in the aforementioned U.S. application Ser. No. 08/631,575, entitled "Tissue heating and Ablation Systems and Methods Using Porous Electrode Structures."

Generally speaking, pore diameters smaller than about 0.1 $\mu$m retain macromolecules, but allow ionic transfer through the pores in response to the applied RF field. With smaller pore diameters, pressure driven liquid perfusion through the pores 184 is less likely to accompany the ionic transport, unless relatively high pressure conditions develop within the body 164. Larger pore diameters (less than 8 $\mu$m) prevent most blood cells from crossing the membrane, but permit passage of ions in response to the applied RF field. With larger pore diameters, pressure driven liquid perfusion, and the attendant transport of macromolecules through the pores 184, is also more likely to occur at normal inflation pressures for the body 164.

Low or essentially no liquid perfusion through the pores 184 is preferred because it limits salt or water overloading, caused by transport of the hypertonic solution into the blood pool and it allows ionic transport to occur without disruption. When undisturbed by attendant liquid perfusion, ionic transport creates a continuous virtual electrode 186 (see FIG. 20) at the body 164-tissue interface. The virtual electrode 186 efficiently transfers RF energy without need for an electrically conductive metal surface.

With respect to porosity, the placement of the pores 184 and the size of the pores 184 determine the porosity of the body 164. The porosity represents the space on the body 164 that does not contain material, or is empty, or is composed of pores 184. Expressed as a percentage, porosity represents the percent volume of the body 164 that is not occupied by the body material. The magnitude of the porosity affects the liquid flow resistance of the body 164, as discussed above. The equivalent electrical resistivity of the body 164 also depends on its porosity. Low-porosity materials have high electrical resistivity, whereas high-porosity materials have low electrical resistivity. For example, a material with 3% porosity, when exposed to 9% hypertonic solution (resistivity of 5 ohm.cm), may have an electrical resistivity comparable to that of blood or tissue (between 150 and 450 ohm.cm).

For a given a porosity value, an array of numerous smaller pores 184 is typically preferred, instead of an array of fewer but larger pores, because the presence of numerous small pores 184 distributes current density so that the current density at each pore 184 is less. With current density lessened, the ionic flow of electrical energy to tissue occurs with minimal diminution due to resistive heat loss. An array of numerous smaller pores 184 is also preferred because it further helps to impose favorably large liquid flow resistance. It is also preferable that the porous body 164 possess consistent pore size and porosity throughout the desired ablation region to avoid localized regions of higher current density and the formation of lesions that are not therapeutic because they do not extend to the desired depth or length.

A dynamic change in resistance across a body 164 can be brought about by changing the diameter of the body 164 made from a porous elastic material, such as silicone. In this arrangement, the elastic body 164 is made porous by drilling pores of the same size in the elastic material when in a relaxed state, creating a given porosity. As the elastic body 164 is inflated, its porosity remains essentially constant, but the wall thickness of the body 164 will decrease. Thus, with increasing diameter of the body 164, the resistance across the body 164 decreases, due to decreasing wall thickness and increasing surface area of the body 164. The desired lesion geometry may be specified according to the geometry of the body 164. This enables use of the same porous body 164 to form small lesions, shallow and wide lesions, or wide and deep lesions, by controlling the geometry of the body 164.

Turning to water absorption characteristics, hydrophilic materials are generally preferable because they possess a greater capacity to provide ionic transfer of RF energy without significant liquid flow through the material.

D. Surgical Probes

As noted above, the present inventions are not limited to catheter-based devices and may be incorporated into surgical probes which are not catheter-based. Such probes allow the physician to directly apply the electrode or other operative element to tissue. Additional information concerning such probes, and uses thereof, may be found in U.S. patent application Ser. No. 08/949,117, entitled "Systems and Methods for Positioning a Diagnostic or Therapeutic Element Within the Body," which is incorporated herein by reference.

Figure 24:
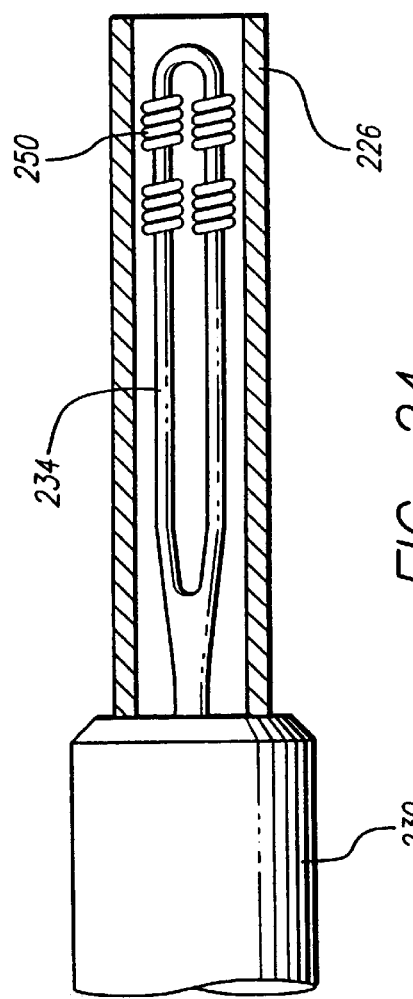
FIG. 24 is a side, partial section view of a portion of the surgical device shown in FIG. 23.
Figure 23:
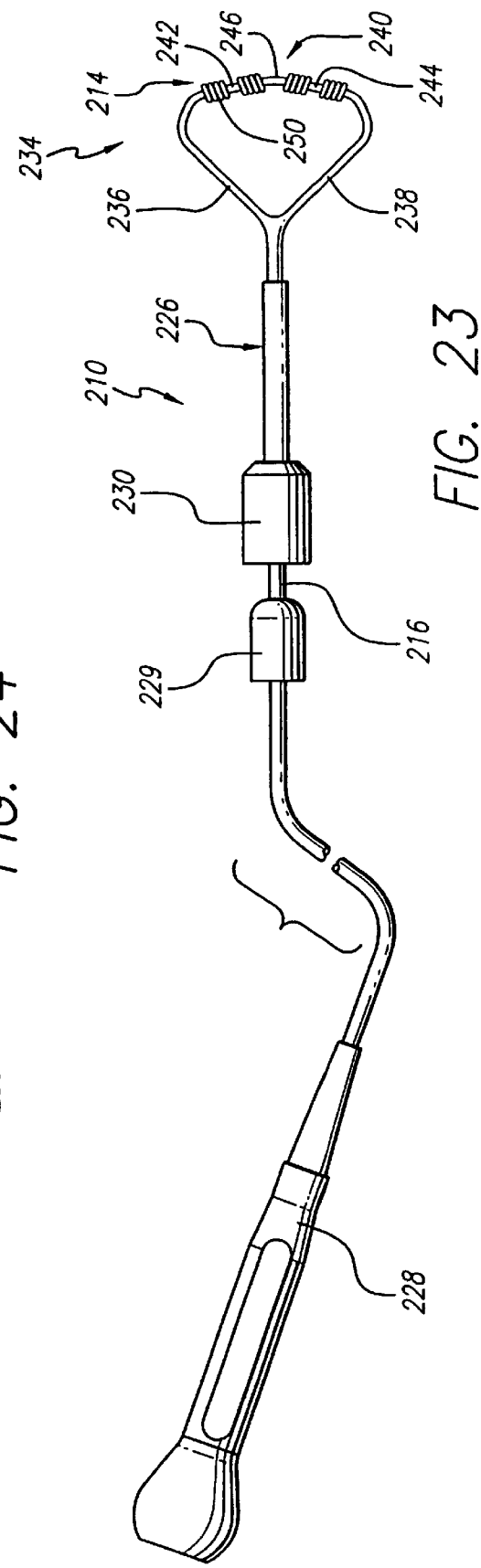
FIG. 23 is a side view of a surgical device for positioning an operative element within a patient in accordance with a preferred embodiment of a present invention.

As illustrated for example in FIGS. 23 and 24, a surgical device (or "probe") 210 for positioning an operative element 214 within a patient includes a relatively short shaft 216 and a substantially triangularly shaped spline assembly 234. The relatively short shaft may be between approximately 4 and 18 inches in length, and is preferably 8 inches in long, while the outer diameter of the shaft is preferably between approximately 6 and 24 French. The operative element preferably consists of a plurality of electrode elements 250. The spline assembly 234 consists of first and second side legs 236 and 238 and a distal leg 240. The distal leg 240, which is preferably non-linear from end to end and approximately 10 to 12 cm in length, includes first and second linear portions 242 and 244 and a bent portion 246 located midway between the ends. This spline configuration provides a spring force against the selected bodily surface during use (such as the atrium wall in a cardiac procedure) and the bend in the distal leg 240 optimizes the contact between the operative element 214 and the selected surface. The surgical probe 210 also includes a first handle 228 and a second handle 229.

The spline assembly 234 will collapse in the manner shown in FIG. 24 when a tubular member 226 (such as a sheath) is advanced thereover and will return to the orientation shown in FIG. 23 when the tubular member is retracted. The tubular member 226 preferably includes a raised gripping surface 230.

During use of the exemplary surgical device shown in FIGS. 23 and 24, the handle 229 is grasped by the physician and force is applied through the shaft 216 and side legs 236 and 238 to the operative element supporting distal leg 240. The shaft 216 and side legs 236 and 238 may be configured such that they collapse and form a semicircle with the distal leg 240 when force is applied to the shaft. Here, the operative element should be appropriately masked in one of the manners described below to limit contact of the operative element to the intended bodily structure.

The exemplary embodiment illustrated in FIGS. 23 and 24 may also be provided without the tubular member 226. Such devices are especially useful in surgical procedures associated with a thoracotomy or a median sternotomy, where the spline assemblies can be easily collapsed and advanced to the desired location, or advanced into the desired location without being collapsed. Here, the spline assemblies can be malleable, if desired, as opposed to simply being bendable.

The spline assemblies illustrated in FIGS. 23 and 24 are preferably made from resilient, inert wire, like nickel titanium (commercially available as Nitinol material) or 17-7 stainless steel. However, resilient injection molded inert plastic can also be used. The wire or molded plastic is covered by suitable biocompatible thermoplastic or elastomeric material such as PEBAX® or pellethane. Preferably, the various portions of the spline assemblies comprises a thin, rectilinear strips of resilient metal or plastic material. Still, other cross-sectional and longitudinal configurations can be used. For example, the spline legs can decrease in cross-sectional area in a distal direction, by varying, e.g., thickness or width or diameter (if round), to provide variable stiffness along its length. Variable stiffness can also be imparted by composition changes in materials or by different material processing techniques. The distal leg 240 may be configured such that the leg is flat at the distal end, but becomes more semicircular in cross-section as the leg becomes more proximal in order to taper the stiffness profile and prevent lateral movement of the spline assembly. The curvature of the spline legs may also be varied and the lateral ends of the distal leg may be reinforced in order to provide more lateral stability.

Figure 26:
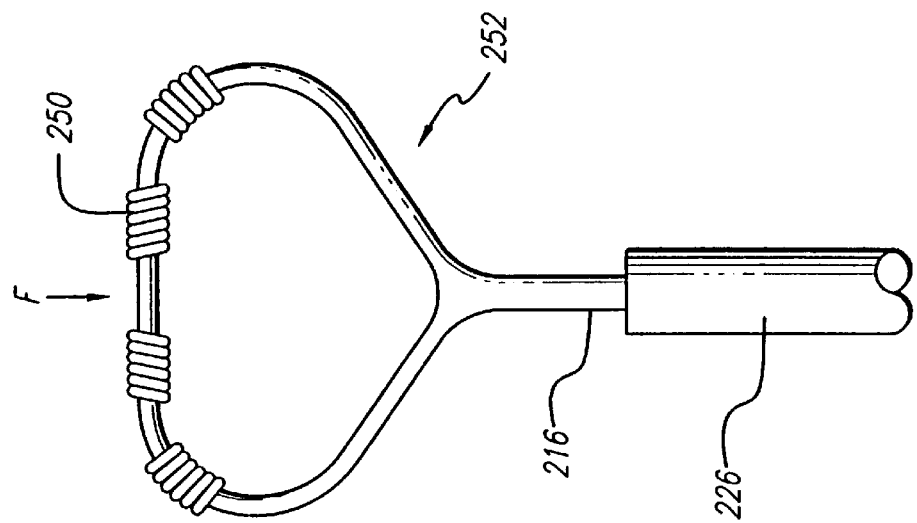
FIGS. 25 and 26 are front views of a spline assembly in accordance with one embodiment of a present invention.
Figure 25:
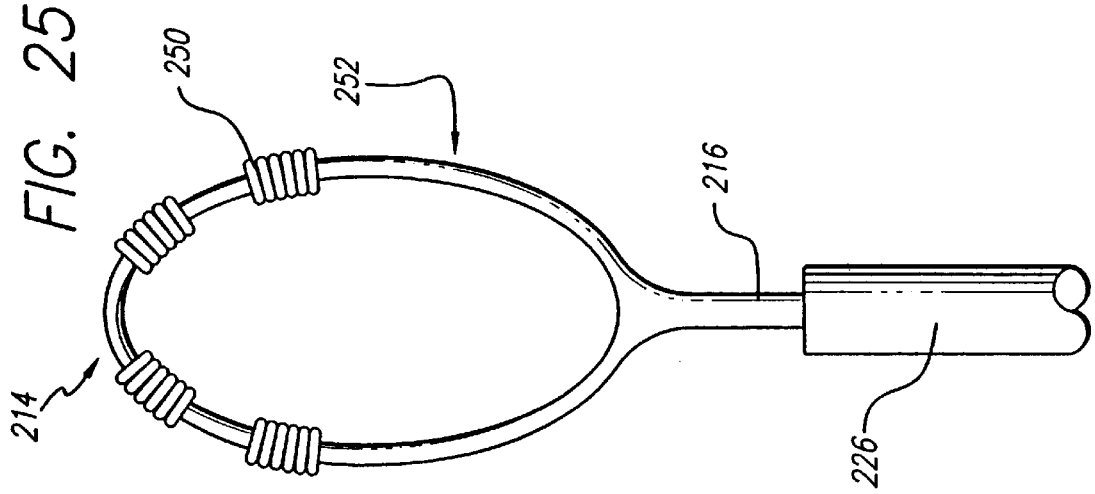

As shown by way of example in FIGS. 25–27, the spline assembly of the probe shown in FIGS. 23 and 24 may be replaced by a curved spline assembly 252. Here, the spline assembly includes a flat, inert wire 254 (preferably formed from Nitinol) that acts as a spring and an outer portion 256 (preferably formed from PEBAX® or pellethane). Viewed in cross-section, the flat wire 254 has a long side and a short side. As such, the spline assembly 252 will deflect in the manner shown in FIG. 26 when "in plane" forces F are applied to the spline assembly. Conversely, the assembly will resist bending when "out of plane" forces are applied. As such, it may be used to form an arcuate lesion during, for example, a procedure where a lesion is formed around the pulmonary vein.

It should be noted here that the wire 254 does not have to be rectangular in cross-section. Other cross-sectional shapes where the length is greater than the width can also be used. The wire 254 can also be made from a malleable material such as partially or fully annealed stainless steel instead of the spring-like material discussed above. The malleable embodiments will enable the operator to form fit the ablation element support structure to irregular anatomical structures.

As shown in FIG. 27, exemplary spline assembly 252 may include first and second steering wires 251a and 251b that are secured to the spring-like flat wire 254 by, for example, welding or adhesive bonding. The proximal ends of the steering wires 251a and 251b are operably connected to a knob 255 on a handle 248 by way of a cam (not shown). The handle 248 also includes provisions for the steering wires 251a and 251b. Rotation of the knob 255 will cause the spline assembly to move side to side. Thus, in addition to simply moving the handle, the physician will be able to move the operative element 214 within the patient by rotating the knob 255. Such movement is useful when the physician is attempting to precisely locate the operative element within the patient and/or control the contact force between the operative element and the tissue surface. This is especially true when the handle and or shaft 216 cannot be moved, due to anatomical or surgical constraints.

In the exemplary embodiment shown in FIG. 27, the steering wires 251a and 251b are both secured at about the midpoint of the flat wire loop. Other configurations are possible depending on the configuration of the loop that is desired after the knob 255 is rotated. For example, one wire could be secured closer to the top of the loop than the other. The shape of the cam may also be varied. More detailed discussions of the use of steering wires, albeit in conventional catheter settings, can be found in commonly assigned U.S. Pat. Nos. 5,195,968, 5,257,451, and 5,582,609, which are incorporated herein by reference.

The shaft 216 is preferably relatively stiff. As used herein the phrase "relatively stiff" means that the shaft (or other structural element) is either rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. A somewhat flexible shaft will bend and spring back when released. However, the force required to bend the shaft must be substantial. Rigid and somewhat flexible shafts are preferably formed from stainless steel, while malleable shafts are formed from annealed stainless steel.

One method of quantifying the flexibility of a shaft, be it shafts in accordance with the present invention or the shafts of conventional catheters, is to look at the deflection of the shaft when one end is fixed in cantilever fashion and a force normal to the longitudinal axis of the shaft is applied somewhere between the ends. Such deflection ($\sigma$) is expressed as follows:

$$\sigma = WX^2(3L-X)/6EI$$

where:

W is the force applied normal to the longitudinal axis of the shaft,

L is the length of the shaft,

X is the distance between the fixed end of the shaft and the applied force,

E is the modulous of elasticity, and

I is the moment of inertia of the shaft.

When the force is applied to the free end of the shaft, deflection can be expressed as follows:

$$\sigma = WL^3/3EI$$

Assuming that W and L are equal when comparing different shafts, the respective E and I values will determine how much the shafts will bend. In other words, the stiffness of a shaft is a function of the product of E and I. This product is referred to herein as the "bending modulus." E is a property of the material that forms the shaft, while I is a function of shaft geometry, wall thickness, etc. Therefore, a shaft formed from relatively soft material can have the same bending modulus as a shaft formed from relatively hard material, if the moment of inertia of the softer shaft is sufficiently greater than that of the harder shaft.

For example, a relatively stiff 2 inch shaft (either malleable or somewhat flexible) would have a bending modulus of at least approximately 1 lb.-in.$^2$. Preferably, a relatively stiff 2 inch shaft will have a bending modulus of between approximately 3 lb.-in.$^2$ and approximately 50 lb.-in.$^2$. By comparison, 2 inch piece of a conventional catheter shaft, which must be flexible enough to travel through veins, typically has bending modulus between approximately 0.1 lb.-in.$^2$ and approximately 0.3 lb.-in.$^2$. It should be noted that the bending modulus ranges discussed here are primarily associated with initial deflection. In other words, the bending modulus ranges are based on the amount of force, applied at and normal to the free of the longitudinal axis of the shaft, that is needed to produce 1 inch of deflection from an at rest (or no deflection) position.

As noted above, the deflection of a shaft depends on the composition of the shaft as well as its moment of inertia. The shaft could be made of elastic material, plastic material, elasto-plastic material or a combination thereof. By designing the shaft 216 to be relatively stiff (and preferably malleable), the surgical tool is better adapted to the constraints encountered during the surgical procedure. The force required to bend a relatively stiff 2 inch long shaft should be in the range of approximately 1.5 lbs. to approximately 12 lbs. By comparison, the force required to bend a 2 inch piece of conventional catheter shaft should be between approximately 0.2 lb. to 0.25 lb. Again, such force values concern the amount of force, applied at and normal to the free of the longitudinal axis of the shaft, that is needed to produce 1 inch of deflection from an at rest (or no deflection) position.

Ductile materials are preferable in many applications because such materials can deform plastically before failure due to fracturing. Materials are classified as either ductile or brittle, based upon the percentage of elongation when the fracture occurs. A material with more than 5 percent elongation prior to fracture is generally considered ductile, while a material with less than 5 percent elongation prior to fracture is generally considered brittle. Material ductility can be based on a comparison of the cross sectional area at fracture relative to the original cross area. This characteristic is not dependent on the elastic properties of the material.

Alternatively, the shaft could be a mechanical component similar to shielded (metal spiral wind jacket) conduit or flexible Loc-Line®, which is a linear set of interlocking ball and socket linkages that can have a center lumen. These would be hinge-like segmented sections linearly assembled to make the shaft.

The exemplary tubular member 226 illustrated in FIGS. 23 and 24 is preferably in the form of a relatively thin cylindrical sheath (e.g., with a wall thickness of about 0.005 inch) and has an outer diameter which is preferably less than 0.180 inch. The sheath material is preferably also lubricious, to reduce friction during movement of the sheath relative to the shaft 216 and spline assembly 234. For example, materials made from polytetrafluoroethylene (PTFE) can be used for the sheath. The distal end of the sheath should be relatively flexible to prevent injury. If necessary, additional stiffness can be imparted to the remaining portion of the sheath by lining the sheath with a braided material coated with PEBAX® material (comprising polyethel block amide related to nylon). Other compositions made from PTFE braided with a stiff outer layer and other lubricious materials can be used.

Alternatively, the tubular member 226 may be relatively stiff and formed from the materials described above with respect to the shaft 216.

As shown by way of example in FIG. 28, a surgical probe 260 in accordance with another embodiment of a present invention includes a relatively stiff shaft 262, a handle 264 and a distal section 266. The shaft 262 consists of a hypotube 268, which is either rigid or relatively stiff, and an outer polymer tubing 270 over the hypotube. A relatively stiff tube, either malleable or somewhat flexible, will preferably have a bending modulus of between approximately 3 lb.-in.$^2$ and approximately 50 lb.-in.$^2$. The handle 264 is similar to the handle 228 discussed above in that it includes a PC board 272 for connecting the operative elements on the distal portion of the probe to a power source. The handle 264 preferably consists of two molded handle halves and is also provided with strain relief element 274. An operative element 214 (here, in the form of a plurality of electrode elements 54) is provided on the distal section 266. This embodiment is particularly useful because it can be easily inserted into the patient through an introducing port such as a trocar.

In those instances where a malleable shaft 262 is desired, the hypotube 268 may be the heat treated malleable hypotube 268 shown in FIGS. 28 and 32. By selectively heat treating certain portions of the hypotube, one section of the hypotube (preferably the distal section) can be made more malleable than the other. This will alleviate any discontinuity between the distal section 266 and the shaft 262 when the distal section is malleable.

The distal section 266 can be either somewhat flexible, in that it will conform to a surface against which it is pressed and then spring back to its original shape when removed from the surface or, as noted above, malleable. A bending modulus of between 3 lb.-in.$^2$ and 50 lb.-n.$^2$ is preferred. As shown by way of example in FIG. 30, a somewhat flexible distal section 266 may include a spring member 280, which is preferably either a solid flat wire spring (as shown) or a three leaf flat wire Nitinol spring, that is connected to the distal end of the hypotube 268. Other spring members, formed from materials such as 17-7 or carpenter's steel, may also be used. A series of lead wires 282 and 284 connect the electrode elements 250 and temperature sensor elements (discussed below), respectively, to the PC board 272. The spring member 280 and leads wires 282 and 284 are enclosed in a flexible body 286, preferably formed from PEBAX® material, polyurethane, or other suitable materials. The spring member 280 may also be pre-stressed so that the distal tip is pre-bent in the manner shown in FIG. 28. Also, an insulating sleeve 281 may be placed between the spring member 280 and the lead wires 282 and 284.

In those instances where a malleable distal section 266 is desired, the spring member 280 may be replaced by a mandrel 287 made of suitably malleable material such as annealed stainless steel or beryllium copper, as illustrated for example in FIG. 31. The mandrel will ideally be fixed to the distal tip of the device (by, for example, soldering, spot welding or adhesives) and run through the shaft into the handle where it will also be fixed to insure good torque transmission and stability of the distal tip. Alternatively, the malleable mandrel may be fixed directly within the distal end of the shaft's hypotube 268 and secured by, for example, soldering, spot welding or adhesives.

The distal section 266 may also be formed by a hypotube that is simply a continuation of the shaft hypotube 268. However, the distal end hypotube can be a separate element connected to the shaft hypotube 268, if it is desired that the distal end hypotube have different stiffness (or bending) properties than the shaft hypotube.

The shaft 262 may be from 4 inches to 18 inches in length and is preferably 6 to 8 inches. The distal section 266 may be from 1 inch to 10 inches in length and is preferably 2 to 3 inches. The length of the electrode elements may range from approximately 4 mm to approximately 20 mm. To facilitate the formation of long continuous lesions or areas or temporarily unresponsive tissue, the distal section 266 preferably includes six electrode elements 250 that are approximately 12 mm in length and approximately 2 to 3 mm apart. This aspect of the inventions is discussed in Section II-A above with reference to FIGS. 6-8. The number and length of the electrode elements 250 can, of course, be varied to suit particular applications.

In accordance with some embodiments of the invention, and as shown by way of example in FIG. 29, the distal section 266 may be provided with a distal (or tip) electrode. The distal electrode 276 may be a solid electrode with a through hole for one or more temperature sensors. Distal electrodes have a variety of applications. For example, a distal electrode may be dragged along an anatomical surface to create a long lesion. The distal electrode may also be used to touch up lesions or areas of unresponsive tissue (straight or curvilinear) created by electrode elements 250 if, for example, the distal section 266 does not exactly conform to the anatomical surface, and to continue lesions and areas of temporarily unresponsive tissue formed by the electrode elements. The distal electrode may also be used to create lesions and areas of temporarily unresponsive tissue in anatomical ridges that are shaped such that the integrity of the surgical device would be compromised if the distal section 266 were bent to conform to the ridge.

In the exemplary embodiments illustrated in FIGS. 23–35, the operative element 214 is made up of a plurality of electrode elements 250 which can serve a variety of different purposes. The operative elements may also be devices such as lumens for chemical ablation, laser arrays, ultrasonic transducers, microwave electrodes, and D.C. hot wires. Such devices may also be incorporated into the other embodiments disclosed in the present specification as appropriate.

In the illustrated embodiments, the principal use of the electrode elements 250 is to transmit electrical energy and, more particularly, RF energy, to modify or stun heart and other tissue. However, the electrode elements 250 can also be used to sense electrical events in heart and other tissue. Alternatively, or in addition, the electrode elements 250 can serve to transmit electrical pulses to measure the impedance of heart tissue, to pace heart tissue, or to assess tissue contact.

The electrode elements 250 are electrically coupled to individual wires (see reference numeral 288 FIG. 35 and reference numeral 282 in FIGS. 30 and 31) to conduct energy to them. The wires are passed in conventional fashion through a lumen extending through one of the spline legs and the shaft 216 into a PC board in the handle, where they are electrically coupled to a connector which is received in a port in the handle. The connector can be used to plug into a source of energy, such as RF ablation or tissue stunning, energy. A plurality of temperature sensing elements (not shown), such as theremocouples or thermistors, may also be provided on the spline assemblies shown herein. Such temperature sensing elements may be located on, under, abutting the edges of, or in between, the electrode elements 250. The temperature sensing elements, and the placement thereof, is discussed in detail below in Section II-F. For temperature control purposes, signals from the temperature sensor elements are transmitted to the source of energy by way of wires (see reference numeral 294 FIG. 35 and reference numeral 284 in FIGS. 30 and 31) which are also connected to the PC board. The respective numbers of wires will, of course, depend on the numbers of sensors and electrodes used in a particular application.

The electrode elements 250, as well as the other electrodes discussed in the present specification, can be assembled in various ways. They can, for example, comprise multiple, generally rigid electrode elements arranged in a spaced apart, segmented relationship. The segmented electrodes can each comprise solid rings of conductive material, like platinum, which makes an interference fit about the annular spline member. Alternatively, the electrode segments can comprise a conductive material, like platinum-iridium or gold, coated upon the device using conventional coating techniques or an ion beam assisted deposition (IBAD) process. The electrodes can also be in the form of helical ribbons.

Alternatively, the electrode elements 250, as well as the other electrodes discussed in the present specification, can comprise spaced apart lengths of closely wound, spiral coils wrapped on the device which form an array of generally flexible electrode elements, as discussed in Section II-A above with reference to FIGS. 6–8. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility.

Electrode elements 250, as well as the other electrodes discussed in the present specification, can be formed with a conductive ink compound that is pad printed onto a non-conductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks.

E. Regenerated Cellulose Coating

Figure 33:
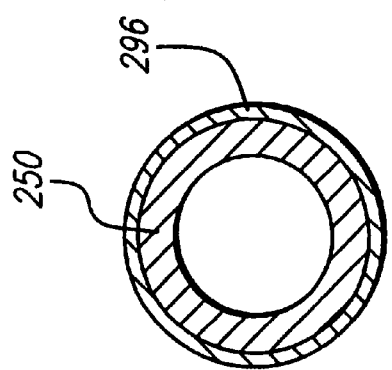
FIG. 33 is a section view showing an electrode coated with regenerated cellulose.

As illustrated for example in FIG. 33, the electrode elements 250, as well as the other electrodes disclosed in the present specification, can include a porous material coating 296, which transmits ablation energy through an electrified ionic medium. For example, as disclosed in U.S. patent application Ser. No. 08/879,343, filed Jun. 20, 1997, entitled "Surface Coatings For Catheters, Direct Contacting Diagnostic and Therapeutic Devices," which is incorporated herein by reference, electrode elements and temperature sensor elements may be coated with regenerated cellulose, hydrogel or plastic having electrically conductive components. With respect to regenerated cellulose, the coating acts as a mechanical barrier between the surgical device components, such as electrodes, preventing ingress of blood cells, infectious agents, such as viruses and bacteria, and large biological molecules such as proteins, while providing electrical contact to the human body. The regenerated cellulose coating also acts as a biocompatible barrier between the device components and the human body, whereby the components can now be made from materials that are somewhat toxic (such as silver or copper).

For applications in which the ablation electrode is in contact with flowing blood as well as tissue, such as when the patient is not on bypass, coating electrodes with regenerated cellulose decreases the effect of convective cooling on the electrode because regenerated cellulose is a poor thermal conductor as compared to metal. Thus, the effect of convective cooling by blood flowing past the regenerated cellulose coated electrodes is diminished. This provides better control for a lesion-generating process because the hottest tissue temperature is closer to the ablation electrode.

Furthermore, the regenerated cellulose coating decreases the edge effects attributed to delivering RF energy to an electrode having a sharp transition between the conductive electrode and insulating material. The current density along the electrode and power density within tissue are more uniform, which reduces the incidence and severity of char and/or coagulum formation. The more uniform current density along the axis of the device also results in a more uniform temperature distribution at the electrode, which decreases the requirement for precise placements of the temperature sensors at the ablation electrodes. Additionally, by coating a device with regenerated cellulose to create the outer surface, less labor-intensive methods of forming electrodes and bonding wires to electrode surfaces can be used.

F. Temperature Control

Temperature sensing elements 298, such as thermistors or thermocouples, may be used in conjunction with any of the electrodes (or other operative elements) disclosed in the present specification. Preferably, the temperature sensing elements 298 are located at the side edges of the electrodes where the electrodes abut the underlying, non-electrically conductive support body, such as the support body 104 shown in FIGS. 6 and 8 or the polymer outer tubing 270 shown in FIG. 28. RF current densities are high at the edges because the edges are regions where electrical conductivity is discontinuous. The resultant rise in current density at the electrode edges generates localized regions of increased power density and, therefore, regions where higher temperatures exist. Nevertheless, the temperature sensing elements may also be located on, under, or in between, the electrode elements in any of the exemplary devices disclosed herein.

In the preferred embodiment illustrated in FIG. 8, a thin strip of electrically insulating material 295 (such as an electrically non-conducting adhesive) is applied to the support body near the closely spaced regions in order to minimize the presence of edge current effects. Additionally, the temperature sensing elements can be mounted either on the inside surface of the electrodes or on the outside surface encapsulated in an epoxy or PTFE coating 297.

As illustrated for example in FIG. 15, the porous electrode structure 162 can carry one or more temperature sensing elements 298. The sensing elements 298 are in thermal conductive contact with the exterior of the electrode structure 162 to sense conditions in tissue outside the structure 162. Temperatures sensed by the temperature sensing elements 298 are processed by a controller. Based upon temperature input, the controller adjusts the time and power level of radio frequency energy transmissions by the electrode 180, to achieve the desired therapeutic objectives. Various ways for attaching temperature sensing elements to an expandable-collapsible electrode body are described in U.S. patent application Ser. No. 08/629,363, entitled "Enhanced Electrical Connections for Electrode Structures," which is incorporated herein by reference.

Additionally, a reference temperature sensing element may be provided. For example, a reference temperature sensing element 299 may be provided on or near the distal tip of the device shown in FIG. 28. The reference temperature sensor may, alternatively, be located in the handle so that room temperature will be used as the reference. Another alternative is to use an electronic circuit to function as the reference temperature sensor. A reference temperature sensor can also be placed on the patient or in the operating room and the physician can simply input the reference temperature into the power control device. It should be noted that the accuracy of the reference temperature sensor is less important in applications where the patient is on bypass because the convective cooling effects of blood flowing past the electrodes is substantially reduced. Also, the present surgical devices provide better tissue contact than conventional catheter-based devices, which provides more accurate temperature monitoring.

Suitable power controllers which control power to an electrode based on a sensed temperature are disclosed in U.S. Pat. Nos. 5,456,682 and 5,582,609, and the aforementioned U.S. patent application Ser. No. 08/949,117, each of which are incorporated herein by reference.

III. Modes of Operation

The operating modes are discussed in the context of cardiac treatment. Nevertheless, and as noted above, the present inventions may be used to treat other types of tissue.

A. Stunning Mode

Figure 5:
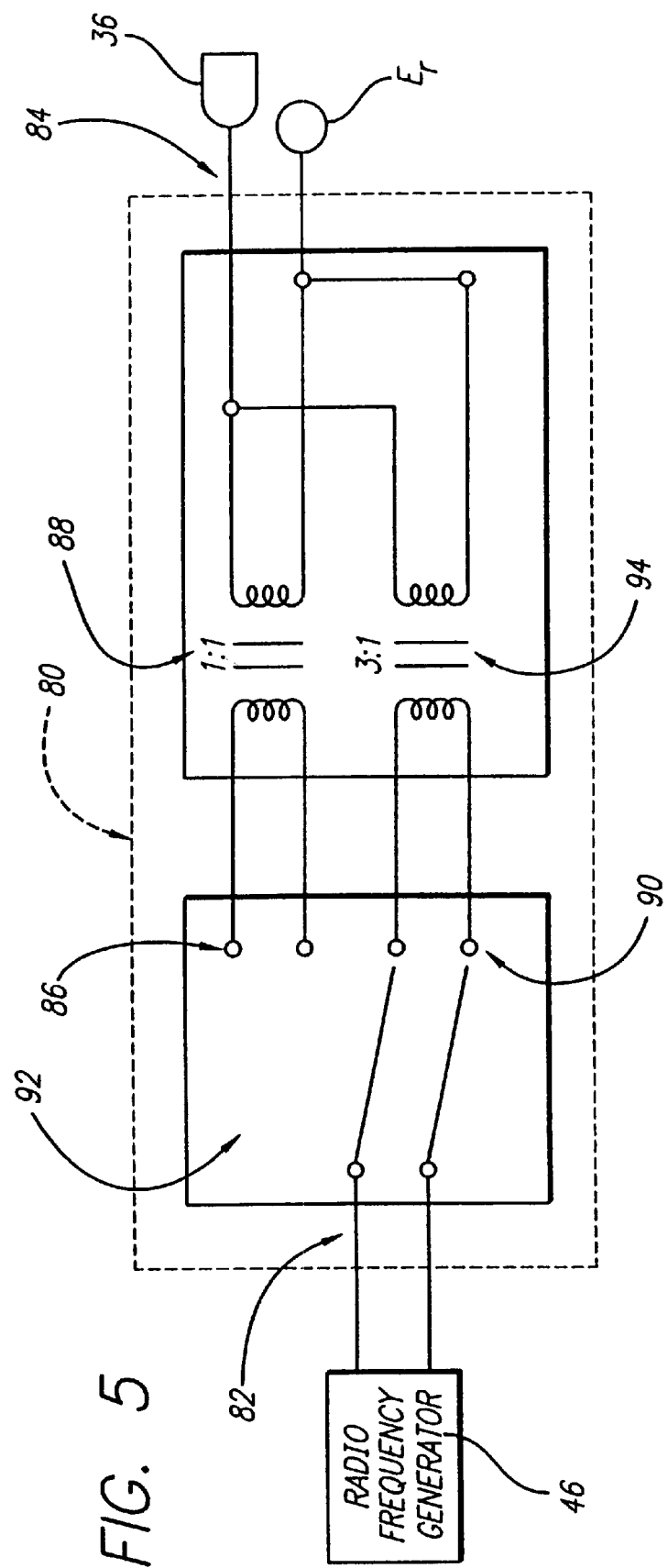
FIG. 5 is a diagrammatic view of a representative switching element in accordance with a preferred embodiment of a present invention that may be used in association with a radio frequency energy generator to switch between a stunning mode and an ablation (or other tissue modification) mode.

Referring to FIGS. 1 and 5, in the stunning (or first) mode, the generator 46 transmits via the switching element 80 one or more high voltage pulses through one or more of the electrode(s) discussed above into a local tissue region contacting or otherwise near the electrode(s). Operation of the switching element 80 is discussed in Section III-C. The electrode configuration may be in the form of a single electrode, a series of spaced electrodes, or an expandable-collapsible electrode structure. Thus, references to "electrode(s)" in this section are references to all of the electrode configurations disclosed in the present specification. Each pulse has a prescribed waveform shape and duration that temporarily "stuns" tissue in the local region without field stimulating tissue in regions farther away from the electrode(s). The temporary stunning creates a likewise temporary electrical conduction block in the local region, rendering the tissue region electrically unresponsive to spontaneous or induced depolarization events. By observing the effect of the local conduction block upon ongoing cardiac events, the physician obtains diagnostic information helpful in locating and confirming potential tissue modification sites.

By purposeful operation of the electrode(s) in the stunning mode in regions where the process controller 32 has assigned a potential ablation site, the system 10 is able to confirm and cross-check the location output of the process controller 32 to verify the location of a potentially efficacious modification site before actually modifying tissue.

Figure 4:
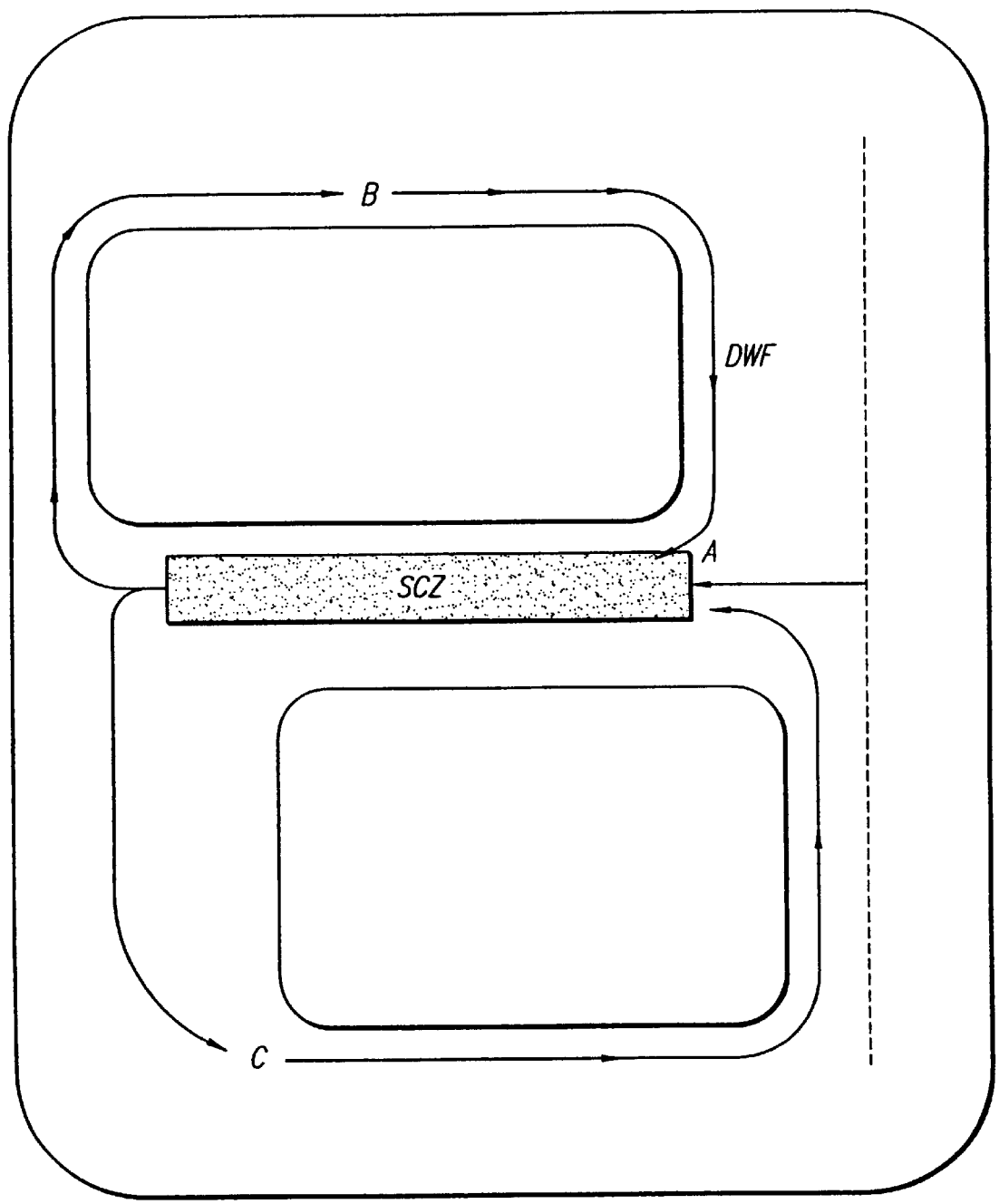
FIG. 4 is a schematic view of a slow conduction zone in myocardial tissue and the circular propagation patterns (called circus motion) it creates.

By way of example, the site appropriate for ablation to cure VT typically constitutes a slow conduction zone, designated SCZ in FIG. 4. Depolarization wave fronts (designated DWF in FIG. 4) entering the slow conduction zone SCZ (at site A in FIG. 4) break into errant, circular propagation patterns (designated B and C in FIG. 4), called "circus motion." The circus motions disrupt the normal depolarization patterns, thereby disrupting the normal contraction of heart tissue to cause the cardiac event.

The event-specific templates T(i) generated by the process controller 32 record these disrupted depolarization patterns. When a pacing signal is applied to a slow conduction zone, the pacing signal gets caught in the same circus motion (i.e., paths B and C in FIG. 4) that triggers the targeted cardiac event. A large proportion of the associated pacing morphologies P(i) at the sensing electrodes E(i) will therefore match the morphologies recorded during the targeted cardiac event.

However, when a pacing signal is applied outside a slow conduction zone, the pacing signal does not get caught in the same circus motion. It propagates free of circus motion to induce a significantly different propagation pattern than the one recorded during the targeted cardiac event. A large proportion of the pacing morphologies P(i) at the sensing electrodes E(i) therefore do not match those recorded during the targeted cardiac event. The difference in propagation patterns between pacing inside and outside a slow conduction zone is particularly pronounced during entrainment pacing. For this reason, entrainment pacing is preferred.

Ablating or otherwise modifying tissue in or close to the slow conduction zone (designated SCZ in FIG. 4) prevents subsequent depolarization. The destroyed tissue is thereby "closed" as a possible path of propagation. Depolarization events bypass the ablated region and no longer become caught in circus motion. In this way, ablation can restore normal heart function in the treatment of VT. In treating VT, the physician therefore places the electrode(s) in a located tissue region where the process controller 32 identifies potential efficacious ablation site. The process controller 32 can include a homing module 70 to aid the physician in guiding the electrode(s) in the located region. Systems and methods for operating the homing module 70 are disclosed in U.S. Pat. No. 5,722,402, and entitled "Systems and Methods for Guiding Movable Electrode Elements Within Multiple Electrode Structures", which is incorporated herein by reference.

With the electrode(s) in position, and before transmitting ablation energy, the physician conditions the generator 46 through the switching element 80 for operation in the stunning mode. The physician also conditions the process controller 32 to induce the cardiac event to be treated, which in this example is VT, unless the cardiac event is otherwise spontaneously occurring. As the cardiac event occurs, the electrode(s) transmits one or more stunning pulses into the tissue region nearest to it. The stunning pulses are timed to the local electrogram to be transmitted when local depolarization occurs.

When the selected pulse stuns tissue laying in the modification-targeted zone, the temporarily rendering of this zone electrically unresponsive will temporarily interrupt the cardiac episode, just as ablation in the zone will permanently stop the cardiac episode. In this respect, stunning serves as a temporary preview of the intended permanent modification.

Should the stunning interrupt the cardiac episode, the physician waits for the temporary conduction block to resolve. Typically, this will take about 30 seconds. When a cardiac episode is interrupted, some arrhythmias will not spontaneously recur immediately after the temporary conduction block has resolved. Here, the episode must be re-induced by conventional programmed stimulation, burst pacing, or other induction methods. After the physician confirms the similarity of the episode to the previous targeted event, the physician may repeat the transmission of one or more stunning pulses to confirm the interruption of the episode. Such a procedure confirms that the substrate which is causing the event, and which is targeted for ablation, is near the electrode(s).

If the episode continues uninterrupted despite the transmission of one or more stunning pulses, the physician knows that the stunned tissue does not include the targeted slow conduction zone. In this circumstance, the physician repositions the electrode(s) to a different location geometrically near to the last stunned site. The physician transmits one or more stunning pulses into tissue at the new site and observes the effect upon the spontaneous or induced episode.

The physician repeats these steps, operating the electrode(s) in the stunning mode in the vicinity of all tissue regions the process controller 34 assigns a potential ablation site, until a site where stunning consistently interrupts the arrhythmia or other condition is located.

When the stunning pulse or pulses repeatedly interrupt the spontaneous or induced episode at a given site, the physician targets the site for ablation. The physician can titrate the volume of tissue comprising the slow conduction zone by varying the amplitude of the stunning pulse and observing the effect. Having targeted the modification site and titrated its volume, the physician, without altering the position of the electrode(s), conditions the generator 46 through the switching element 80 for operation in the modification mode.

As noted above, some cases of VT can be cured with lesions that are somewhat shallower than those typically used to cure VT. In accordance with a present invention, the electrode(s) can be used to stun tissue to a relatively shallow depth. A relatively shallow lesion will be created if the relatively shallow area of unresponsive tissue prevents VT. Otherwise, progressively deeper areas of tissue can be stunned and tested until the VT is eliminated. This way, the depth of the permanently modified tissue will be no greater than necessary.

Another method of identifying appropriate ablation sites in the VT treatment context involves the identification of fractionated electrograms. Fractionated electrograms, in normal sinus rhythm or during VT, are usually seen at sites where ablation or other suitable tissue modification will cure VT. However, they are also seen at sites where ablation does not cure VT. In accordance with a present invention, once fractionated electrogram sites are identified, VT can be induced and stunning voltages applied. Sites that interrupt VT are good candidates for ablation. Nevertheless, testing at a given site should be repeated because spontaneous interruption of VT commonly occurs.

The three-dimensional electrode arrays shown by way of example in FIGS. 2 and 9-13B are particularly useful here. Stunning voltages can be sequentially applied to all sites at which fractionated electrograms are observed. In most patients, fewer than 20 electrode pairs exhibit this morphologic feature. Even if only one stunning pulse were delivered per second to these sites, which is a relatively slow pace, a likely ablation site could be identified in only 20 seconds. A sequential stunning exercise could be performed in less that 20 seconds. If a patient is in VT when the sequence is initiated, one stunning pulse could be delivered for each heart beat. As VT heart rates are usually faster than 180 beats/minute (or 3/sec), all potential ablation sites could be stunned in less than 10 seconds. A record showing which stunning pulse was effective in terminating VT could also be recorded.

Turning to the treatment of AFIB, the physician can create continuous long, thin areas of electrically unresponsive tissue and then perform testing to insure that the permanent modification of the temporarily unresponsive tissue would create the desired therapeutic effect. For example, the physician can perform the portions of a maze procedure that are common to most patients and then observe the surface ECG to determine whether or not AFIB is continuing. In surgical cases, the atrial rhythm can be directly observed, and reading the ECG is not required. If the patient has spontaneously converted to normal sinus rhythm or atrial flutter, then the physician can attempt to reinduce atrial fibrillation by burst pacing the atrium at several different sites. When AFIB persists or is inducible, the physician can use the electrode(s) to temporarily form one or more areas of electrically unresponsive tissue. The testing is then repeated and, if AFIB is no longer present, those areas of tissue can be made permanently electrically unresponsive. If AFIB continues to persist, the physician can continue to render areas both permanently and temporarily unresponsive until a suitable combination of lesions is completed.

In accordance with another aspect of this invention, three-dimensional structures (or baskets) such as those shown in U.S. Pat. No. 5,545,193 can be used to create an entire maze pattern of temporarily electrically unresponsive tissue. If subsequent testing does not show that AFIB has been eliminated, baskets that produce slightly different maze patterns can be employed until the proper pattern is identified. The tissue can then be permanently modified with the same three-dimensional structure that was used to form the partial or complete maze pattern of stunned tissue, provided that the electrodes on the structure are configured for permanent tissue modification. If it is not configured for ablation or other modification, the three dimensional structure can be removed or left in the body to provide a map of the eventual modification sites.

In accordance with another aspect of this invention, three-dimensional structures (or baskets), such as those shown in U.S. Pat. No. 5,647,870, can be used to create an entire maze pattern of temporarily electrically unresponsive tissue. If subsequent testing does not show that AFIB has been eliminated, then a different set of electrodes can be used to create a different maze pattern of temporarily electrically unresponsive tissue and the testing can be repeated. This process can be continued until a proper maze pattern has been identified. Then, with the diagnostic basket still in place, therapeutic catheter(s) or probes can be manipulated to create the maze pattern identified by the diagnostic stunning procedure described above. Guidance of therapeutic catheters to the desired locations near the basket stunning sites can be facilitated using the locating and guiding techniques described in U.S. Pat. No. 5,722,416. Alternatively, the same three-dimensional structures may be used to create therapeutic lesions by employing the high-voltage tissue modification techniques disclosed in Section III-C below.

The effect of a stunning pulse lasts much longer than the amount of time required to deliver the stunning pulse. Typically, the effect lasts more than 100 times longer. Thus, a series of pulses delivered in rapid sequence can be used to create a complex pattern of temporarily unresponsive tissue. Electrode support structures and energy delivery systems such as those shown in FIGS. 10–13B, 38 and 39 may be used to deliver a series of stunning pulses. For example, a sequence of 10 msec stunning pulses, with 10 msecs between each pulse, could be applied with 50 different electrodes in one second to create an entire set of intersecting linear regions of temporarily unresponsive tissue. In other words, a temporary maze pattern that would block transmission of a excitation waveform could be created in one second, or less if the pattern requires fewer electrodes. If the temporary maze pattern successfully terminates AF, then the physician will know that a curative lesion set for the patient may have been identified. Because stunning is reversible, the successful pattern can be repeated to confirm that the proposed pattern will be therapeutic for the patient.

Arrhythmias can appear when there are gaps in the long lesions formed to treat AFIB or when there is a gap between a lesion and the anatomical barrier that the lesion should extend to. For example, during the treatment of AFIB, lesions are created between the pulmonary veins and between the pulmonary veins and the mitral valve annulus. The inventors herein have determined that gaps in lesions at the mitral valve annulus are common because the myocardium is thicker at this site and because anatomical structures at the mitral valve annulus make it difficult to obtain tissue contact that will result in a continuous lesion, even in patients with easily induced AF or those in chronic AF.

These gaps are very difficult to locate and treat using conventional roving catheter or probe technology partly because the process of defining the location and extent of the rotor circuit is time consuming and laborious. With such technologies, location of the appropriate ablation site commonly requires 2–4 hours of procedure time. Use of a three-dimensional structure (or basket), such as those shown in U.S. Pat. No. 5,547,870, can dramatically reduce the time required to identify a potential ablation site. However, even with this technology, the mapping information does not provide a definitive site for curing the arrhythmia using tissue modification methods.

The electrical stunning techniques described herein provide an effective method of determining whether ablation at a potential site will cure an arrhythmia. If the flutter is eliminated, the suspected gap areas can be rendered permanently electrically unresponsive by ablation or other suitable means.

In certain situations, an alternative strategy whereby tissue is stunned at known anatomical positions is more efficient. The approximate positions of the areas of electrically unresponsive tissue to be created by the therapeutic catheters can be identified with fluoroscopic or ultrasonic imaging. Stunning pulses are then applied to sites that are known to be probable gap locations based on prior experience. For example, unwanted gaps between a line of block and an anatomical barrier are somewhat common, especially at the mitral valve, tricuspid annulus and pulmonary veins. If a stunning pulse applied to the suspected gap area eliminates the flutter, then the area can be permanently rendered electrically unresponsive by ablation or other suitable means.

In an alternative embodiment, the physician stuns the selected local region and then operates the process controller 34 to induce the desired cardiac event. In this embodiment, the physician observes whether stunning the selected local region suppresses the undesired cardiac event. When stunning a given selected region consistently suppresses the undesired cardiac event, which in the absence of stunning occurs, the physician targets the given region for ablation or other modification.

It should be appreciated that the use of high voltage stunning can be carried out in association with conventional electrocardiogram analysis, without the use of a multiple electrode mapping probe described above. The use of a multiple electrode mapping probe is preferred, as it provides a more accurate indication where stunning should be applied than conventional techniques.

It should also be appreciated that the stunning pulses can alternatively comprise DC or AC energy transmitted by the electrode 36 from a source separate from the generator 46.

B. Power Considerations Associated With Stunning

The waveform pattern, duration, and amplitude of the stunning pulses effective to stun an efficacious volume of myocardium can be empirically determined by in vivo or in vitro tests and/or computer modeling.

The character of the stunning pulse is expressed in terms of its waveform shape, its duration, and its amplitude. The duration and amplitude are selected so as to create a temporary electrical conduction block without damage to the tissue. For the purpose of this Specification, the term "temporary" refers to a time period less than about five minutes.

The duration of the pulse can vary from microseconds up to several seconds, depending upon the waveform (DC or AC) of the pulse, amplitude of the pulse, and the electrode configuration. There is a strength-duration relationship between pulse duration and amplitude, with short pulse patterns requiring somewhat higher voltages to stun, but not kill, tissue. Short pulse durations not exceeding about 100 milliseconds are preferred. Also, because the purpose of stunning is to simulate the effect of permanent tissue modification, it is important to note that shallow lesions (about 5 mm) are effective in treating AFIB and some other arrhythmias, while larger and deeper lesions (up to and exceeding 1 cm) are generally required when treating VT.

The pulse amplitude, $S_{AMP}$, selected depends upon the voltage gradient, the configuration of the electrode(s), the depth of tissue penetration desired, and the impedance of the system, expressed as follows:

$$S_{AMP} = \left(\frac{S_V}{L}\right) \times \left(\frac{A}{\rho}\right) \times R$$

where:

$S_V/L$ represents the local voltage gradient,

A is the cross-sectional area of the voltage gradient, $\rho$ is the resistivity of the tissue to be stunned, and R is the impedance of the delivery system and electrode that transmits the pulse.

With respect to the local voltage gradient $S_V/L$, as a benchmark, DC voltage gradients of between about 70 volts/cm and 200 volts/cm that are about 10 milliseconds in duration, when delivered by defibrillation catheters, have been shown to temporarily stun chicken embryo myocardial tissue in vitro, rendering it electrically unresponsive. The stunning in these instances extends about 1 cm from the electrode when a 800 volt (DC) shock is delivered. Higher voltage gradients increase the risk of killing myocardial tissue. The duration of unresponsiveness of stunned tissue varies from 1 to 60 seconds and more, depending upon the local voltage gradient. The effective volume of the local conduction block shrinks with time, as tissue exposed to lower voltage gradients at the edges of the stunned tissue volume recovers faster than tissue exposed to higher voltage gradients at the center of the stunned tissue volume. See, e.g. Jones et al., "Microlesion Formation in Myocardial Cells by High Intensity Electric Field Stimulation," the American Physiological Society (1987), pp. H480–H486; Jones et al., "Determination of Safety Factor for Defibrillator Waveforms in Cultured Cell Hearts," the American Physiological Society (1982), pp. H662–H670. Based upon the foregoing in vitro benchmarks, it is believed that a nominal voltage gradient of about 125 volts/cm can be safely selected. Voltage gradients about four times higher, i.e. 500 volts/cm, are believed to kill about 50% of the cells and unintentional application of such voltage gradients should be avoided.

The cross-sectional area A of the voltage gradient depends upon the shape of the electrode(s). For example, the portions of the electrode 36 shown in FIGS. 1 and 3 and the porous electrodes shown in FIGS. 15–20 and 22 in contact with tissue are assumed to be a spherical section with a radius r measured from the center of the electrode body to the tissue where stunning occurs. The spherical model is also useful for the relatively small electrodes that are sometimes used in the exemplary three-dimensional arrays shown in FIGS. 2 and 9-13B. For example, for r=1 cm, the quantity A (assumed to be the surface area of a ½ of a sphere with radius r of 1 cm) is $2\pi r^2$ or about 6 cm². This assumption can be made with respect to a porous electrode when the distal half is non-conductive.

The coil electrodes shown in FIGS. 6–8 and 23–28 form continuous cylindrically shaped transmission areas. The quantity A of the generally cylindrical coil is $2\pi rl$ (where l is the length of the coil). When the patient is on bypass, and one half of the electrode is exposed to air, the quantity A is $\pi rl$.

Turning to the resistivity $\rho$ of the tissue to be stunned, for an electrode exposed to both blood and myocardial tissue, $\rho$ is believed to be about 200 ohm.cm, while the resistivity of myocardial tissue when blood is not present (such as when the patient is on bypass) is about 400 to 500 ohm.cm.

It is also noteworthy that larger electrodes (greater than about 4 mm) require somewhat lower voltages to achieve the same stunning effect. This is primarily because of decreased losses in near-field tissue because of decreased current densities at the surface of larger electrodes.

The waveform shape and period is selected so that the pulse will not field stimulate tissue at sites distant from the electrode(s). A stunning pulse that causes far field stimulation can cardiovert (i.e., stop) the entire cardiac event for reasons other than a temporary, localized conduction block. Cardioversion therefore can overshadow the desired, more discrete specificity of the stunning effect. The character of the stunning pulse is selected to induce only a temporary conduction block in a discrete, relatively small volume of tissue generally equal to the volume of tissue to be ablated or otherwise modified. A biphasic or uniphasic square wave (DC) transmitted for a short duration (about 100 microseconds) will achieve this effect. A sinusoidal (AC) signal at frequencies above about 10 kHz for durations of about 10 milliseconds will also achieve this effect. The DC pulse or short duration AC signal can be transmitted either unipolar (as the illustrated embodiment shows) or in a bipolar mode.

Based upon the foregoing considerations, and assuming that blood is present so that the effective tissue resistivity is 200 ohm.cm, for an electrode such as that shown in FIGS. 1 and 3 with a diameter of about 4 mm, a radio frequency pulse having an amplitude of about 100 volts (at 500 kHz) and a duration of about 10 milliseconds will stun tissue to a depth of about 5 mm (which is sufficient when treating AFIB and supra-ventricular tachycardia (SVT)). With the same 4 mm electrode, a larger pulse amplitude of about 400 volts (at 500 kHz) at a duration of about 10 milliseconds will stun tissue to a deeper depth of about 1 cm (which is required for treating VT). Thus, taking typical electrode configurations and typical ranges of stunning depths into account, the radio frequency pulse amplitude (at 500 kHz) will range from about 100 volts up to about 800 volts (at 500 kHz), with durations less than about 100 milliseconds.

When the patient is on bypass with no blood present (and the tissue resistivity is about 400 to 500 ohm-cm), a radio frequency pulse having an amplitude of about 50 volts (at 500 kHz) and a duration of about 10 milliseconds will stun tissue to a depth of about 5 mm, and a pulse having an amplitude of about 250 volts (at 500 kHz) and a duration of about 10 milliseconds will stun tissue to a depth of about 1 cm.

Turning to porous electrode structures, and assuming that the distal half of the porous electrode is non-conductive so that current flows primarily into the myocardial tissue and not into blood, whether the patient is on bypass or not, the tissue resistivity will be about 400 to 500 ohm-cm. For a 1.2 cm balloon, stunning tissue to a depth of 5 mm requires a radio frequency pulse having an amplitude of about 100 volts (at 500 kHz) and a duration of about 10 milliseconds, further assuming a system impedance of 70 ohms. At 500 kHz, stunning tissue to a depth of 1 cm will require a pulse of about 200 volts for about 10 milliseconds, stunning tissue to a depth of 1.5 cm requires a pulse of about 360 volts for about 10 milliseconds, and stunning tissue to a 2 cm depth will require a pulse of about 600 volts for about 10 milliseconds. The 600 volt pulse may, however, kill 1-2 mm of tissue near the electrode because of the very large voltage gradients at the surface of the porous electrode.

The power requirement calculations for the electrodes shown in FIGS. 6–8 and 23–28, which are especially useful in AFIB treatment, have been made with the following assumptions: the modification/stunning electrodes are 12.5 mm long coils, the coils are exposed to blood (effective tissue resistivity of 200 ohm.cm), the current spreads in cylindrical manner, the cylinder is 2 cm long (to compensate for not including the ends of the cylinder in the model), and the system impedance is 70 ohms when stunning through a single electrode. With a cylindrical electrode, the voltage gradient drops as a function of 1/r. When the tissue surface is about 2 mm from the center of the coil, a radio frequency pulse having an amplitude of about 300 volts (500 kHz) and a duration of about 10 milliseconds will to stun tissue to a depth of 3 mm. Stunning to a depth of 8 mm requires an amplitude of about 600 volts (500 kHz) and duration of about 10 milliseconds. Beyond 8 mm, the cylindrical model will not produce accurate approximations of the geometry of the system, and voltage requirements rise rapidly.

The three-dimensional electrode supporting structures shown in FIGS. 2 and 9–13B are also used to stun tissue. Depending upon electrode size and spacing, they are generally capable of creating lines of temporarily unresponsive tissue along a spline or between splines. When such structures are incorporated into a catheter-based device, the wires to the electrodes are typically only about 42 gauge. Although size limits their ability to carry high currents for extended periods of time, the wires are capable of carrying the 4 amperes of current required to stun tissue for at least 10 ms.

The current requirements for the electrodes in the three dimensional arrays are about the same as that required for the conventional 4 mm electrode discussed above with reference to FIGS. 1 and 3, but the driving voltage requirements are higher due to the higher system impedance. The higher system impedance is caused by the resistance of the wires connecting the connector pins to the electrodes (about 20 ohms) and the high current density at the electrodes. Assuming that tissue resistivity is 200 ohm-cm (the combined resistivity of tissue and blood in a non-bypass environment), a system impedance of about 200 ohms (we measured this in animals), and the aforementioned spherical model, a radio frequency pulse having an amplitude of about 800 volts (500 kHz) and a duration of about 10 milliseconds will to stun tissue to a depth of 1 cm. A pulse with an amplitude of about 150 volts and a duration of about 10 milliseconds will stun tissue to a depth of 5 mm. It should be noted, however, that the destruction of about 1 mm³ of tissue is almost unavoidable using presently available electrodes.

Three-dimensional arrays, such as those discussed in Section II-B, can be used in conjunction with surgical probes, preferably when the patient is on bypass. The stunning voltage requirements for electrodes in the three-dimensional arrays are much lower when patients are on bypass. No blood is present and the effective tissue resistivity is about 400–500 ohm-cm. The effective area of the voltage gradient is also about one-half of the voltage gradient area when blood is present because virtually no current flows in air. The system impedance is, however, increased to about 350 ohms. The net effect is to decrease, by about a factor of two, the amplitude of the voltage pulse required to stun tissue to a given depth. For example, only about 400 volts would be required to stun tissue to a depth of 1 cm. In addition, the dimensional constraints placed on a device that must be introduced percutaneously are considerably relaxed for arrays that are inserted into patients on bypass. Electrode area could easily be doubled for devices designed for introduction into heart chambers via an atriaotomy during cardiopulmonary bypass. Use of these larger electrodes would decrease the amplitude of the voltage stunning pulse by an additional factor of one and one-half, primarily because the system impedance is lower with the larger electrodes.

It should be appreciated that the relatively high power required to stun tissue will also heat the tissue. As compared to the time required to redistribute heat in the body, stunning pulses are very short in duration. Thus, a stunning pulse causes an increase in the temperature of the affected tissue based solely on the energy dissipated in the affected tissue during the stunning pulse. Typically, a stunning pulse will directly heat 2 or more grams of tissue. The maximum power required will be up to about 12,000 Watts, with a pulse duration of 1–10 msec. Therefore, the stunning pulse could deliver as much as 120 Joules to the tissue (or about 30 calories), which would immediately raise the temperature of the affected tissue to about 50° C.

50° C. is very close to the temperature that can kill tissue. Therefore, unless the goal is to actually destroy tissue (high voltage tissue modification is discussed in Section III-B), the pulse duration should be limited to prevent ohmic heating to such an extent that the affected tissue is destroyed. For example, a 1 msec long pulse is nearly as effective at stunning tissue as is a 10 msec long pulse, but the temperature rise with the 1 msec long pulse is $\frac{1}{10}$ as large as with a 10 msec long pulse.

C. The Modification Mode

1. Low Voltage Modification

In the low voltage modification mode, the generator 46 transmits lower voltage radio frequency energy into a selected tissue region through either the same electrode(s) that are used to stun tissue, or different electrodes when the electrodes used to stun the tissue are not suitable for tissue modification. The radio frequency energy may, for example, have a waveform shape and duration that electrically heats and kills tissue in the selected region. When used in cardiac ablation, for example, the generator 46 is conditioned to deliver up to 150 watts of power for about 10 to 120 seconds at a radio frequency of 500 kHz. By destroying the tissue, the radio frequency energy forms a permanent electrical conduction block in the tissue region.

FIG. 5 shows a representative implementation for the switching element 80 associated with the generator 46 to change operation between the stunning mode and the modification mode. In this embodiment, the switching element input 82 (comprising supply and return lines) is coupled to the generator 46, which delivers radio frequency energy (500 kHz) at a prescribed energy input level suitable for stunning, as previously described. The switching element output 84 (also comprising supply and return lines) is coupled to the transmitting electrode(s) and to the return line electrode, designated $E_r$ in FIG. 5.

The switching element 80 includes an electronic switch 92 defining a first switch path 86 and a second switch path 90.

The first switch path 86 conditions the generator 46 for operation in the stunning mode. The first switch path 86 includes a first isolation transformer 88. The isolation transformer 88, shown in FIG. 5 as a 1:1 transformer, directs the stunning energy through the electrode(s) without amplitude modification for stunning tissue in the manner described. In the stunning mode, the electronic switch 92 transmits stunning energy through the first switch path 86 in short cycle intervals to deliver the energy in preset stunning pulses, as already described.

The switching element 80 also includes a second switch path 90, which conditions the generator 46 for operation in the modification mode. The second switch path 90 includes a second step-down isolation transformer 92, which is shown for the purpose of illustration having a step-down ratio of 3:1. The transformer 92 decreases the amplitude of the energy transmitted to the electrode(s) to lower levels suitable for ablating or otherwise modifying tissue. In the modification mode, the electronic switch 92 transmits energy through the second switch path 90 for longer cycle intervals conducive to tissue modification.

2. High Voltage Modification

High voltage energy pulses (such as RF pulses) can be used to kill or otherwise modify tissue in at least three ways. For example, the creation of high voltage gradients within the tissue dielectrically breaks down tissue structures. In addition, ohmically heating tissue will coagulate tissue structures, while ohmically heating to very high temperatures will vaporize tissue.

When voltage gradients at or above 500 volts/cm are induced in tissue, relatively short pulse durations can be used to destroy the tissue. Although voltage amplitudes 4 to 6 times higher than those used to stun tissue are required, the pulse duration requirements are on the order of 0.1 msec. As a result, the total pulse energy requirements for tissue destruction is similar to that used for stunning. In one preferred method, stunning pulses are delivered to identify tissue that is to be destroyed or otherwise modified. After the target tissue is identified, a tissue-destroying RF energy pulse could be delivered.

Turning to heating, a high voltage RF pulse (about 500 to 1200 volts in magnitude and about 50 to 100 msec in duration) delivers relatively high power to tissue, thereby enabling very rapid heating. Because the tissue is heated rapidly, there is essentially no convective heat loss during power application. These factors allow the thermal impulse response of the system to be measured based on the application of a stunning pulse, and the subsequent measurement of temperature at one or more locations on the electrode. From a power control standpoint, the impulse response of the system provides very important information as to the plant to be controlled. Short bursts of high voltage RF power, or more conventional continuous RF modification methods, may be used to thermally destroy tissue using feedback control algorithms that are optimized with the plant characterization obtained while applying a stunning pulse.

Tissue vaporization can be performed through the use of high voltage energy pulses with a pulse duration of about 250 msec to 1 sec. There are a number of therapeutic applications for this type of tissue vaporization. For example, percutaneous myocardial revascularization (PMR), which is currently performed using laser tissue vaporization, can be performed by using high voltage pulses to vaporize tissue. High voltage pulse-based tissue vaporization techniques may also be useful in certain cancer therapies and to channelize a vessel that has recently clotted off.

High voltage pulse-based tissue vaporization techniques can further be used to create a channel in soft tissue in order to gain access to the interior of a solid organ while maintaining hemostasis. The channel in the soft tissue would enable a diagnostic or therapeutic function (such as the formation of an area of modified tissue) to be performed on the selected organ.

D. Roving Pacing Mode

In an alternative embodiment, any of the multi-purpose stunning-modification probes discussed above can also be conditioned for use by the process controller 34 as a roving pacing probe, usable in tandem with the basket structure 20 to generate and verify the location output during the above described sampling and matching modes.

In this arrangement, the probe 16 is deployed in the heart region 12 while the multiple electrode structure 20 occupies the region 12. In this mode, the electrode(s) is electrically coupled to the pacing module 48 (as shown in phantom lines in FIG. 1) to emit pacing signals.

In use, once the process controller 32 generates the output location or locations using the electrodes 24 to pace the heart, the physician positions the probe within the localized region near the output location electrode or electrodes 24. As above described, the process controller 32 preferably includes the homing module 70 to aid the physician in guiding the probe 16 in the localized region within the structure 20.

The process controller 32 conditions the pacing module 48 to emit pacing signals through the probe electrode(s) to pace the heart in the localized region, while the electrodes 24 record the resulting electrograms. By pacing this localized region with the probe 16, while comparing the paced electrograms with the templates, the process controller 32 provides the capability of pacing and comparing at any location within the structure 20. In this way, the process controller 32 generates as output a location indicator that locates a site as close to a potential ablation site as possible.

Due to the often convoluted and complex contours of the inside surface of the heart, the basket structure 20 cannot contact the entire wall of a given heart chamber. The system 10 therefore can deploy the probe 16 outside the structure 20 to pace the heart in those wall regions not in contact with the electrodes 24. The probe 16 can also be deployed while the basket structure 20 occupies-the region 12 to pace the heart in a different region or chamber. In either situation, the electrodes 24 on the structure 20 record the resulting paced electrograms for comparison by the process controller 32 to the templates. The process controller 32 is thus able to generate an output identifying a location close to a potential ablation site, even when the site lies outside the structure 20 or outside the chamber that the structure 20 occupies.

E. Electrophysiologic Diagnosis Mode

The generator 46 can be operated in the stunning mode in association with the probe 16 to conduct diagnostic electrophysiological testing of tissue, such as myocardial tissue, in place of or in tandem with the mapping probe 14.

In this mode of operation, the physician conditions the generator 46 to transmit through the probe electrode(s) an electrical energy pulse, as previously described, which temporarily renders a zone of tissue electrically unresponsive. By sensing an electrophysiological effect due to the transmitted pulse, the physician can make diagnoses.

Such sensing is useful in the myocardial area where it can be used to diagnose the cause of cardiac events. For example, by temporarily rendering zones of myocardial tissue electrically unresponsive using an electrical energy pulse, and sensing the resulting electrophysiological effect, the physician can, without using the mapping probe 14, locate sites of automaticity, also called pacemaker sites, where arrhythmia originates. Likewise, the physician can, without using the mapping probe 14, locate the path or paths that maintain arrhythmia, previously referred to as the areas of slow conduction. Furthermore, by temporarily rendering zones of myocardial tissue electrically unresponsive using the electrical energy pulse, the physician can selectively alter the conduction properties of the heart within the localized zone without otherwise changing electrophysiological properties outside the zone. For example, the physician can create a temporary AV block by operating the generator 46 in the stunning mode, as previously described.

Based at least in part upon these diagnostic tests conducted in the stunning mode, the physician can proceed to altering an electrophysiological property of tissue in or near a diagnosed zone. For example, the physician can alter the electrophysiological property by ablating tissue in or near the diagnosed zone, as above described, using radio frequency electrical energy, or laser light energy, or an ablation fluid. The physician can also treat the diagnosed cardiac disorder without ablating tissue, using drugs such as quinidine, digitalis, and lidocaine.

IV. Bypass and Non-Bypass Environment Considerations

In many of the exemplary embodiments, the electrodes are exposed around their entire peripheries. These embodiments are particularly useful when the heart is on bypass and there is no blood flow within the heart. Here, air acts as an insulator and produces only modest convective cooling effects, as compared to a flowing blood pool that has a higher convection coefficient than virtually static air. Energy transmission is, therefore, essentially limited to the RF energy that is transmitted from the portion of the electrode surface that is in contact with the tissue to either a ground electrode, or another electrode within the group of electrode elements. Also, as noted above, the overall impedance of the system will increase (as compared to a situation where blood is present). This is due to the smaller effective surface area between the electrode and tissue.

Both of these conditions, focused RF energy and low heat dissipation into the air, will impact the ablation because they result in a high current density. When creating long lesions with a conventional catheter, char can be created as the tip is dragged because of the high current density and the difficulty in monitoring tissue temperature and controlling power that is inherent in the dragging process. Many of the present inventions, however, can take advantage of the high current density because the electrodes are not being dragged. For example, a number of electrodes can be used to ablate simultaneously because the effective (tissue contacting) surface area between all of the ablating electrodes is smaller and the convective cooling effects are reduced, as compared to situations where blood is present. This reduces the power requirements of the system. In addition, by using electrodes with lower thermal mass (as compared to a conventional solid tip electrode), less heat will be retained by the electrode and better temperature sensing can be made at the tissue surface. This will speed up the creation of the lesions and enable better lesion creation control.

In instances where the patient will not be on bypass and blood will be flowing past the electrodes, the portion of the electrode elements (or other operative elements) not intended to contact tissue may be masked through a variety of techniques. For example, a layer of UV adhesive (or another adhesive) may be painted on preselected portions of the electrode elements to insulate the portions of the elements not intended to contact tissue. Alternatively, a slotted sheath may be positioned over the portion of the electrode elements not intended to contact tissue. Deposition techniques may also be implemented to position a conductive surface only on those portions of the spline assembly intended to contact tissue.

Figure 34:
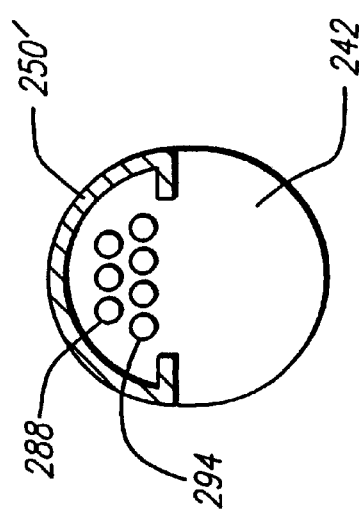
FIG. 34 is a section view showing a partially masked electrode.

As shown by way of example in FIG. 34, a polymer layer 293 may be thermally fused over an electrode, such as electrode 250, to mask desired portions of the electrodes. An exemplary process for applying the polymer layer is as follows. A segment of shaft tubing is cut long enough to cover the desired electrodes, and is then split in half (or other desired angle) along the axis. One half is placed over the assembled distal section so that it covers the side of the electrodes that are to be masked. A piece of polymeric shrink tubing, preferably RNF-100 or irradiated LDPE, is then carefully slid over the catheter distal end, so that the mask tubing is not moved from its placement over the electrodes and so that it stops approximately 2 cm beyond the end of the tubing half. The distal end is then heated in a controlled heat source at approximately 400° F. so that the mask tubing fuses into the distal shaft tubing along its length, and so that all of its edges are well fused into the shaft tubing, but not fused so much that the covered electrodes begin to poke through. Finally, the polymeric shrink tubing is split on one end and the assembly is heated at approximately 225° F. while the polymeric shrink tubing is slowly peeled off of the fused catheter shaft.

Figure 35:
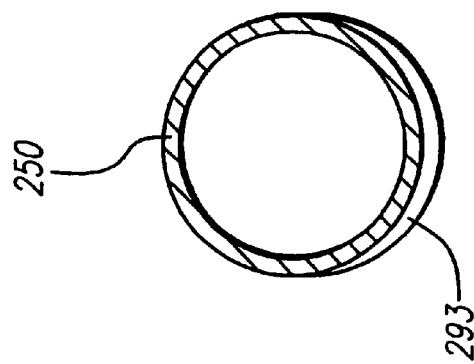
FIG. 35 is a section view showing an alternative electrode configuration.

Additionally, as illustrated in FIG. 35, the shape of an electrode 250' may be such that the metallic material in the region not intended to contact tissue is eliminated.

The masking techniques described in the preceding paragraph improve the efficiency of, for example, an ablation procedure by decreasing the surface area of the electrodes and, therefore, the energy required to heat tissue. The masking can be used to form a narrow electrode which is sometimes desirable, even when the patient will be on bypass. The convective cooling effects of blood flowing by the electrode are also reduced. In addition, the transmission of RF energy to unintended anatomic structures is prevented. This is especially important in epicardial applications when the ablation electrode elements may be sandwiched between multiple anatomic structures including, for example, the aorta and pulmonary artery.

It is also noteworthy that masking can be useful during bypass because tissue can partially wrap around the electrodes when the distal end of the device is pressed against the tissue. Such masking can also be used to control lesion thickness.

Although the present invention has been described in terms of the preferred embodiment above, numerous modifications and/or additions to the above-described preferred embodiments would be readily apparent to one skilled in the art. By way of example, but not limitation, methodologies of ablating tissue other than those described above can be used. Laser energy can be transmitted to ablate tissue and fluids like alcohol (ethanol), collagen, phenol, carbon dioxide, can also be injected into tissue to ablate it (see, for example, U.S. Pat. No. 5,385,148). It is intended that the scope of the present invention extends to all such modifications and/or additions.

I claim:

1. An electrophysiological method, comprising the steps of:

sensing a cardiac event; and transmitting an electrical energy to a zone of cardiac tissue that temporarily renders the zone of cardiac tissue electrically unresponsive for at least one second.

2. A method as claimed in claim 1, wherein the step of sensing a cardiac event comprises sensing an arrhythmia.

3. A method as claimed in claim 1, wherein the step of sensing a cardiac event comprises sensing at least one of a ventricular tachycardia, atrial tachycardia and atrial fibrillation.

4. A method as claimed in claim 1, wherein the step of sensing a cardiac event comprises placing an electrode in contact with cardiac tissue.

5. A method as claimed in claim 1, wherein the step of sensing a cardiac event comprises sensing a cardiac event with a catheter-mounted electrode.

6. A method as claimed in claim 1, further comprising the step of:
   identifying a target zone of cardiac tissue that, if rendered electrically unresponsive, would interrrupt the cardiac event; and
   wherein the step of transmitting electrical energy comprises transmitting electrical energy to the target zone of cardiac tissue that temporarily renders the target zone of cardiac tissue electrically unresponsive for at least one second.

7. A method as claimed in claim 1, wherein the step of transmitting electrical energy comprises transmitting an electrical energy pulse to a zone of cardiac tissue that temporarily renders the zone of cardiac tissue electrically unresponsive for at least one second.

8. A method as claimed in claim 1, wherein the step of transmitting electrical energy comprises transmitting electrical energy pulses to a zone of cardiac tissue that temporarily render the zone of cardiac tissue electrically unresponsive for at at least one second.

9. A method as claimed in claim 8, wherein the pulses comprise DC pulses.

10. A method as claimed in claim 8, wherein the pulses comprise AC pulses.

11. A method as claimed in claim 8, wherein the pulses comprise RF pulses.

12. A method as claimed in claim 1, wherein the step of transmitting electrical energy comprises transmitting energy with a catheter-mounted electrode to a zone of cardiac tissue that temporarily renders the zone of cardiac tissue electrically unresponsive for at least one second.

13. A method as claimed in claim 1, wherein the zone of cardiac tissue comprises a zone of cardiac tissue that, when rendered electrically unresponsive, interrupts the cardiac event.

14. A method as claimed in claim 1, wherein the zone of cardiac tissue comprises a slow conduction zone of cardiac tissue.

15. A method as claimed in claim 1, further comprising the step of:
   sensing whether the cardiac event has been interrupted while the zone of cardiac tissue is temporarily electrically unresponsive.

16. A method as claimed in claim 1, further comprising the step of:
   altering an electrophysiological property of the tissue in or near the zone of cardiac tissue.

17. A method of suppressing a cardiac event, comprising the steps of:
   sensing the cardiac event; and
   transmitting electrical energy to target cardiac tissue that temporarily creates an electrical conduction block in the target cardiac tissue for at least one second.

18. A method as claimed in claim 17, wherein the step of sensing a cardiac event comprises sensing an arrhythmia.

19. A method as claimed in claim 17, wherein the step of sensing a cardiac event comprises sensing at least one of a ventricular tachycardia, atrial tachycardia and atrial fibrillation.

20. A system as claimed in claim 17, wherein the step of sensing a cardiac event comprises placing an electrode in contact with cardiac tissue.

21. A method as claimed in claim 17, wherein the step of sensing a cardiac event comprises sensing a cardiac event with a catheter-mounted electrode.

22. A method as claimed in claim 17, wherein the step of transmitting electrical energy comprises transmitting an electrical energy pulse to target cardiac tissue that temporarily creates an electrical conduction block in the target cardiac tissue for at least one second.

23. A method as claimed in claim 17, wherein the step of transmitting electrical energy comprises tramsmitting electrical energy pulses to target cardiac tissue that that temporarily create an electrical conduction block in the target cardiac tissue for at least one second.

24. A method as claimed in claim 23, wherein the pulses comprise DC pulses.

25. A method as claimed in claim 23, wherein the energy pulse comprise AC pulses.

26. A method as claimed in claim 23, wherein the pulses comprise RF pulses.

27. A method as claimed in claim 17, wherein the step of transmitting electrical energy comprises transmitting electrical energy with a catheter-mounted electrode to target cardiac tissue that temporarily creates an electrical conduction block in the target cardiac tissue for at least one second.

28. A method as claimed in claim 17, wherein the target cardiac tissue comprises a slow conduction zone of cardiac tissue.

29. A method as claimed in claim 17, further comprising the step of:
   sensing whether the cardiac event has been interrupted while the temporary electrical conduction block exists.

30. A method as claimed in claim 17, further comprising the step of:
   altering an electrophysiological property of the tissue in or near the target cardiac tissue.

* * * * *